(12) United States Patent
De La Torre-Bueno et al.

(10) Patent No.: US 7,272,252 B2
(45) Date of Patent: Sep. 18, 2007

(54) AUTOMATED SYSTEM FOR COMBINING BRIGHT FIELD AND FLUORESCENT MICROSCOPY

(75) Inventors: Jose De La Torre-Bueno, Encinitas, CA (US); James McBride, Mission Viejo, CA (US)

(73) Assignee: Clarient, Inc., San Juan Capistrano, CA (US)

( * ) Notice: Subject to any disclaimer, the term of this patent is extended or adjusted under 35 U.S.C. 154(b) by 859 days.

(21) Appl. No.: 10/461,786

(22) Filed: Jun. 12, 2003

(65) Prior Publication Data

US 2003/0231791 A1  Dec. 18, 2003

Related U.S. Application Data

(60) Provisional application No. 60/450,824, filed on Feb. 27, 2003, provisional application No. 60/388,522, filed on Jun. 12, 2002.

(51) Int. Cl.
*G06K 9/00* (2006.01)
(52) U.S. Cl. ...................... 382/133; 382/318
(58) Field of Classification Search ............... 382/128, 382/133, 134, 318, 319; 356/39; 128/922
See application file for complete search history.

(56) References Cited

U.S. PATENT DOCUMENTS

| | | | |
|---|---|---|---|
| 3,824,393 A | 7/1974 | Brain | 250/222 PC |
| 3,851,972 A | 12/1974 | Smith et al. | 356/72 |
| 4,011,004 A | 3/1977 | Levine et al. | 350/90 |
| 4,125,828 A | 11/1978 | Resnick et al. | 340/146.3 CA |
| 4,196,265 A | 4/1980 | Koprowski et al. | 435/2 |
| 4,210,419 A | 7/1980 | Castleman | 23/230 B |
| 4,249,825 A | 2/1981 | Shapiro | 356/223 |
| 4,338,024 A | 7/1982 | Bolz et al. | 356/23 |
| 4,393,466 A | 7/1983 | Deindoerfer et al. | 364/415 |
| 4,513,438 A | 4/1985 | Graham et al. | 382/6 |
| 4,612,614 A | 9/1986 | Deindoerfer et al. | 364/415 |
| 4,656,594 A | 4/1987 | Ledley | 364/498 |
| 4,673,973 A | 6/1987 | Ledley | 358/93 |
| 4,700,298 A | 10/1987 | Palcic et al. | 364/414 |
| 4,741,043 A | 4/1988 | Bacus | 382/6 |
| 4,945,220 A | 7/1990 | Mallory et al. | 250/201.3 |
| 4,965,725 A | 10/1990 | Rutenberg | 364/413.1 |
| 4,991,223 A | 2/1991 | Bradley | 382/17 |
| 5,003,165 A | 3/1991 | Sarfati et al. | 250/201.2 |
| 5,008,185 A | 4/1991 | Bacus | 435/7.23 |
| 5,016,173 A | 5/1991 | Kenet et al. | 364/413.1 |
| 5,018,209 A | 5/1991 | Bacus | 382/6 |
| 5,068,909 A | 11/1991 | Rutherford et al. | 382/49 |
| 5,085,325 A | 2/1992 | Jones et al. | 209/580 |
| 5,087,965 A | 2/1992 | Torre-Bueno | 358/22 |
| 5,123,055 A | 6/1992 | Kasdan | 382/6 |
| 5,162,990 A * | 11/1992 | Odeyale et al. | 364/413.1 |
| 5,202,931 A | 4/1993 | Bacus | 382/6 |
| 5,231,580 A | 7/1993 | Cheung et al. | 364/413.13 |
| 5,233,684 A | 8/1993 | Ulichney | 395/131 |
| 5,254,845 A | 10/1993 | Burgess et al. | 250/201.3 |
| 5,257,182 A | 10/1993 | Luck et al. | 364/413.1 |
| 5,268,966 A | 12/1993 | Kasdan | 382/6 |
| 5,287,272 A | 2/1994 | Rutenberg et al. | 364/413.01 |
| 5,317,140 A | 5/1994 | Dunthorn | 250/221 |
| 5,321,545 A | 6/1994 | Bisconte | 359/391 |
| 5,333,207 A | 7/1994 | Rutenberg | 382/6 |
| 5,338,924 A | 8/1994 | Barrett et al. | 250/201.4 |
| 5,352,613 A | 10/1994 | Tafas et al. | 436/63 |
| 5,375,177 A | 12/1994 | Vaidyanathan et al. | 382/48 |
| 5,409,007 A | 4/1995 | Saunders et al. | 128/661.01 |
| 5,428,690 A | 6/1995 | Bacus et al. | 382/128 |
| 5,432,871 A | 7/1995 | Novik | 382/232 |
| 5,449,622 A | 9/1995 | Yabe et al. | 436/63 |
| 5,459,384 A | 10/1995 | Engelse et al. | 318/640 |
| 5,463,470 A | 10/1995 | Terashita et al. | 358/298 |
| 5,469,353 A | 11/1995 | Pinsky et al. | 364/413.01 |
| 5,473,706 A | 12/1995 | Bacus et al. | 382/133 |
| 5,481,401 A | 1/1996 | Kita et al. | 359/353 |
| 5,499,097 A | 3/1996 | Ortyn et al. | 356/372 |
| 5,515,172 A | 5/1996 | Shiau | 358/298 |
| 5,526,258 A | 6/1996 | Bacus | 364/413.1 |
| 5,533,628 A | 7/1996 | Tao | 209/580 |

(Continued)

FOREIGN PATENT DOCUMENTS

DE    3340647 A1    5/1985

(Continued)

OTHER PUBLICATIONS

Aziz, Douglas C., "Quantitation of Estrogen and Progesterone Receptors by Immunocytochemical and Image Analyses", Anatomic Pathology, From Cytometrics, Inc., Division of Specialty Laboratories, pp. 105-111, Jul. 1991.

(Continued)

*Primary Examiner*—Andrew W. Johns
(74) *Attorney, Agent, or Firm*—Patterson, Thuente, Skaar & Christensen, P.A.

(57) ABSTRACT

A method and apparatus for automated analysis of transmitted and fluorescently labeled biological samples, wherein the apparatus automatically scans at a low magnification to acquire images which are analyzed to determine candidate cell objects of interest. Once candidate objects of interest are identified, further analysis is conducted automatically to process and collect data from samples having different staining agents.

54 Claims, 26 Drawing Sheets

U.S. PATENT DOCUMENTS

| | | | | |
|---|---|---|---|---|
| 5,583,666 A | 12/1996 | Ellson et al. | | 358/518 |
| 5,585,469 A | 12/1996 | Kojima et al. | | 534/573 |
| 5,586,160 A | 12/1996 | Mascio | | 378/37 |
| 5,602,937 A | 2/1997 | Bedrosian et al. | | 382/151 |
| 5,602,941 A | 2/1997 | Charles et al. | | 382/251 |
| 5,619,032 A | 4/1997 | Kasdan | | 250/201.3 |
| 5,625,705 A | 4/1997 | Recht | | 382/128 |
| 5,625,709 A | 4/1997 | Kasdan | | 382/203 |
| 5,635,402 A | 6/1997 | Alfano et al. | | 436/63 |
| 5,646,677 A | 7/1997 | Reber | | 348/13 |
| 5,647,025 A | 7/1997 | Frost et al. | | 382/255 |
| 5,671,288 A | 9/1997 | Wilhelm et al. | | 382/128 |
| 5,690,892 A | 11/1997 | Babler et al. | | 422/63 |
| 5,691,779 A | 11/1997 | Yamashita et al. | | 348/645 |
| 5,701,172 A | 12/1997 | Azzazy | | 356/28 |
| 5,706,093 A | 1/1998 | Komiya | | 356/418 |
| 5,726,009 A | 3/1998 | Connors et al. | | 435/4 |
| 5,732,150 A | 3/1998 | Zhou et al. | | 382/133 |
| 5,735,387 A | 4/1998 | Polaniec et al. | | 198/690.1 |
| 5,740,267 A | 4/1998 | Echerer et al. | | 382/132 |
| 5,740,270 A | 4/1998 | Rutenberg et al. | | 382/133 |
| 5,773,459 A | 6/1998 | Tang et al. | | 514/445 |
| 5,783,814 A | 7/1998 | Fairley et al. | | 250/201.3 |
| 5,795,723 A | 8/1998 | Tapscott et al. | | 435/6 |
| 5,799,105 A | 8/1998 | Tao | | 382/167 |
| 5,846,749 A | 12/1998 | Slamon et al. | | 435/7.23 |
| 5,854,851 A | 12/1998 | Bamberger et al. | | 382/133 |
| 5,867,598 A | 2/1999 | de Queiroz | | 382/235 |
| 5,877,161 A | 3/1999 | Riabowol | | 514/44 |
| 5,880,473 A | 3/1999 | Ginestet | | 250/458.1 |
| 5,888,742 A | 3/1999 | Lal et al. | | 435/6 |
| 5,889,881 A | 3/1999 | MacAulay et al. | | 382/133 |
| 5,911,003 A | 6/1999 | Sones | | 382/162 |
| 5,911,327 A | 6/1999 | Tanaka et al. | | 209/580 |
| 5,966,309 A | 10/1999 | O'Bryan et al. | | 364/478.13 |
| 5,966,465 A | 10/1999 | Keith et al. | | 382/232 |
| 5,989,835 A | 11/1999 | Dunlay et al. | | 435/7.2 |
| 6,006,191 A | 12/1999 | DiRienzo | | 705/2 |
| 6,007,996 A | 12/1999 | McNamara et al. | | 435/6 |
| 6,011,595 A | 1/2000 | Henderson et al. | | 348/590 |
| 6,031,929 A | 2/2000 | Maitz et al. | | 382/132 |
| 6,040,139 A | 3/2000 | Bova | | 435/6 |
| 6,058,322 A | 5/2000 | Nishikawa et al. | | 600/408 |
| 6,072,570 A | 6/2000 | Chipman et al. | | 356/124 |
| 6,097,838 A | 8/2000 | Klassen et al. | | 382/167 |
| 6,101,265 A | 8/2000 | Bacus et al. | | 382/133 |
| 6,103,518 A | 8/2000 | Leighton | | 435/286.3 |
| 6,117,985 A | 9/2000 | Thomas et al. | | 530/413 |
| 6,122,400 A | 9/2000 | Reitmeier | | 382/166 |
| 6,125,194 A | 9/2000 | Yeh et al. | | 382/132 |
| 6,141,602 A | 10/2000 | Igarashi et al. | | 700/226 |
| 6,151,535 A | 11/2000 | Ehlers | | 700/226 |
| 6,169,816 B1 | 1/2001 | Ravkin | | 382/128 |
| 6,215,892 B1 | 4/2001 | Douglass et al. | | 382/128 |
| 6,215,894 B1 | 4/2001 | Zeleny et al. | | 382/133 |
| 6,225,636 B1 | 5/2001 | Ginestet | | 250/458.1 |
| 6,226,392 B1 | 5/2001 | Bacus et al. | | 382/128 |
| 6,236,031 B1 | 5/2001 | Ueda | | 250/201.5 |
| 6,238,892 B1 | 5/2001 | Mercken et al. | | 435/70.21 |
| 6,259,807 B1 | 7/2001 | Ravkin | | 382/133 |
| 6,272,247 B1 | 8/2001 | Manickam et al. | | 382/217 |
| 6,281,874 B1 | 8/2001 | Sivan et al. | | 345/127 |
| 6,290,907 B1 | 9/2001 | Takahashi et al. | | 422/65 |
| 6,313,452 B1 | 11/2001 | Paragano et al. | | 250/201.3 |
| 6,374,989 B1 | 4/2002 | Van Dyke, Jr. et al. | | 198/478.1 |
| 6,404,916 B1 | 6/2002 | De La Torre-Bueno | | 382/162 |
| 6,406,840 B1 | 6/2002 | Li et al. | | 435/1.3 |
| 6,418,236 B1 | 7/2002 | Ellis et al. | | 382/128 |
| 6,466,690 B2 | 10/2002 | Bacus et al. | | 382/133 |
| 6,518,554 B1 | 2/2003 | Zhang | | 250/201.3 |
| 6,553,135 B1 | 4/2003 | Douglass et al. | | 382/128 |
| 6,573,043 B1 | 6/2003 | Cohen et al. | | 435/6 |
| 6,631,203 B2 | 10/2003 | Ellis et al. | | 382/128 |
| 6,671,393 B2 | 12/2003 | Hays et al. | | 382/128 |
| 6,674,896 B1 | 1/2004 | Torre-Bueno | | 382/162 |
| 6,697,509 B2 | 2/2004 | De La Torre-Bueno | | 382/133 |
| 6,718,053 B1 | 4/2004 | Ellis et al. | | 382/128 |
| 2002/0067409 A1 | 6/2002 | Harari et al. | | 348/80 |
| 2002/0164810 A1 | 11/2002 | Dukor et al. | | 436/64 |
| 2003/0124589 A1 | 7/2003 | Piper | | 435/6 |
| 2003/0170703 A1 | 9/2003 | Piper et al. | | 435/6 |

FOREIGN PATENT DOCUMENTS

| | | |
|---|---|---|
| DE | 3735091 A1 | 4/1998 |
| EP | 0213666 A1 | 3/1987 |
| EP | 0 557 871 A2 | 9/1993 |
| EP | 0713086 A1 | 5/1996 |
| WO | WO92/17848 A1 | 10/1992 |
| WO | WO97/20198 A2 | 6/1997 |
| WO | WO00/49391 A1 | 8/2000 |
| WO | WO01/37206 A1 | 5/2001 |
| WO | WO03/014795 A1 | 2/2003 |

OTHER PUBLICATIONS

Bacus S. et al., "The Evaluation of Estrogen Receptor in Primary Breast Carcinoma by Computer-Assisted Image Analysis", American Journal of Clinical Pathology, vol. 90, No. 2, Aug. 1988, pp. 233-239.

Baddoura, Fady K. et al., "Image Analysis for Quantitation of Estrogen Recptor in Formalin-Fixed Paraffin-Embedded Sections of Breast Carcinoma", Modern Pathology, vol. 4, No. 1, 1991, pp. 91-95.

Bander, N.H., Monoclonal antibodies to renal cancer antigens, vol. 18, Supp. 2, pp. 10-12, 1990. Abstract.

Baxes, G.A., "Digital Image Processing," pp. 127-137.

Caulet S. et al., "Comparative Quantitative Study of Ki-67 Antibody Staining in 78 B and T Cell Malignant Lymphoma (ML) Using Two Image Analyser Ssytems", Path. Res. Pract. 188, 490-496 (1992).

Cote, R.J., et al., "Prediction of Early Relapse in Patients with Operable Breast Cancer by Detection of Occult Bone Marrow Micrometastases," Journal of Clinical Oncology, vol. 9, No. 10, pp. 1749-1756, Oct. 1991.

Diamond, David A. et al.,"Computerized Image Analysis of Nuclear Shape as a Prognostic Factor for Prostatic Cancer", The Prostate 3:321-332 (1982).

Drobnjak, M. et al., "Immunocytochemical, Detection of Estrogen and Progesterone Receptors (ER/PE) in Paraffin Sections of Human Breast Cancinoma. Correlation with Biochemical Analysis and Automated Imaging Quantitation" Journal of the Academy of Pathology, vol. 64, No. 1, Jan. 1991. Abstract.

Enestrom, Sverker et al., "Quantitative Ultrastructural Immunocytochemistry Using a Computerized Image Analysis System", Stain Technology, vol. 65, No. 6, pp. 263-278, 1990.

Esteban, J.M. et al., "Quantification of Estrogen Receptors on Paraffin-Embedded Tumours by Image Analysis", Modern Pathology, vol. 4, No. 1, pp. 53-57.

Goldschmidt, R.A. et al., "Automated Immunohistochemical Estrogen Receptor Staining and Computerized Image Analysis-Comparison with Biochemical Methods", Supplied by the British Library—"The world's knowledge" www.bl.uk.

Gross, Douglas S. et al., "Quantitative Immunocytochemistry of Hypothalamic and Pituitary Hormones: Validation of an Automated, Computerized Image Analysis System", The Journal of Histochemistry and Cytochemistry, vol. 33, No. 1, pp. 11-20, 1985.

Horsfall, D.J. et al., "Immunocytochemical assay for oestrogen receptor in fine needle aspirates of breast cancer by video image analysis", Br. J. Cancer (1989), 59, 129-134.

Kerns, B.J. et al., "Estrogen receptor status evaluated in formalin-fixed paraffin embedded breast carcinomas determined by automated immunohistochemistry and image analysis", Proceedings of the American Association for Cancer Research, vol. 35, Mar. 1994.

Levine, Gary M. et al., "Quantitative Immunocytochemistry by Digital Image Analysis: Application to Toxicologic Pathology", XICOLOGIC Pathology ISSN:0192-6233, vol. 15, No. 3, pp. 303-307, 1987.

Mansi, J.L. et al., "Bone Marrow Micrometastases in Primary Breast Cancer: Prognostic Significance After 6 Years' Follow-Up," Eur. J. Cancer, vol. 27, No. 12, pp. 1552-1555, 1991.

Maudelonde, T. et al., "Immunostaining of Cathespin D in Breast Cancer: Quantification by Computerised Image Analysis and Correlation with Cytosolic Assay", Eur T Cancer, vol. 28A, No. 10, pp. 1686-1691, 1992.

MClelland, Richard A., et al., "A Multicentre Study into the Reliability of Steroid Receptor Immunocytochemical Assay Quantification", The European Journal of Cancer, vol. 27, No. 6, Jun. 1991, pp. 711-715.

McClelland, Richard A. et al., "Automated Quantitation of Immunocytochemically Localized Estrogen Receptors in Human Breast Cancer", Cancer Research 50, 3545-3550, Jun. 1990.

McKeough et al., "A Low-Cost Automatic Translation and Autofocusing System for a Microscope", Measurement Science and Technology, IOP Publishing, Bristol, GB, vol. 6, No. 5, pp. 583-587, May 1, 1995.

Mize, R. Ranney et al., "Quantitative immunocytochemistry using an image analyzer. I. Hardware evaluation, image processing, and data analysis", Journal of Neuroscience Methods, 26 (1988) 1-24.

Moss, T.J., et al., "Prognostic Value of Immunocytologic Detection of Bone Marrow Metastases in Neuroblastoma," The New England Journal of Medicine, vol. 324, No. 4, pp. 219-226, Jan. 1991.

Press, Michael F. et al., "Her-2/*nue* Expression in Node-negative Breast Cancer: Direct Tissue Quantitation by Computerized Image Analysis and Association of Overexpresion with Increased Risk of Recurrent Disease", Cancer Research 53, 4960-4970, Oct. 1993.

Price, J.O. et al., "Prenatal Diagnosis with Fetal Cells Isolated from Maternal Blood by Multiparameter Flow Cytometry," AM. J. Obstet. Gynecol., vol. 165, pp. 1731-1737, Dec. 1991.

Roca et al., "New Autofocusing Algorithm for Cytological Tissue in a Microscopy Environment", Optical Engineering, Soc. of Photo-Optical Instrumentation Engineers, Bellingham, US, vol. 37, No. 2, pp. 635-641, Feb. 1, 1998.

Schultz, Daniel S., et al., "Comparison of Visual and CAS-200 Quantitation of Immunocytochemical Staining in Breast Carcinoma Samples", Analytical and Quatitative Cytology and Histology, vol. 14, No. 1, Feb. 1992.

Simpson, J.L. and Elias, S., "Isolating Fetal Cells From Maternal Blood—Advances in Prenatal Diagnosis Through Molecular Technolgy," JAMA, vol. 270, No. 19, pp. 2357-2361, Nov. 17, 1993.

Unnerstall, James R. et al., "New Approaches to Quantitative Neuropathology: Multtivariate Analysis of Morphologic and Neurochemical Measures", Neurobiology of Aging, vol. 8, pp. 567-569, Pergamon Journals Ltd., 1987.

Kohler et al., "Continuous cultures of fused cells secreting antibody of predefined specificity," NAture 256: 495-497, (1975).

Kononen e tal., "Tissue microarrays for high-throughput molecular profiling of tumor specimens," Nature Medicine 4(7): 844-847, (1988).

Pertchuk et al., "Estrogen receptor immunocytochemistry in paraffin embedded tissues with ER1D5 predicts breast cancer endocrine response more accurately than H222Spy in frozen sections of cytosol-based ligand-binding assays," Cancer 77: 2514-2519 (1996).

Rose, S.L. and R.E. Buller, "The role of p53 mutation in BRCA1-associated ovarian cancer," Minerva Ginecol. 54(3): 201-209 (202).

Russ, J.C., The Image Processing Handbook, Boca Raton: CRC Press, pp. 225 & 337 (1995).

* cited by examiner

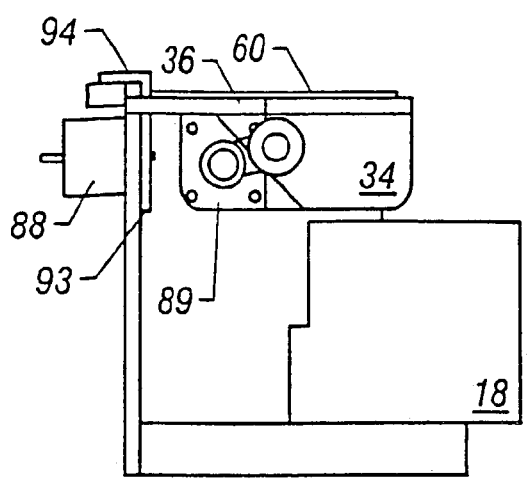
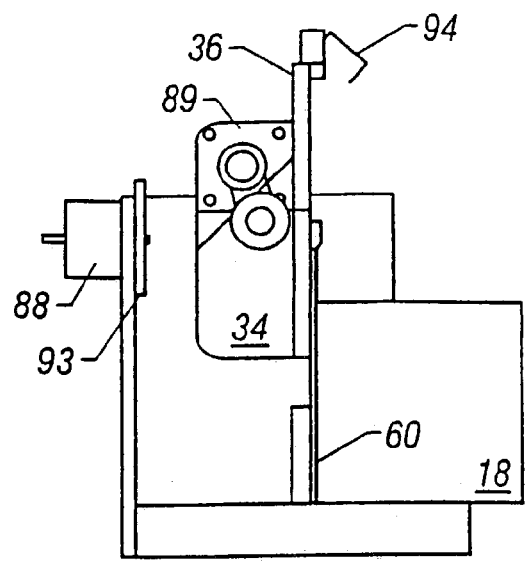
FIG. 9A    FIG. 9B
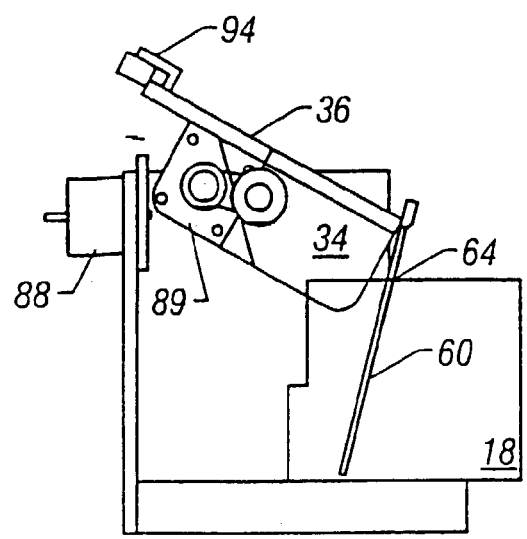
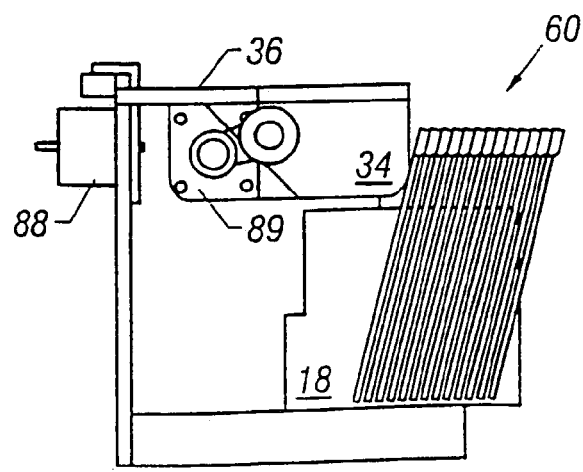
FIG. 9C    FIG. 9D

AUTOMATED SYSTEM FOR COMBINING BRIGHT FIELD AND FLUORESCENT MICROSCOPY

CROSS REFERENCE TO RELATED APPLICATIONS

The present application claims priority under 35 U.S.C. §119 to U.S. Provisional Application Ser. No. 60/450,824 filed Feb. 27, 2003 and U.S. Provisional Application Ser. No. 60/388,522, filed Jun. 12, 2002, the disclosures of which are incorporated herein by reference.

TECHNICAL FIELD

The invention relates generally to light microscopy and fluorescent microscopy and, more particularly, to automated light and fluorescent microscopic methods and an apparatus for detection of objects in a sample.

BACKGROUND

In the field of medical diagnostics and research including oncology, the detection, identification, quantification, and characterization of cells of interest, such as cancer cells, through testing of biological samples is an important aspect of diagnosis and research. Typically, a biological sample such as bone marrow, lymph nodes, peripheral blood, cerebrospinal fluid, urine, effusions, fine needle aspirates, peripheral blood scrapings or other biological materials are prepared by staining a sample to identify cells of interest.

In Fluorescent In Situ Hybridization (FISH) a fluorescently labeled oligonucleotide probe is added to a tissue sample on a microscope slide under conditions that allow for the probe to enter the cell and enter the nucleus. If the labeled sequence is complementary to a sequence in a cell on the slide a fluorescent spot will be seen in the nucleus when the cell is visualized on a fluorescent microscope. FISH has the advantage that the individual cells containing the DNA sequences being tested can be visualized in the context of the tissue.

FISH assays can be visualized with the naked eye as well as with video cameras. Problems are associated with both methods. Manual visualization by technicians results in the potential for subjective determinations and lack of reproducibility between one or more technicians viewing the same slide. Automated imaging with a camera takes several seconds for each area of a slide to be imaged to detect a fluorescent signal. In contrast, a camera on a bright field microscope can collect a new image every 1/60 of a second. Accordingly, a system that images all parts of a slide in about 6 minutes in bright field, may take an hour or more to collect a set of fluorescent images of the same slide. Thus a faster, more efficient, and reproducible method of imaging slides containing fluorescent agents is needed.

SUMMARY

The invention provides a method, an apparatus, and a system for accurately and efficiently imaging a slide containing a fluorescent signal.

In accordance with the invention, a slide prepared with a biological sample and reagent maybe loaded onto the system or may be placed in a slide carrier that holds any number of additional slides (e.g., 1-50 slides/carrier). The slide carriers are loaded into an input hopper of the automated system. An operator may then enter data identifying the size, shape, and location of a scan area on each slide or the system can automatically locate a scan area for each slide during slide processing. The processing parameters of the slide may be identified by a bar code present on the slide or slide carrier. At system activation, a slide carrier is positioned on an X-Y stage, the entire slide is rapidly scanned at a low magnification, typically 10× under transmitted light. At each location of the scan, a low magnification image is acquired and processed to detect candidate objects of interest. Typically, color, size and shape are used to identify objects of interest. The location of each candidate object of interest is stored.

At the completion of the low level scan for each slide, the optical system is adjusted to a higher magnification such as 40× or 60×, and the X-Y stage is positioned to the stored locations of the candidate objects of interest on a slide. A higher magnification image is acquired for each candidate object of interest and a series of image processing steps are performed to confirm the analysis that was performed at low magnification. A high magnification image is stored for each confirmed object of interest.

These images are then available for retrieval by a pathologist or cytotechnologist to review for final diagnostic evaluation. Having stored the location of each object of interest, a mosaic comprised of the candidate objects of interest for a slide may be generated and stored. The pathologist or cytotechnologist may view the mosaic or may also directly view the slide at the location of an object of interest in the mosaic for further evaluation. The mosaic may be stored on magnetic or optical or other media for future reference or may be transmitted to a remote site for review and/or storage. The entire process involved in examining a single slide takes on the order of 2-15 minutes depending on scan area size and the number of detected candidate objects of interest.

The invention has utility in the field of oncology for the early detection of minimal residual disease ("micrometastases"). Other useful applications include prenatal diagnosis of fetal cells in maternal blood and in the field of infectious diseases to identify pathogens and viral loads, alkaline phosphatase assessments, reticulocyte counting, and others.

The processing of images acquired in the automated scanning of the invention includes, or a process of transforming the image to a different color space; filtering the transformed image with a low pass filter; dynamically thresholding the pixels of the filtered image to suppress background material; performing a morphological function to remove artifacts from the thresholded image; analyzing the thresholded image to determine the presence of one or more regions of connected pixels having the same or similar color; and categorizing every region having a size greater than a minimum (threshold) size as a candidate object of interest.

According to another aspect of the invention, the scan area is automatically determined by scanning the slide; acquiring an image at each slide position; analyzing texture information of each image to detect the edges of the specimen; and storing the locations corresponding to the detected edges to define the scan area. According to yet another aspect of the invention, automated focusing of the optical system is achieved by initially determining a focal plane from an array of points or locations in the scan area. The derived focal plane enables subsequent rapid automatic focusing in the low power scanning operation. The focal plane is determined by determining proper focal positions across an array of locations and performing an analysis such as a least squares fit of the array of focal positions to yield a focal plane across the array. Preferably, a focal position at each location is determined by incrementing the position of a Z stage for a fixed number of coarse and fine iterations. At each iteration, an image is acquired and a pixel variance or other optical parameter about a pixel mean for the acquired image is calculated to form a set of variance data. A least squares fit is performed on the variance data according to a known function. The peak value of the least squares fit curve is selected as an estimate of the best focal position.

In another aspect of the invention, another focal position method for high magnification locates a region of interest centered about a candidate object of interest within a slide that was located during an analysis of the low magnification images. The region of interest is preferably n columns wide, where n is a power of 2. The pixels of this region are then processed using a Fast Fourier Transform to generate a spectra of component frequencies and corresponding complex magnitude for each frequency component. Magnitude of the frequency components that range from 25% to 75% of the maximum frequency component are squared and summed to obtain the total power for the region of interest. This process is repeated for other Z positions and the Z position corresponding to the maximum total power for the region of interest is selected as the best focal position. This process is used to select a Z position for regions of interest for slides containing, for example, neutrophils stained with Fast Red to identify alkaline phosphatase in cell cytoplasm and counterstained with hematoxylin to identify the nucleus of the neutrophil cell. This focal method may be used with other stains and types of biological samples, as well.

In yet another aspect of the invention, a method and apparatus for the automatic analysis of fluorescent specimens are provided. A slide, which may contain fluorescent specimens, is loaded onto the automated system. The slide, or portions thereof, containing the specimen is scanned in transmitted light. Once the image is scanned and the candidate objects of interest are identified under transmitted light, an illuminating (fluorescent excitation) light is then applied to the candidate objects of interest, previously identified, to collect images of the relevant fluorescent portions for further analysis. The initial automatic scanning method useful for this method is not limited to that disclosed above, any automatic scanning method for identifying candidate objects of interest is contemplated.

The initial scan can be performed in transmitted light in bright field or dark field. Under bright field, the angle of the light being transmitted through the slide, and any specimens thereon, is such that unless the light is blocked/absorbed by the specimen, it passes directly into the objective. Therefore, under bright light, the background will appear bright and the areas containing specimens will appear darker, the light having had to pass through the specimen, and therefore absorbed to a degree, before it reaches the objective. In contrast, under dark field, the angle of the light being transmitted through the slide is such that if the light is not scattered by specimens on the slide, it will not enter the objective. Accordingly, the background area will be dark, i.e., no specimen to scatter the light, and the areas containing the specimen will be brighter, as they scatter the light into the objective.

Once the image is scanned, the automated system can identify candidate objects of interest. The automated system can then locate the candidate object of interest and further process the specimen, such as storing the information, applying an illuminating (fluorescent excitation) light, enlarging the image under high magnification, capturing the image, or any combination thereof.

The transmitted light scan and the subsequent fluorescent illumination/excitation can be performed on the same slide. Alternatively, they can be performed on slides of two adjacent serial sections. In the case of the latter, there should be a way to orient the sections to correspond with each other, for example, an outline of the tissues on each slide or at least two landmarks on serial sections can be used to orient the sections.

According to still another aspect of the invention, a method and apparatus for automated slide handling is provided. A slide is mounted onto a slide carrier with a number of other slides. The slide carrier is positioned in an input feeder with other slide carriers to facilitate automatic analysis of a batch of slides. The slide carrier is loaded onto the X-Y stage of the optical system for the analysis of the slides thereon. Subsequently, the first slide carrier is unloaded into an output feeder after automatic image analysis and the next carrier is automatically loaded.

Also provided is an apparatus for processing slides according to the methods above. The apparatus includes a computer having at least one system processor with image processing capability, a computer monitor, an input device, a power supply and a microscope subsystem. The microscope subsystem includes an optical sensing array for acquiring images. A two-dimensional motion stage for sample movement and for focus adjustment, and input and output mechanisms for multiple sample analysis and storage. The apparatus may also include a transmitted light source as well as an illuminating/fluorescent excitation light source for fluorescing samples.

BRIEF DESCRIPTION OF THE DRAWINGS

The above and other features of the invention including various novel details of construction and combinations of parts will now be more particularly described with reference to the accompanying drawings and pointed out in the claims. It will be understood that the particular apparatus embodying the invention is shown by way of illustration only and not as a limitation of the invention. The principles and features of this invention may be employed in varied and numerous embodiments without departing from the scope of the invention.

FIG. 6b is a bottom view of the slide carrier of FIG. 6a.

FIGS. 9a-9d illustrate the output operation of the automated slide handling subsystem.

DETAILED DESCRIPTION

Figure 1:
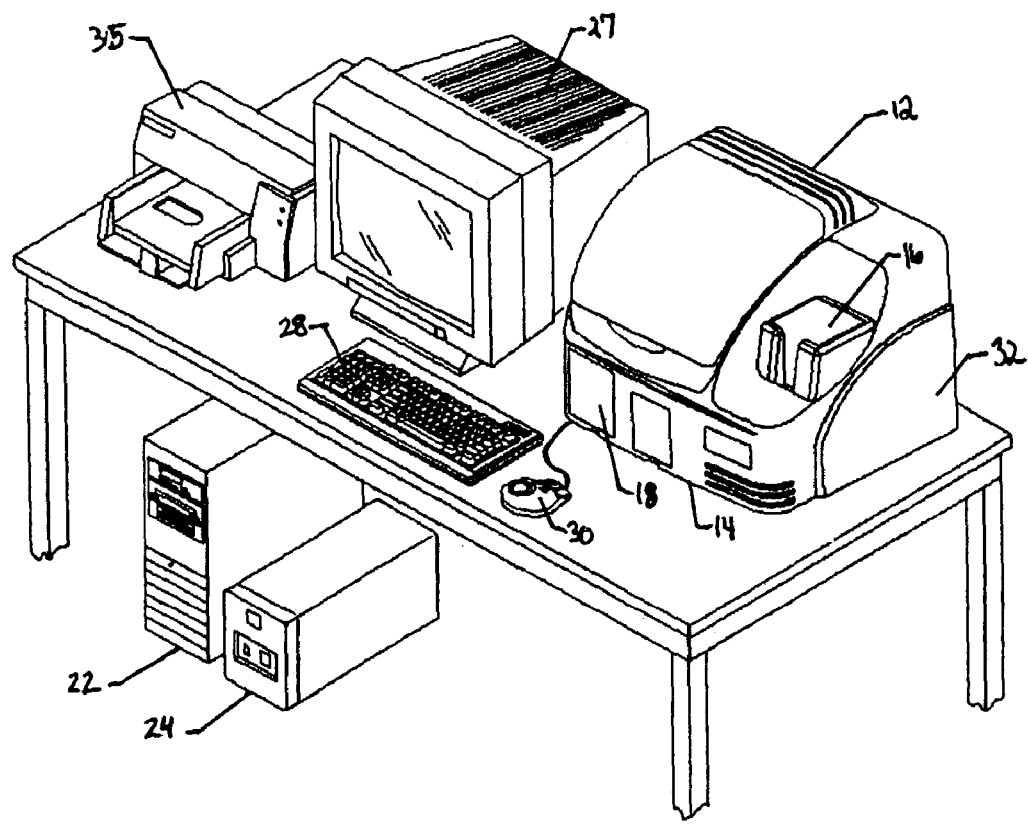
FIG. 1 is a perspective view of an exemplary apparatus for automated cell analysis embodying the invention.

The biological mechanisms of many diseases have been clarified by microscopic examination of tissue samples. Histopathological examination has also permitted the development of effective medical treatments for a variety of illnesses. In standard anatomical pathology, a diagnosis is made on the basis of cell morphology and staining characteristics. Tumor samples, for example, can be examined to characterize the tumor type and suggest whether the patient will respond to a particular form of chemotherapy. Microscopic examination and classification of tissue samples stained by standard methods (such as hematoxylin and eosin) has improved cancer treatment significantly. Even with these advancements many cancer treatments are ineffective. This is due to the fact that many cancers are the result of changes in cellular machinery that provides the phenotypic changes resulting in aberrant cellular proliferation. Thus, due to the diverse nature of the changes that cause various cancers, a cancer condition caused by one cellular mechanism may be treatable by one therapeutic regimen, while a similar cancer, if caused by a different cellular mechanism requires a different therapeutic regimen.

Recent advances in molecular medicine have provided an even greater opportunity to understand the cellular mechanisms of disease, and select appropriate treatments with the greatest likelihood of success. For example, some hormone dependent breast tumor cells have an increased expression of estrogen receptors indicating that the patient from whom the tumor was taken will likely respond to certain anti-estrogen drug treatments. Other diagnostic and prognostic cellular changes include the presence of tumor specific cell surface antigens (as in melanoma), the production of embryonic proteins (such as carcinoembryonic glycoprotein antigen produced by gastrointestinal tumors), and genetic abnormalities (such as activated oncogenes in tumors). A variety of techniques have evolved to detect the presence of these cellular abnormalities, including immunophenotyping with monoclonal antibodies, in situ hybridization using nucleic acid probes, and DNA amplification using the polymerase chain reaction (PCR).

Effective use of such markers in assisting in the diagnosis and identification of an effective therapeutic regimen has been impeded by the inability of current automated analysis systems to utilize and identify the varied markers in a cost efficient, time sensitive, and reproducible manner. Thus, previous techniques and systems have often proven inadequate for the efficient analysis of tissue samples requiring a rapid parallel analysis of a variety of independent microscopic, histologic and/or molecular characteristics.

In manual scoring applications, the time it takes to collect an image is small relative to the time a user might spend in searching for the image on a slide. In fluorescent microscopy a fluorescent signal is used to identify a cell or candidate object of interest. However, while fluorescent signals can typically be seen with the naked eye when looking through a microscope, video cameras for imaging fluorescent slides, such as FISH slides, suffer from the disadvantage that an image will take from a fraction of a second to several seconds to locate and collect. In contrast, a microscope using transmitted light the time difference between imaging a fluorescent image and imaging an image in transmitted light for an entire slide will be significant. For example, a system could image all parts of a slide in 6 minutes in transmitted light, whereas it might take an hour or more to image under fluorescent conditions.

In addition, another problem with current automated fluorescent systems is the continued need for operator input to initially locate cell objects for analysis. Such continued dependence on manual input can lead to errors including cells or objects of interest being missed. Such errors can be critical especially in assays for so-called rare events, e.g., finding one tumor cell in a cell population of one million normal cells.

Additionally, manual methods can be extremely time consuming and can require a high degree of training to identify and/or quantify cells. This is not only true for tumor cell identification and detection, but also for other applications ranging from neutrophil alkaline phosphatase assays, reticulocyte counting and maturation assessment, and others. The associated manual labor leads to a high cost for these procedures in addition to the potential errors that can arise from long, tedious manual examinations.

The invention provides an automated analysis system that quickly and accurately scans large amounts of biological material on a slide. In addition, the system automates the analysis of fluorescent images on a slide quickly and accurately. Accordingly, the invention provides useful methods, apparatus, and systems for use in research and patient diagnostics to locate cell objects for analysis having either or both of a non-fluorescent stain and a fluorescent indicator.

A biological sample and/or subsample comprises biological materials obtained from or derived from a living organism. Typically a biological sample will comprise proteins, polynucleotides, organic material, cells, tissue, and any combination of the foregoing. Such samples include, but are not limited to, hair, skin, tissue, cultured cells, cultured cell media, and biological fluids. A tissue is a mass of connected cells and/or extracellular matrix material (e.g., CNS tissue, neural tissue, eye tissue, placental tissue, mammary gland tissue, gastrointestinal tissue, musculoskeletal tissue, genitourinary tissue, and the like) derived from, for example, a human or other mammal and includes the connecting material and the liquid material in association with the cells and/or tissues. A biological fluid is a liquid material derived from, for example, a human or other mammal. Such biological fluids include, but are not limited to, blood, plasma, serum, serum derivatives, bile, phlegm, saliva, sweat, amniotic fluid, mammary fluid, and cerebrospinal fluid (CSF), such as lumbar or ventricular CSF. A sample also may be media containing cells or biological material.

In one aspect of the invention, a biological sample may be divided into two or more additional samples (e.g., subsamples). Typically, in such an instance, the biological sample is a tissue, such as a tissue biopsy. Typically, an individual sample used to prepare a subsample is embedded in embedding media such as paraffin or other waxes, gelatin, agar, polyethylene glycols, polyvinyl alcohol, celloidin, nitrocelluloses, methyl and butyl methacrylate resins or epoxy resins, which are polymerized after they infiltrate the specimen. Water-soluble embedding media such as polyvinyl alcohol, carbowax (polyethylene glycols), gelatin, and agar, may be used directly on specimens. Water-insoluble embedding media such as paraffin and nitrocellulose require that specimens be dehydrated in several changes of solvent such as ethyl alcohol, acetone, or isopropyl alcohol and then be immersed in a solvent in which the embedding medium is soluble. In the case where the embedding medium is paraffin, suitable solvents for the paraffin are xylene, toluene, benzene, petroleum, ether, chloroform, carbon tetrachloride, carbon bisulfide, and cedar oil. Typically a tissue sample is immersed in two or three baths of the paraffin solvent after the tissue is dehydrated and before the tissue sample is embedded in paraffin. Embedding medium includes, for examples, any synthetic or natural matrix suitable for embedding a sample in preparation for tissue sectioning.

A tissue sample may be a conventionally fixed tissue sample, tissue samples fixed in special fixatives, or may be an unfixed sample (e.g., freeze-dried tissue samples). If a tissue sample is freeze-dried, it should be snap-frozen. Fixation of a tissue sample can be accomplished by cutting the tissue specimens to a thickness that is easily penetrated by fixing fluid. Examples of fixing fluids are aldehyde fixatives such as formaldehyde, formalin or formol, glyoxal, glutaraldehyde, hydroxyadipaldehyde, crotonaldehyde, methacrolein, acetaldehyde, pyruic aldehyde, malonaldehyde, malialdehyde, and succinaldehyde; chloral hydrate; diethylpyrocarbonate; alcohols such as methanol and ethanol; acetone; lead fixatives such as basic lead acetates and lead citrate; mercuric salts such as mercuric chloride; formaldehyde sublimates; sublimate dichromate fluids; chromates and chromic acid; and picric acid. Heat may also be used to fix tissue specimens by boiling the specimens in physiologic sodium chloride solution or distilled water for two to three minutes. Whichever fixation method is ultimately employed, the cellular structures of the tissue sample must be sufficiently hardened before they are embedded in a medium such as paraffin.

Using techniques such as those disclosed herein, a biological sample comprising a tissue may be embedded, sectioned, and fixed, whereby a single biopsy can render a plurality of subsamples upon sectioning. As discussed below, such subsamples can be examined under different staining or fluorescent conditions thereby rendering a wealth of information about the tissue biopsy. In one aspect of the invention, an array of tissue samples may be prepared and located on a single slide. The generation of such tissue-microarrays are known in the art. Each tissue sample in the tissue-microarray may be stained and/or treated the same of differently using both automated techniques and manual techniques (see, e.g., Kononen et al. Nature Medicine, 4(7), 1998; and U.S. Pat. No. 6,103,518, the disclosures of which are incorporated herein by reference).

In another aspect, the invention provides a method whereby a single biological sample may be assayed or examined in many different ways. Under such conditions a sample may be stained or labeled with a first agent and examined by light microscopy with transmitted light and/or a combination of light microscopy and fluorescent microscopy. The sample is then stained or labeled with a second agent and examined by light microscopy (e.g., transmitted light) and/or a combination of light microscopy and fluorescent microscopy.

The invention provides methods of automated analysis of a biological sample. The biological sample and/or subsample can be contacted with a variety of agents useful in determining and analyzing cellular molecules and mechanisms. Such agents include, for example, polynucleotides, polypeptides, small molecules, and/or antibodies useful in in situ screening assays for detecting molecules that specifically bind to a marker present in a sample. Such assays can be used to detect, prognoses, diagnose, or monitor various conditions, diseases, and disorders, or monitor the treatment thereof. An agent can be detectably labeled such that the agent is detectable when bound or hybridized to its target marker or ligand. Such means for detectably labeling any of the foregoing agents include an enzymatic, fluorescent, or radionuclide label. Other reporter means and labels are well known in the art.

A marker can be any cell component present in a sample that is identifiable by known microscopic, histologic, or molecular biology techniques. Markers can be used, for example, to distinguish neoplastic tissue from non-neoplastic tissue. Such markers can also be used to identify a molecular basis of a disease or disorder including a neoplastic disease or disorder. Such a marker can be, for example, a molecule present on a cell surface, an overexpressed target protein, a nucleic acid mutation or a morphological characteristic of a cell present in a sample.

An agent useful in the methods of the invention can be an antibody. Antibodies useful in the methods of the invention include intact polyclonal or monoclonal antibodies, as well as fragments thereof, such as Fab and F(ab')2. For example, monoclonal antibodies are made from antigen containing fragments of a protein by methods well known to those skilled in the art (Kohler, et al., Nature, 256:495, 1975). Fluorescent molecules may be bound to an immunoglobulin either directly or indirectly by using an intermediate functional group.

An agent useful in the methods of the invention can also be a nucleic acid molecule (e.g., an oligonucleotide or polynucleotide). For example, in situ nucleic acid hybridization techniques are well known in the art and can be used to identify an RNA or DNA marker present in a sample or subsample. Screening procedures that rely on nucleic acid hybridization make it possible to identify a marker from any sample, provided the appropriate oligonucleotide or polynucleotide agent is available. For example, oligonucleotide agents, which can correspond to a part of a sequence encoding a target polypeptide (e.g., a cancer marker comprising a polypeptide), can be synthesized chemically or designed through molecular biology techniques. The polynucleotide encoding the target polypeptide can be deduced from the genetic code, however, the degeneracy of the code must be taken into account. For such screening, hybridization is typically performed under in situ conditions known to those skilled in the art.

Figure 2:
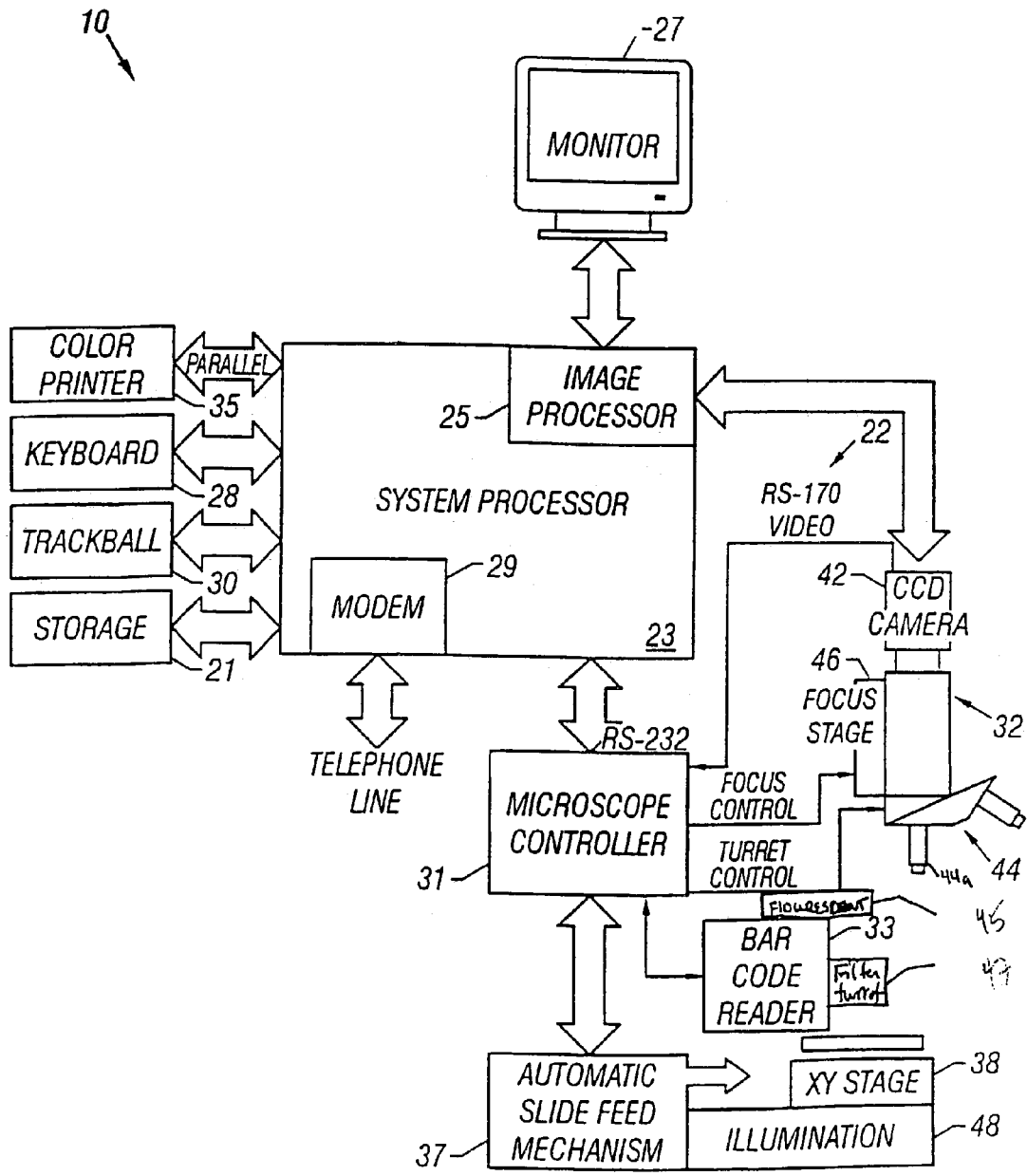
FIG. 2 is a block diagram of the apparatus shown in FIG. 1.

Referring now to FIGS. 1 and 2, an apparatus for automated cell analysis of biological samples is generally indicated by reference numeral 10 as shown in perspective view in FIG. 1 and in block diagram form in FIG. 2. The apparatus 10 comprises a microscope subsystem 32 housed in a housing 12. The housing 12 includes a slide carrier input hopper 16 and a slide carrier output hopper 18. A door 14 in the housing 12 secures the microscope subsystem from the external environment. A computer subsystem comprises a computer 22 having at least one system processor 23, and a communications modem 29. The computer subsystem further includes a computer/image monitor 27 and other external peripherals including storage device 21, a pointing device, such as a track ball or mouse device 30, a user input device, such as a touch screen, keyboard, or voice recognition unit 28 and color printer 35. An external power supply 24 is also shown for power outage protection. The apparatus 10 further includes an optical sensing array 42, such as, for example, a CCD camera, for acquiring images. Microscope movements are under the control of system processor 23 through a number of microscope-subsystem functions described further in detail. An automatic slide feed mechanism in conjunction with X-Y stage 38 provide automatic slide handling in the apparatus 10. An illumination 48 comprising a bright field transmitted light source projects light onto a sample on the X-Y stage 38, which is subsequently imaged through the microscope subsystem 32 and acquired through optical sensing array 42 for processing by the system processor 23. A Z stage or focus stage 46 under control of the system processor 23 provides displacement of the microscope subsystem in the Z plane for focusing. The microscope subsystem 32 further includes a motorized objective turret 44 for selection of objectives.

The apparatus 10 further includes a fluorescent excitation light source 45 and may further include a plurality of fluorescent filters on a turret or wheel 47. Alternatively, a filter wheel may have an electronically tunable filter. In one aspect, fluorescent excitation light from fluorescent excitation light source 45 passes through fluorescent filter 47 and proceeds to contact a sample on the XY stage 38. Fluorescent emission light emitted from a fluorescent agent contained on a sample passes through objective 44a to optical sensing array 42. The fluorescent emission light forms an image, which is digitized by an optical sensing array 42, and the digitized image is sent to an image processor 25 for subsequent processing.

The purpose of the apparatus 10 is for the automatic scanning of prepared microscope slides for the detection of candidate objects of interest such as normal and abnormal cells, e.g., tumor cells. In one aspect, the apparatus 10 is capable of detecting rare events, e.g., event in which there may be only one candidate object of interest per several hundred thousand objects, e.g., one to five candidate objects of interest per 2 square centimeter area of the slide. The apparatus 10 automatically locates and can count candidate objects of interest noting the coordinates or location of the candidate object of interest on a slide based upon color, size and shape characteristics. A number of stains can be used to stain candidate objects of interest and other objects (e.g., normal cells) different colors so that such cells can be distinguished from each other (as described herein).

Figure 8:
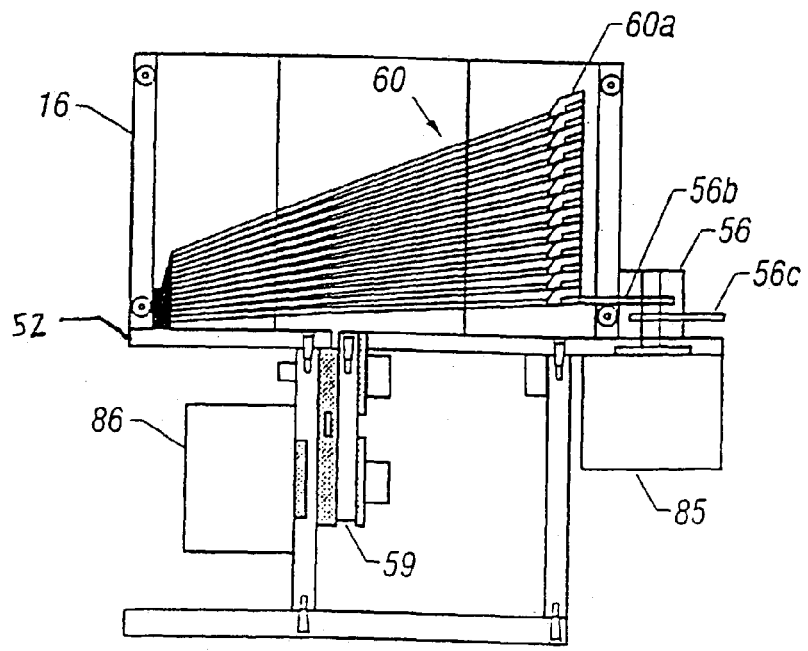
FIG. 8 is an end view of the input module of the automated slide handling subsystem.
Figure 8A:
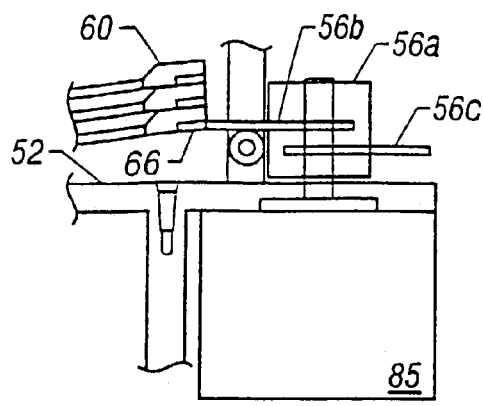
FIGS. 8a-8d illustrate the input operation of the automatic slide handling subsystem.
Figure 8B:
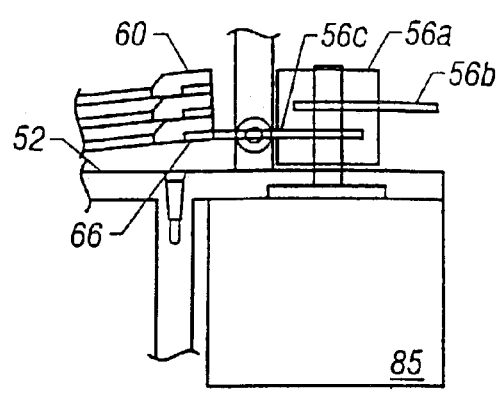

A biological sample may be prepared with a reagent to obtain a colored insoluble precipitate. As one step in the methods and systems of the invention an apparatus 10 is used to detect this precipitate as a candidate object of interest. During operation of the apparatus 10, a pathologist or laboratory technician mounts slides onto slide carriers. Each slide may contain a single sample or a plurality of samples (e.g., a tissue microarray). A slide carrier 60 is illustrated in FIG. 8 and will be described further below. Each slide carrier can be designed to hold a number of slides from about 1-50 or more (e.g., the holder depicted in FIG. 8 holds up to 4 slides). A number of slide carriers are then loaded into input hopper 16 (see FIG. 1). The operator can specify the size, shape and location of the area to be scanned or alternatively, the system can automatically locate an area. The operator then commands the system to begin automated scanning of the slides through a graphical user interface. Unattended scanning begins with the automatic loading of the first carrier and slide onto the precision motorized X-Y stage 38. In one aspect of the invention, a bar code label affixed to the slide or slide carrier is read by a bar code reader 33 during this loading operation. Each slide is then scanned a desired magnification, for example, 10×, to identify candidate cells or objects of interest based on their color, size and shape characteristics. The term "coordinate" or "address" is used to mean a particular location on a slide or sample. The coordinate or address can be identified by any number of means including, for example, X-Y coordinates, r-θ coordinates, polar, vector or other coordinate systems known in the art. In one aspect of the invention a slide is scanned under a first parameter comprising a desired magnification and using a bright field light source from illumination 48 (see FIG. 2) to identify a candidate cell or object of interest.

The methods, systems, and apparatus of the invention may obtain a low magnification image of a candidate cell or object of interest and then return to each candidate cell or object of interest based upon the previously stored coordinates to reimage and refocus at a higher magnification such as 40× or to reimage under fluorescent conditions. To avoid missing candidate cells or objects of interest, the system can process low magnification images by reconstructing the image from individual fields of view and then determine objects of interest. In this manner, objects of interest that overlap more than one objective field of view may be identified. The apparatus comprises a storage device 21 that can be used to store an image of a candidate cell or object of interest for later review by a pathologist or to store identified coordinates for later use in processing the sample or a subsample. The storage device 21 can be a removable hard drive, DAT tape, local hard drive, optical disk, or may be an external storage system whereby the data is transmitted to a remote site for review or storage. In one aspect, stored images (from both fluorescent and bright field light) can be overlapped and viewed in a mosaic of images for further review (as discussed more fully herein).

Apparatus 10 is also used for fluorescent imaging (e.g., in FISH techniques) of prepared microscope slides for the detection of candidate objects of interest such as normal and abnormal cells, e.g., tumor cells. The apparatus 10 automatically locates the coordinates of previously identified candidate cells or objects of interest based upon the techniques described above. In this aspect, the slide has been contacted with a fluorescent agent labeled with a fluorescent indicator. The fluorescent agent is an antibody, polypeptide, oligonucleotide, or polynucleotide labeled with a fluorescent indicator. A number of fluorescent indicators are known in the art and include DAPI, Cy3, Cy3.5, Cy5, CyS.5, Cy7, umbelliferone, fluorescein, fluorescein isothiocyanate (FITC), rhodamine, dichlorotriazinylamine fluorescein, dansyl chloride or phycoerythrin. In another aspect of the invention a luminescent material may be used. Useful luminescent materials include luminol; examples of bioluminescent materials include luciferase, luciferin, and aequorin.

A fluorescent indicator should have distinguishable excitation and emission spectra. Where two or more fluorescent indicators are used they should have differing excitation and emission spectra that differ, respectively, by some minimal value (typically about 15-30 nm). The degree of difference will typically be determined by the types of filters being used in the process. Typical excitation and emission spectra for DAPI, FITC, Cy3, Cy3.5, Cy5, CyS.5, and Cy7 are provided below:

| Fluorescent indicator | Excitation Peak | Emission Peak |
|---|---|---|
| DAPI | 350 | 450 |
| FITC | 490 | 520 |
| Cy3 | 550 | 570 |
| Cy3.5 | 580 | 595 |
| Cy5 | 650 | 670 |
| Cy5.5 | 680 | 700 |
| Cy7 | 755 | 780 |

A biological sample is prepared with a fluorescently labeled agent or luminescently labeled agent to identify molecules of interest within the biological sample. An apparatus of the invention is used to detect the fluorescence or luminescence of the molecule when exposed to a wavelength that excites a fluorescent indicator attached to the fluorescent agent or exposed to conditions that allow for luminescence. The automated system of the invention scans a biological sample contacted with a fluorescently agent under conditions such that a fluorescent indicator attached to the agent fluoresces, or scans a biological sample labeled with a luminescent agent under conditions that detects light emissions from a luminescent indicator. Examples of conditions include providing a fluorescent excitation light that contacts and excites the fluorescent indicator to fluoresce. As described in more detail herein the apparatus of the invention includes a fluorescent excitation light source and can also include a number of fluorescent excitation filters to provide different wavelengths of excitation light. In one aspect of the invention, a bar code label affixed to a slide or slide carrier is read by a bar code reader 33 during a loading operation. The bar code provides the system with information including, for example, information about the scanning parameters including the type of light source or the excitation light wavelength to use. Each slide is then scanned at a desired magnification, for example, 10×, to identify candidate cells or objects of interest based on their color, size, and shape characteristics. Where the location of candidate cells or objects of interest have been previously identified, the location, coordinate, or address of the candidate cells or objects of interest (including corrected coordinates where more than one subsample is analyzed) are used to focus the system at those specific locations and obtain fluorescent or bioluminescent images.

The methods, system, and apparatus of the invention can obtain a first image using a transmitted light source at either a low magnification or high magnification of a candidate cell or object of interest and then return to the coordinates (or corrected coordinates) associated with each candidate cell or object of interest in the same sample or a related subsample to obtain a fluorescent image. Fluorescent images or luminescent images can be stored on a storage device 21 that can be used to store an image of a candidate cell or object of interest for later review by a pathologist. The storage device 21 can be a removable hard drive, DAT tape, local hard drive, optical disk, or may be an external storage system whereby the data is transmitted to a remote site for review or storage. In one aspect, stored images (from both fluorescent and bright field light) can be overlapped and viewed in a mosaic of images for further review (as discussed more fully herein).

Where transmitted light microscopy or fluorescent light microscopy are followed sequentially in either order the light sources for both processes must be managed. Such light source management is performed using the system processor 23 through the Fluorescent controller 102 and illumination controller 106 (see, FIG. 3). During processing of images in transmitted light microscopy the fluorescent excitation light source is off or blocked such that excitation light from the fluorescent light source does not contact the sample. When fluorescent images are being obtained the transmitted light source is off or blocked such that the transmitted light does not pass through the sample while the sample is contacted by fluorescent excitation light from fluorescent excitation light source 45.

Figure 3:
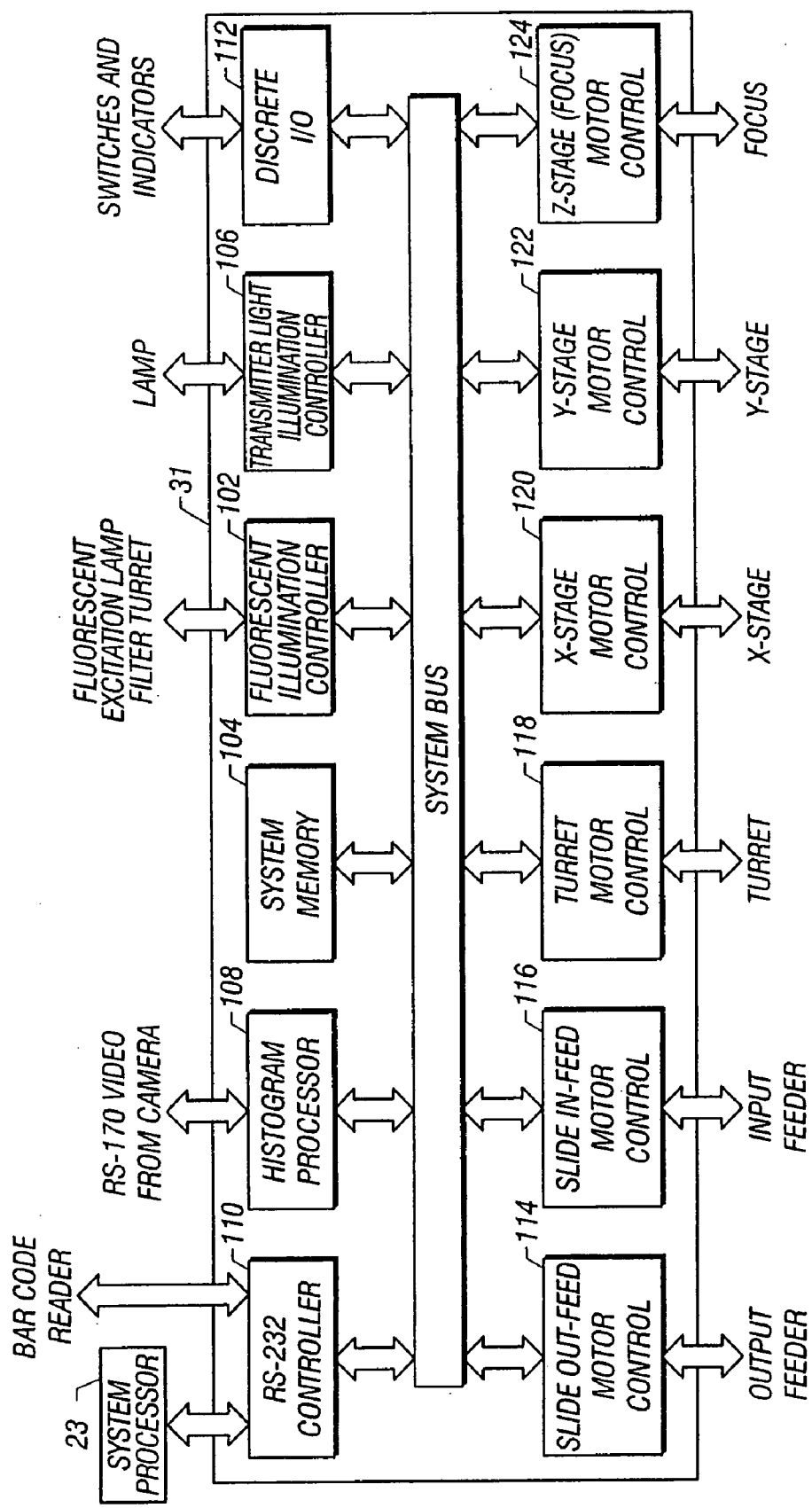
FIG. 3 is a block diagram of the system processor of FIG. 2.

Having described the overall operation of the apparatus 10 from a high level, the further details of the apparatus will now be described. Referring to FIG. 3, the microscope controller 31 is shown in more detail. The microscope controller 31 includes a number of subsystems. The apparatus system processor 23 controls these subsystems. The system processor 23 controls a set of motor—control subsystems 114 through 124, which control the input and output feeder, the motorized turret 44, the X-Y stage 38, and the Z stage 46 (FIG. 2). The system processor 23 further controls a transmitted light illumination controller 106 for control of substage illumination 48 bright field transmitted light source and controls a fluorescent excitation illumination controller 102 for control of fluorescent excitation light source 45 and/or filter turret 47. The transmitted light illumination controller 106 is used in conjunction with camera and image collection adjustments to compensate for the variations in light level in various samples. The light control software samples the output from the camera at intervals (such as between loading of slide carriers), and commands the transmitted light illumination controller 106 to adjust the light or image collection functions to the desired levels. In this way, light control is automatic and transparent to the user and adds no additional time to system operation. Similarly, fluorescent excitation illumination controller 102 is used in conjunction with the camera and image collection adjustments to compensate for the variations in fluorescence in various samples. The light control software samples the output from the camera at intervals (such as between loading of slide carriers and may include sampling during image collection), and commands the fluorescent excitation illumination controller 102 to adjust the fluorescent excitation light or image exposure time to a desired level. In addition, the fluorescent excitation illumination controller 102 may control the filter wheel or wavelength 47. The system processor 23 is a high performance processor of at least 200 MHz, for example, the system processor may comprise dual parallel, Intel, 1 GHZ devices. Advances in processors are being routinely made in the computer industry. Accordingly, the invention should not be limited by the type of processor or speed of the processor disclosed herein.

Figure 4:
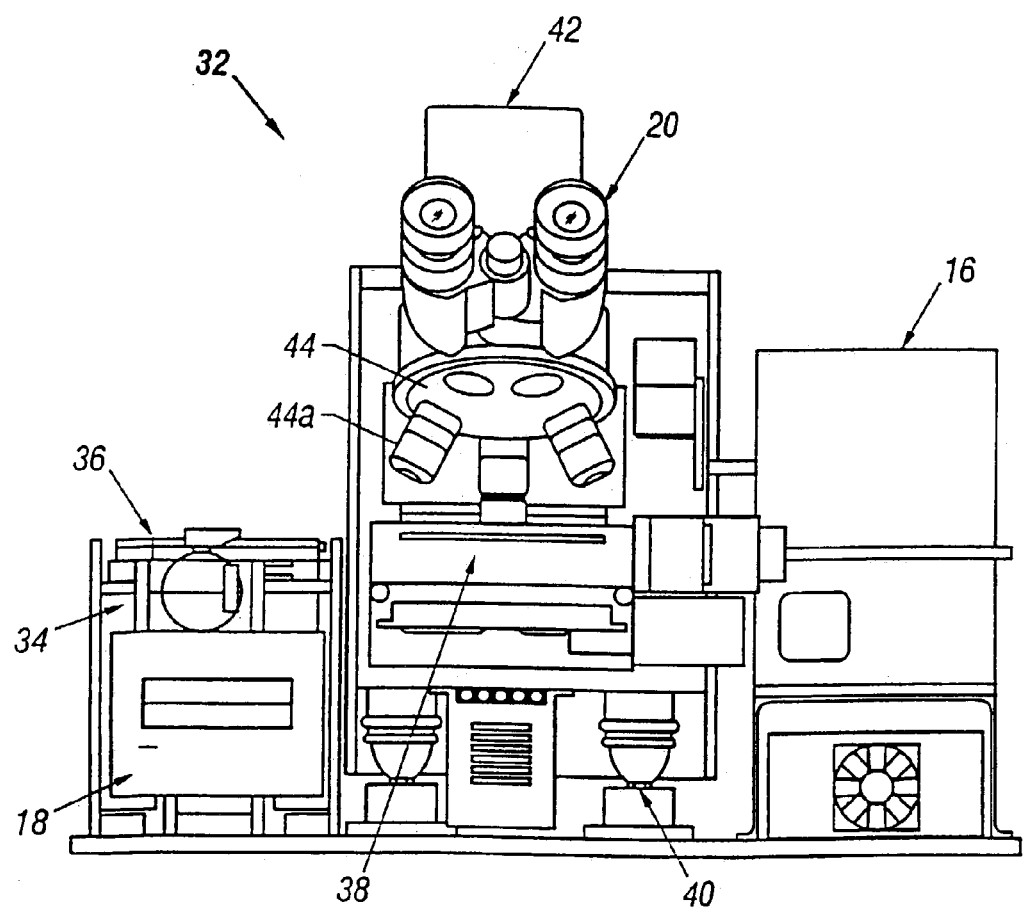
FIG. 4 is a plan view of the apparatus of FIG. 1 having the housing removed.
Figure 5:
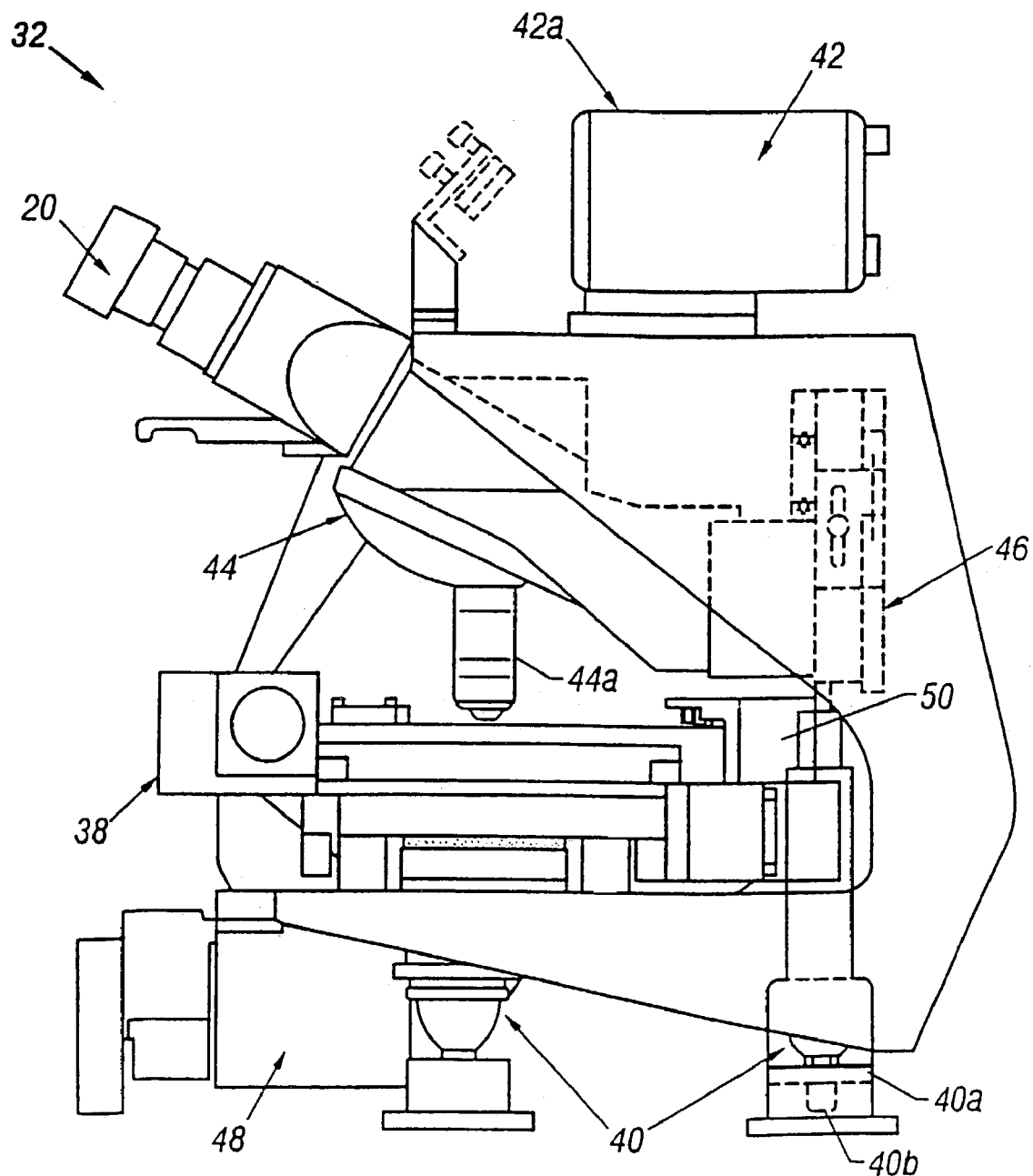
FIG. 5 is a side view of a microscope subsystem of the apparatus of FIG. 1.

Referring now to FIGS. 4 and 5, further detail of the apparatus 10 is shown. FIG. 4 shows a plan view of the apparatus 10 with the housing 12 removed. Shown is slide carrier unloading assembly 34 and unloading platform 36 which in conjunction with slide carrier output hopper 18 function to receive slide carriers which have been analyzed. Vibration isolation mounts 40, shown in further detail in FIG. 5, are provided to isolate the microscope subsystem 32 from mechanical shock and vibration that can occur in a typical laboratory environment. In addition to external sources of vibration, the high-speed operation of the X-Y stage 38 can induce vibration into the microscope subsystem 32. Such sources of vibration can be isolated from the electro-optical subsystems to avoid any undesirable effects on image quality. The isolation mounts 40 comprise a spring 40a and piston 40b (see FIG. 5) submerged in a high viscosity silicon gel which is enclosed in an elastomer membrane bonded to a casing to achieve damping factors on the order of about 17 to 20%. Other dampening devices are known in the art and may be substituted or combined with the dampening device provided herein. Occulars 20 are shown in FIGS. 4 and 5, however, their presence is an optional feature. The occulars 20 may be absent without departing from the advantages or functionality of the system.

Figure 6A:
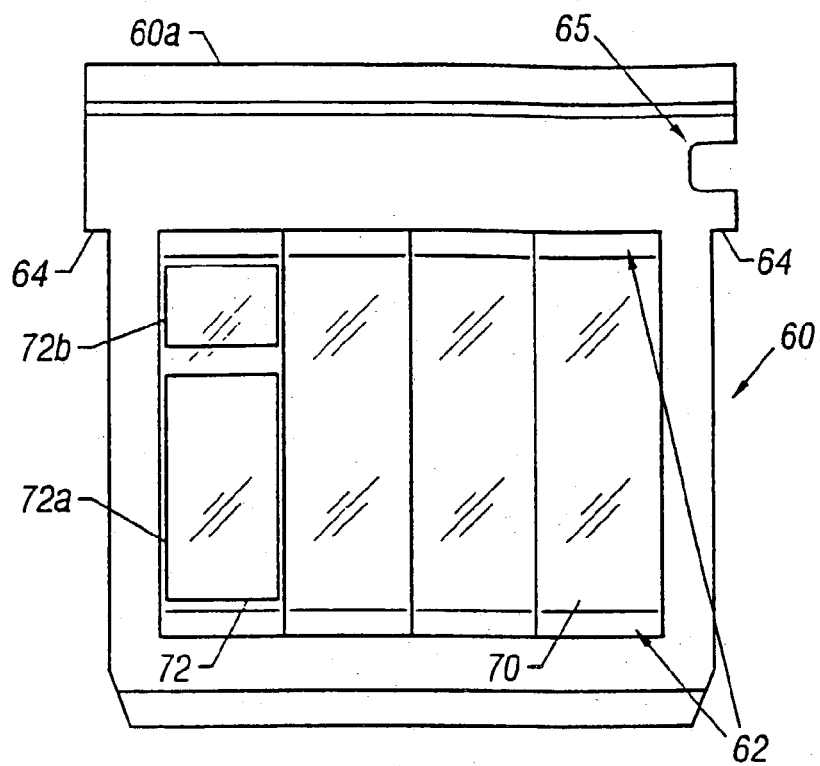
FIG. 6a is a top view of a slide carrier for use with the apparatus of FIG. 1.
Figure 6B:
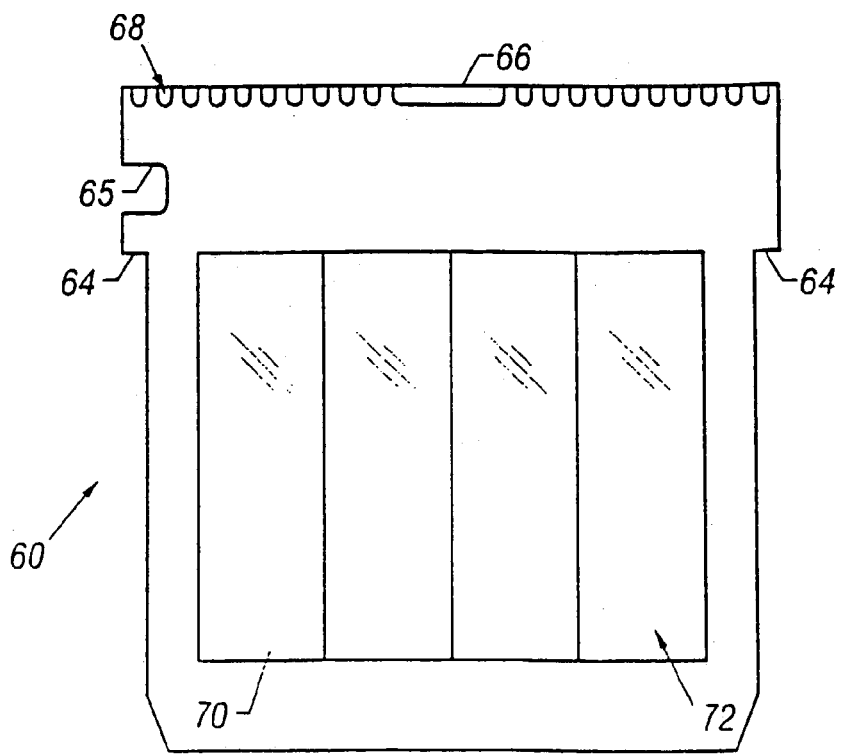

The automatic slide-handling feature of the invention will now be described. The automated slide handling subsystem operates the movement and management of a slide carrier. A slide carrier 60 is shown in FIGS. 6a and 6b, which provide a top view and a bottom view, respectively. The slide carrier 60 can include a number of slides 70 (e.g., at least four slides but may number from 1-50 or more). The carrier 60 includes ears 64 for hanging the carrier in the output hopper 18. An undercut 66 and pitch rack 68 are formed at the top edge of the slide carrier 60 for mechanical handling of the slide carrier. A keyway cutout 65 is formed in one side of the carrier 60 to facilitate carrier alignment. A prepared slide 72 mounted on the slide carrier 60 includes a sample area 72a and a bar code label area 72b.

Figure 7A:
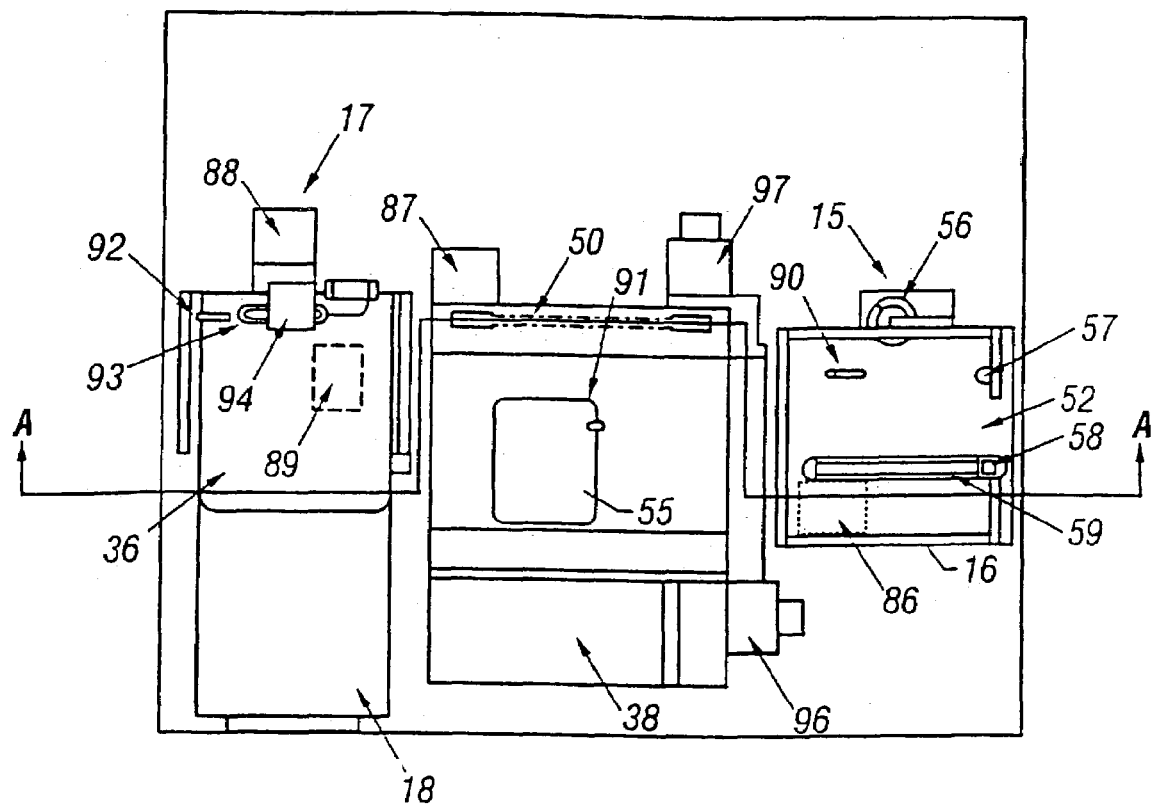
FIG. 7a is a top view of an automated slide handling subsystem of the apparatus of FIG. 1.
Figure 7B:
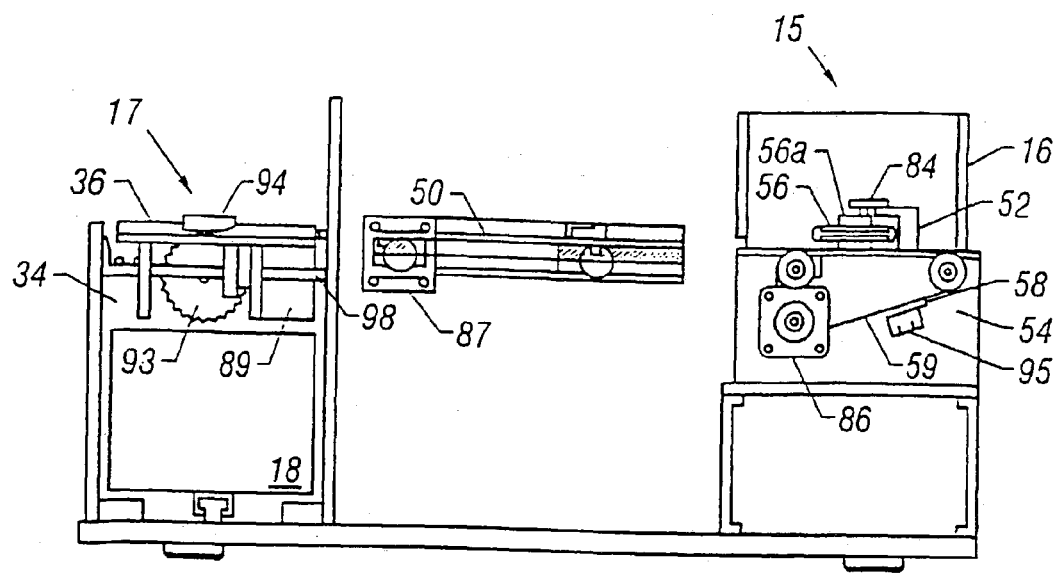
FIG. 7b is a partial cross-sectional view of the automated slide handling subsystem of FIG. 7a taken on line A-A.

FIG. 7a provides a top view of the slide handling subsystem, which comprises a slide, input module 15, a slide output module 17 and X-Y stage drive belt 50. FIG. 7b provides a partial cross-sectional view taken along line A-A of FIG. 7a. The slide input module 15 comprises a slide carrier input hopper 16, loading platform 52 and slide carrier loading subassembly 54. The input hopper 16 receives a series of slide carriers 60 (FIGS. 6a and 6b) in a stack on loading platform 52. A guide key 57 (see FIG. 7a) protrudes from a side of the input hopper 16 to which the keyway cutout 65 (FIG. 6a) of the carrier is fit to achieve proper alignment. The input module 15 further includes a revolving indexing cam 56 and a switch 90 (FIG. 7a) mounted in the loading platform 52, the operation of which is described further below. The carrier loading subassembly 54 comprises an infeed drive belt 59 driven by a motor 86. The infeed drive belt 59 includes a pusher tab 58 for pushing the slide carrier horizontally toward the X-Y stage 38 when the belt is driven. A homing switch 95 senses the pusher tab 58 during a revolution of the belt 59. Referring specifically to FIG. 7a, the X-Y stage 38 is shown with x position and y position motors 96 and 97, respectively, which are controlled by the system processor 23 (FIG. 3) and are not considered part of the slide handling subsystem. The X-Y stage 38 further includes an aperture 55 for allowing illumination to reach the slide carrier. A switch 91 is mounted adjacent the aperture 55 for sensing contact with the carrier and thereupon activating a motor 87 to drive stage drive belt 50 (FIG. 7b). The drive belt 50 is a double-sided timing belt having teeth for engaging pitch rack 68 of the carrier 60 (FIG. 6b).

The slide output module 17 includes slide carrier output hopper 18, unloading platform 36 and slide carrier unloading subassembly 34. The unloading subassembly 34 comprises a motor 89 for rotating the unloading platform 36 about shaft 98 during an unloading operation described further below. An outfeed gear 93 driven by motor 88 (FIG. 7a) rotatably engages the pitch rack 68 of the carrier 60 (FIG. 6b) to transport the carrier to a rest position against switch 92 (FIG. 7a). A springloaded hold-down mechanism 94 holds the carrier in place on the unloading platform 36.

The slide handling operation will now be described. Referring to FIG. 8, a series of slide carriers 60 are shown stacked in input hopper 16 with the top edges 60a aligned. As the slide handling operation begins, the indexing cam 56 driven by motor 85 advances one revolution to allow only one slide carrier to drop to the bottom of the hopper 16 and onto the loading platform 52.

Figure 8C:
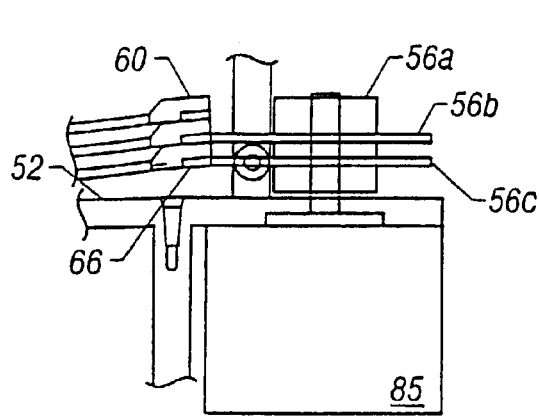
Figure 8D:
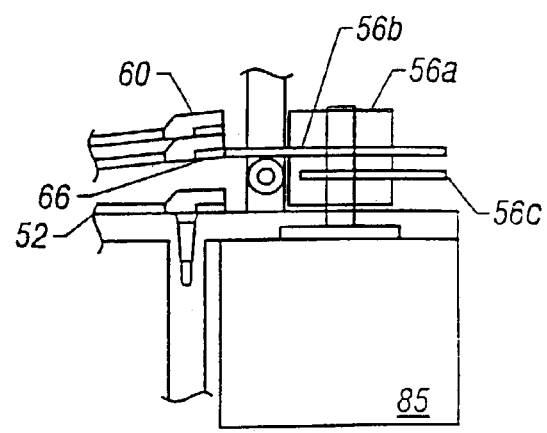

FIGS. 8a-8d show the cam action in more detail. The cam 56 includes a hub 56a to which are mounted upper and lower leaves 56b and 56c, respectively. The leaves 56b and 56c are semicircular projections oppositely positioned and spaced apart vertically. In a first position shown in FIG. 8a, the upper leaf 56b supports the bottom carrier at the undercut portion 66. At a position of the cam 56 rotated 180°, shown in FIG. 8b, the upper leaf 56b no longer supports the carrier and instead the carrier has dropped slightly and is supported by the lower leaf 56c. FIG. 8c shows the position of the cam 56 rotated 270° wherein the upper leaf 56b has rotated sufficiently to begin to engage the undercut 66 of the next slide carrier while the opposite facing lower leaf 56c still supports the bottom carrier. After a full rotation of 360° as shown in FIG. 8d, the lower leaf 56c has rotated opposite the carrier stack and no longer supports the bottom carrier which now rests on the loading platform 52. At the same position, the upper leaf 56b supports the next carrier for repeating the cycle.

Referring again to FIGS. 7a and 7b, when the carrier drops to the loading platform 52, the contact closes switch 90, which activates motors 86 and 87. Motor 86 drives the infeed drive belt 59 until the pusher tab 58 makes contact with the carrier and pushes the carrier onto the X-Y stage drive belt 50. The stage drive belt 50 advances the carrier until contact is made with switch 91, the closing of which begins the slide scanning process described further herein.

Upon completion of the scanning process, the X-Y stage 38 moves to an unload position and motors 87 and 88 are activated to transport the carrier to the unloading platform 36 using stage drive belt 50. As noted, motor 88 drives outfeed gear 93 to engage the pitch rack 68 of the carrier 60 (FIG. 6b) until switch 92 is contacted. Closing switch 92 activates motor 89 to rotate the unloading platform 36.

The unloading operation is shown in more detail in end views of the output module 17 (FIGS. 9a-9d). In FIG. 9a, the unloading platform 36 is shown in a horizontal position supporting a slide carrier 60. The hold-down mechanism 94 secures the carrier 60 at one end. FIG. 9b shows the output module 17 after motor 89 has rotated the unloading platform 36 to a vertical position, at which point the spring loaded hold-down mechanism 94 releases the slide carrier 60 into the output hopper 18. The carrier 60 is supported in the output hopper 18 by means of ears 64 (FIGS. 6a and 6b). FIG. 9c shows the unloading platform 36 being rotated back towards the 20 horizontal position. As the platform 36 rotates upward, it contacts the deposited carrier 60 and the upward movement pushes the carrier toward the front of the output hopper 18. FIG. 9*d* shows the unloading platform 36 at its original horizontal position after having output a series of slide carriers 60 to the output hopper 18.

Having described the overall system and the automated slide handling feature, the aspects of the apparatus 10 relating to scanning, focusing and image processing will now be described in further detail.

Figure 10:
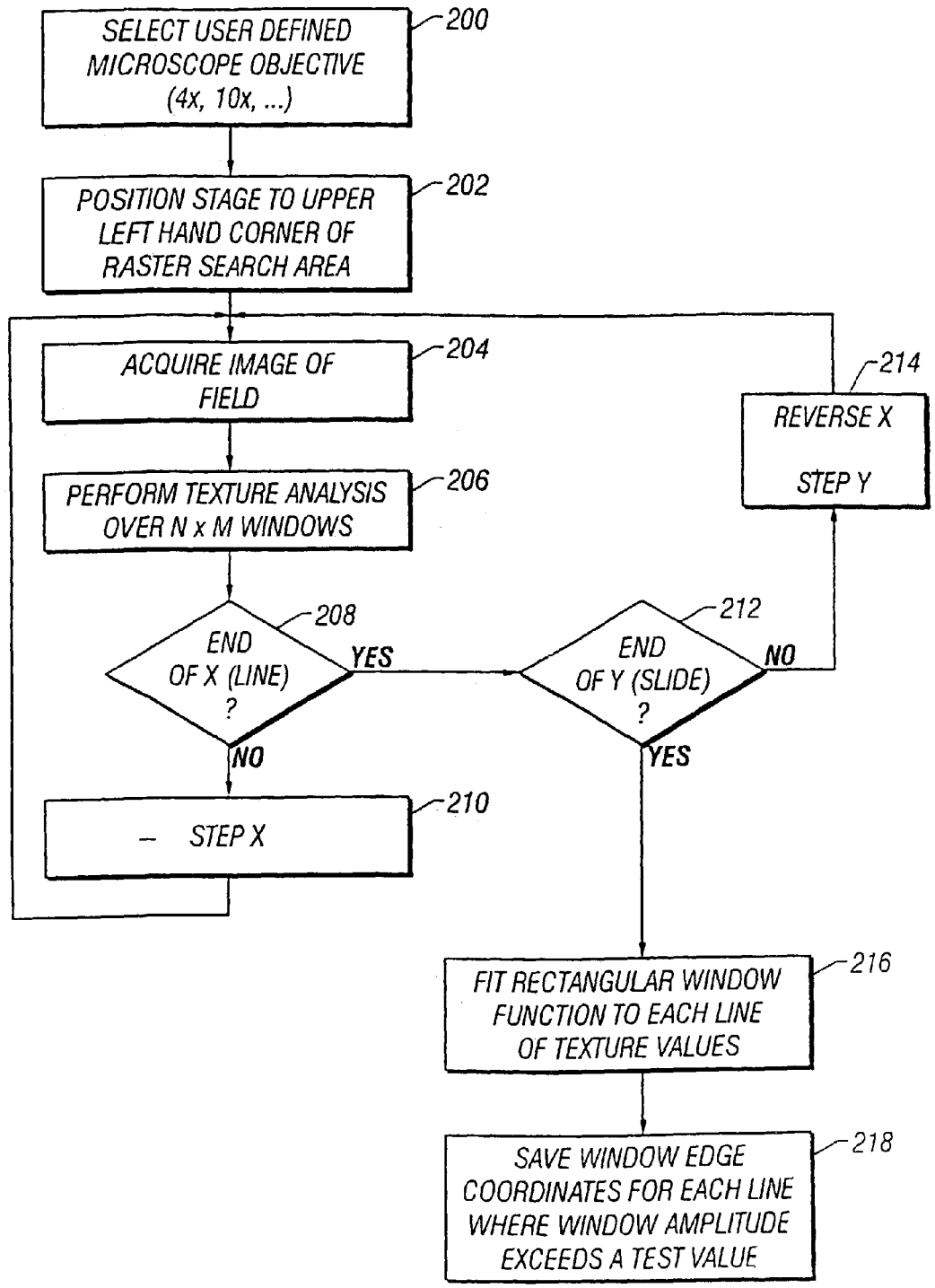
FIG. 10 is a flow diagram of the procedure for automatically determining a scan area.

In some cases, an operator will know ahead of time where the scan area of interest is on a slide comprising a sample. Conventional preparation of slides for examination provides repeatable and known placement of the sample on the slide. The operator can therefore instruct the system to always scan the same area at the same location of every slide, which is prepared in this fashion. But there are other times in which the area of interest is not known, for example, where slides are prepared manually with a smear technique. One feature of the invention automatically determines the scan area using a texture or density analysis process. FIG. 10 is a flow diagram that describes the processing associated with the automatic location of a scan area. As shown in this flow diagram, a basic method is to pre-scan the entire slide area under transmitted light to determine texture features that indicate the presence of a smear or tissue and to discriminate these areas from dirt and other artifacts. In addition, one or more distinctive features may be identified and the coordinates determined in order to make corrections to identify objects of interest in a serial subsample as described herein and using techniques known in the art.

Figure 12:
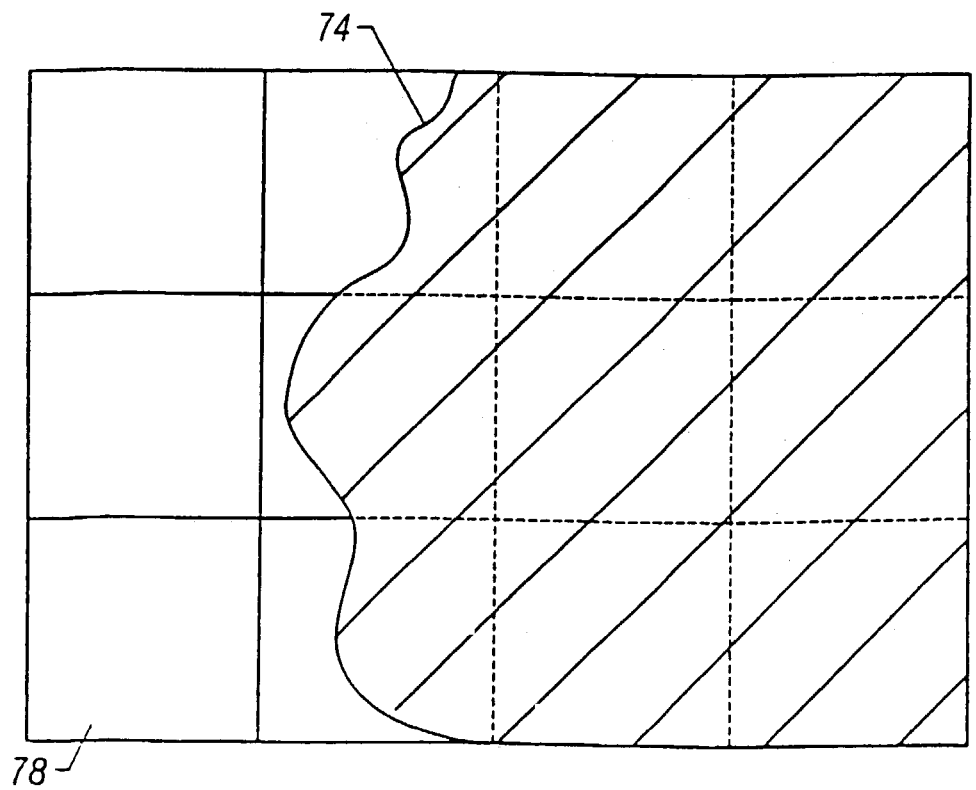
FIG. 12 illustrates an image of a field acquired in the procedure of FIG. 10.

As a first step the system determines whether a user defined microscope objective has been identified 200. The system then sets the stage comprising the sample to be scanned at a predetermined position, such as the upper left hand corner of a raster search area 202. At each location of a raster scan, an image such as in FIG. 12 is acquired 204 and analyzed for texture/border information 206. Since it is desired to locate the edges of the smear or tissue sample within a given image, texture analyses are conducted over areas called windows 78 (FIG. 12), which are smaller than the entire image as shown in FIG. 12. The process iterates the scan across the slide at steps 208, 210, 212, and 214.

Figure 11:
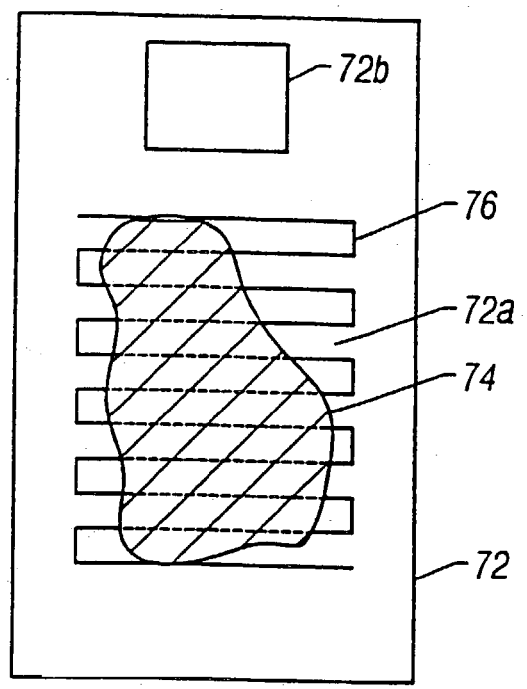
FIG. 11 shows the scan path on a prepared slide in the procedure of FIG. 10.

The texture analysis process can be performed at a lower magnification, such as at a 4× objective, for a rapid analysis. One reason to operate at low magnification is to image the largest slide area at any one time. Since cells do not yet need to be resolved at this stage of the overall image analysis, the 4× magnification works well. Alternatively, a higher magnification scan can be performed, which may take additional time due to the field of view being smaller and requiring additional images to be processed. On a typical slide, as shown in FIG. 11, a portion 72*b* of the end of the slide 72 is reserved for labeling with identification information. Excepting this label area, the entire slide is scanned in a raster scan fashion to yield a number of adjacent images. Texture values for each window include the pixel variance over a window, the difference between the largest and smallest pixel value within a window, and other indicators. The presence of a smear or tissue raises the texture values compared with a blank area.

One problem with a smear or tissue, from the standpoint of determining its location, is its non-uniform thickness and texture. For example, the smear or tissue is likely to be relatively thin at the edges and thicker towards the middle due to the nature of the smearing process. To accommodate this non-uniformity, texture analysis provides a texture value for each analyzed area. The texture value tends to gradually rise as the scan proceeds across a smear tissue from a thin area to a thick area, reaches a peak, and then falls off again to a lower value as a thin area at the edge is reached. The problem is then to decide from the series of texture values the beginning and ending, or the edges, of the smear or tissue. The texture values are fit to a square wave waveform since the texture data does not have sharp beginnings and endings.

After conducting this scanning and texture evaluation operation, one must determine which areas of elevated texture values represent the desired smear or tissue 74 (see FIG. 11), and which represent undesired artifacts. This is accomplished by fitting a step function, on a line-by-line basis, to the texture values in step 216 (see FIG. 10). This function, which resembles a single square wave beginning at one edge and ending at the other edge and having an amplitude, provides the means for discrimination. The amplitude of the best-fit step function is utilized to determine whether smear (tissue) or dirt is present since relatively high values indicate smear (tissue). If it is decided that smear (tissue) is present, the beginning and ending coordinates of this pattern are noted until all lines have been processed, and the smear (tissue) sample area defined at 218.

The first past scan above can be used to determine a particular orientation of a sample. For example, digital images are comprised of a series of pixels arranged in a matrix, a grayscale value is can be attributed to each pixel to indicate the appearance thereof of the image. "Orientation matching" between two samples (e.g., two serial sections stained with different agents) is then performed by comparing these grayscale values relative to their positions in both the first sample image (i.e., the template) and the second sample image. A match is found when the same or similar pattern is found in the second image when compared to the first image. Such systems are typically implemented in a computer for use in various manufacturing and robotic applications and are applicable to the methods and systems of the invention. For example, such systems have been utilized to automate tasks such as semiconductor wafer handling operations, fiducial recognition for pick-and-place printed circuit board (PCB) assembly, machine vision for quantification or system control to assist in location of objects on conveyor belts, pallets, and trays, and automated recognition of printed matter to be inspected, such as alignment marks. The matrix of pixels used to represent such digital images are typically arranged in a Cartesian coordinate system or other arrangement of non-rectangular pixels, such as hexagonal or diamond shaped pixels. Recognition methods usually require scanning the search image scene pixel by pixel in comparison with the template, which is sought. Further, known search techniques allow for transformations such as rotation and scaling of the template image within the second sample image, therefore requiring the recognition method to accommodate for such transformations.

Normalized grayscale correlation (NGC) has been used to match digital images reliably and accurately, as is disclosed in U.S. Pat. No. 5,602,937, entitled "Methods and Apparatus for Machine Vision High Accuracy Searching," assigned to Cognex Corporation. In addition, such software is available commercially through the Matrox Imaging Library version 7.5 (Matrox Electronic Systems Ltd., Canada).

After an initial focusing operation described further herein, the scan area of interest is scanned to acquire images for image analysis. In one aspect, a bar code or computer readable label placed at 72*b* (see FIG. 11) comprises instructions regarding the processing parameters of a particular slide as well as additional information such as a subject's name/initials or other identification. Depending upon the type of scan to be performed (e.g., fluorescence or transmitted light) a complete scan of the slide at low magnification is made to identify and locate candidate objects of interest, followed by further image analysis of the candidate objects of interest at high magnification in order to confirm the candidate cells or objects of interest. An alternate method of operation is to perform high magnification image analysis of each candidate object of interest immediately after the object has been identified at low magnification. The low magnification scanning then resumes, searching for additional candidate objects of interest. Since it takes on the order of a few seconds to change objectives, this alternate method of operation would take longer to complete.

To identify structure in tissue that cannot be captured in a single field of view image or a single staining/labeling technique, the invention provides a method for histological reconstruction to analyze many fields of view on potentially many slides simultaneously. The method couples composite images in an automated manner for processing and analysis. A slide on which is mounted a cellular specimen stained to identify objects of interest is supported on a motorized stage. An image of the cellular specimen is generated, digitized, and stored in memory. As the viewing field of the objective lens is smaller than the entire cellular specimen, a histological reconstruction is made. These stored images of the entire tissue section may then be placed together in an order such that the H/E stained slide is paired with the immunohistochemistry slide, which in turn may be paired with a fluorescently labeled slide so that analysis of the images may be performed simultaneously.

An overall detection process for a candidate cell or object of interest includes a combination of decisions made at both a low (e.g., 4× or 10×) and a high magnification (40×) level. Decision-making at the low magnification level is broader in scope, e.g., objects that loosely fit the relevant color, size, and shape characteristics are identified at a 10× level.

Analysis at the 40× magnification level then proceeds to refine the decision-making and confirm objects as likely cells or candidate objects of interest. For example, at the 40× level it is not uncommon to find that some objects that were identified at 10× are artifacts, which the analysis process will then reject. In addition, closely packed objects of interest appearing at 10× are separated at the 40× level. In a situation where a cell straddles or overlaps adjacent image fields, image analysis of the individual adjacent image fields could result in the cell being rejected or undetected. To avoid missing such cells, the scanning operation compensates by overlapping adjacent image fields in both the x and y directions. An overlap amount greater than half the diameter of an average cell is desirable. In one embodiment, the overlap is specified as a percentage of the image field in the x and y directions. Alternatively, a reconstruction method as described above may be used to reconstruct the image from multiple fields of view. The reconstructed image is then analyzed and processed to find objects of interest.

The time to complete an image analysis can vary depending upon the size of the scan area and the number of candidate cells or objects of interest identified. For example, in one embodiment, a complete image analysis of a scan area of two square centimeters in which 50 objects of interest are confirmed can be performed in about 12 to 15 minutes. This example includes not only focusing, scanning and image analysis but also the saving of 40× images as a mosaic on hard drive 21 (FIG. 2).

However the scan area is defined, an initial focusing operation should be performed on each slide prior to scanning. This is required since slides differ, in general, in their placement in a carrier. These differences include slight variations of tilt of the slide in its carrier. Since each slide must remain in focus during scanning, the degree of tilt of each slide must be determined. This is accomplished with an initial focusing operation that determines the exact degree of tilt, so that focus can be maintained automatically during scanning.

Figure 13A:
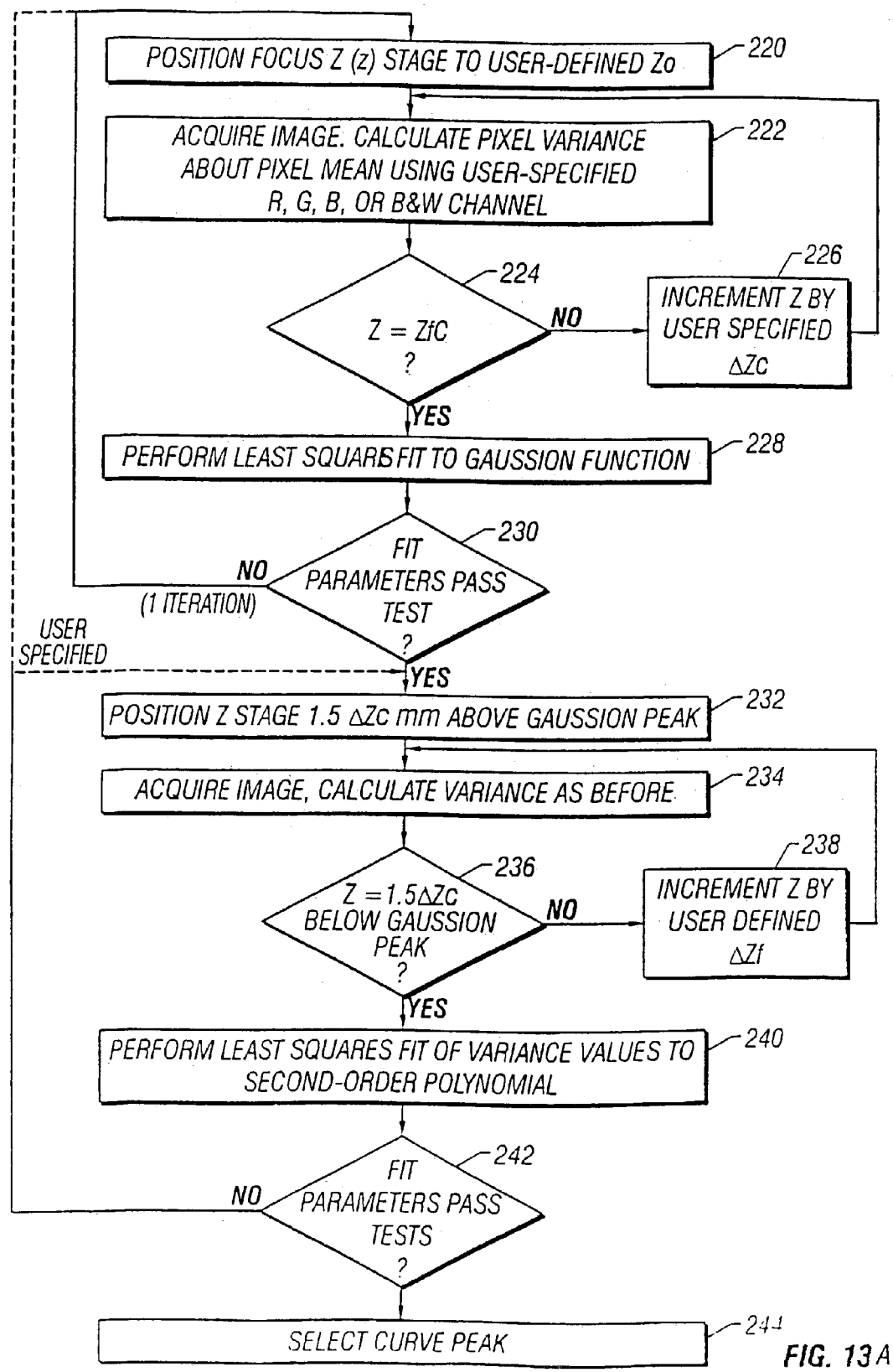
FIG. 13A is a flow diagram of a preferred procedure for determining a focal position.

The methods may vary from simple to more complex methods involving IR beam reflection and mechanical gauges. The initial focusing operation and other focusing operations to be described later utilize a focusing method based on processing of images acquired by the system. This method results in lower system cost and improved reliability since no additional parts need be included to perform focusing. FIG. 13A provides a flow diagram describing the "focus point" procedure. The basic method relies on the fact that the pixel value variance (or standard deviation) taken about the pixel value mean is maximum at best focus. A "brute-force" method could simply step through focus, using the computer controlled Z, or focus stage, calculate the pixel variance at each step, and return to the focus position providing the maximum variance. Such a method is time consuming. One method includes the determination of pixel variance at a relatively coarse number of focal positions, and then the fitting a curve to the data to provide a faster means of determining optimal focus. This basic process is applied in two steps, coarse and fine.

With reference to FIG. 13A, during the coarse step at 220-230, the Z stage is stepped over a user-specified range of focus positions, with step sizes that are also user-specified. It has been found that for coarse focusing, these data are a close fit to a Gaussian function. Therefore, this initial set of variance versus focus position data are least-squares fit to a Gaussian function at 228. The location of the peak of this Gaussian curve determines the initial or coarse estimate of focus position for input to step 232.

Following this, a second stepping operation 232-242 is performed utilizing smaller steps over a smaller focus range centered on the coarse focus position. Experience indicates that data taken over this smaller range are generally best fit by a second order polynomial. Once this least squares fit is performed at 240, the peak of the second order curve provides the fine focus position at 244.

Figure 14:
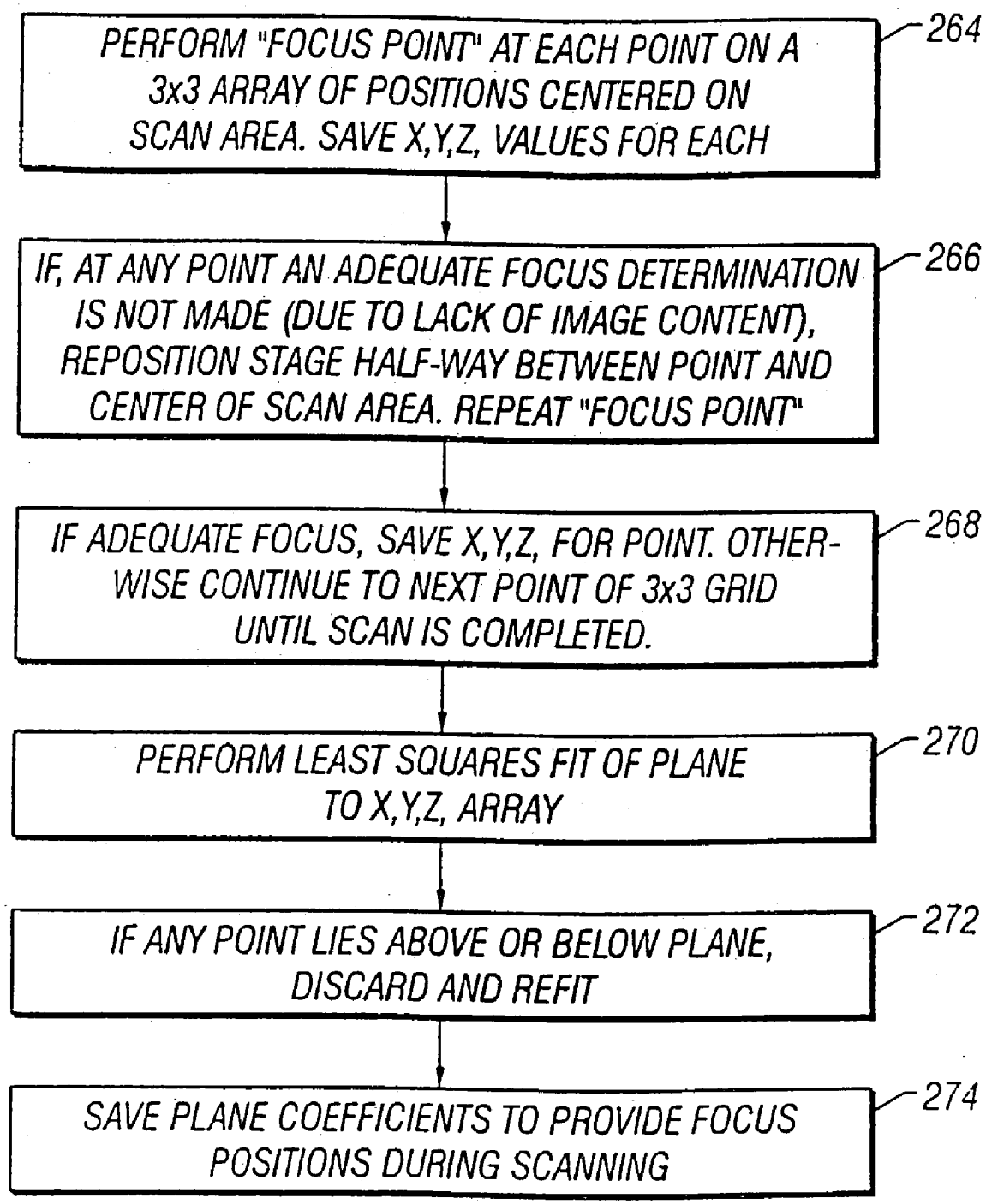
FIG. 14 is a flow diagram of a procedure for automatically determining initial focus.
Figure 15:
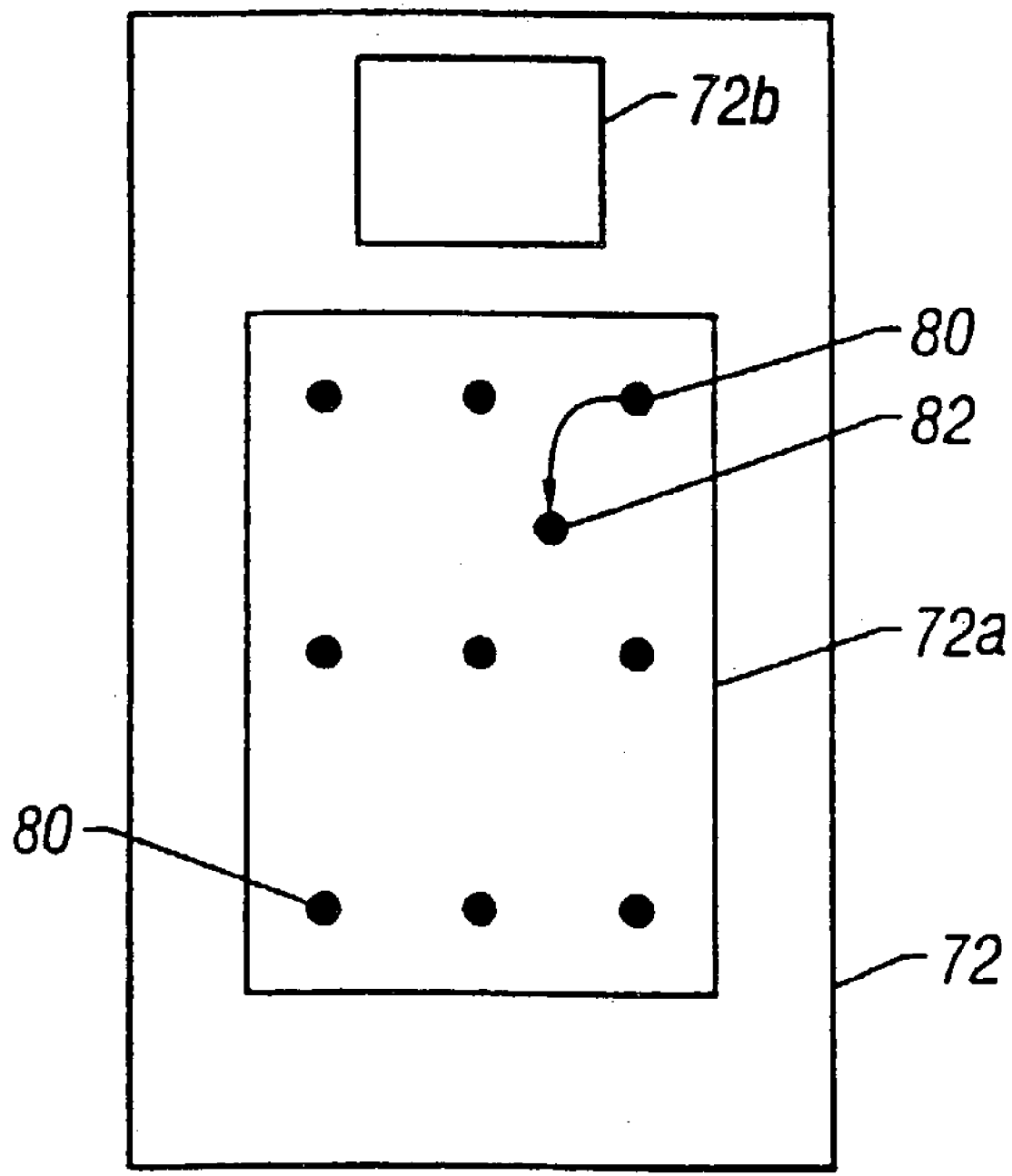
FIG. 15 shows an array of slide positions for use in the procedure of FIG. 14.

FIG. 14 illustrates a procedure for how this focusing method is utilized to determine the orientation of a slide in its carrier. As shown, focus positions are determined, as described above, for a 3×3 grid of points centered on the scan area at 264. Should one or more of these points lie outside the scan area, the method senses this at 266 by virtue of low values of pixel variance. In this case, additional points are selected closer to the center of the scan area. FIG. 15 shows the initial array of points 80 and new point 82 selected closer to the center. Once this array of focus positions is determined at 268, a least squares plane is fit to this data at 270. Focus points lying too far above or below this best-fit plane are discarded at 272 (such as can occur from a dirty cover glass over the scan area), and the data is then refit. This plane at 274 then provides the desired Z position information for maintaining focus during scanning.

Figure 16:
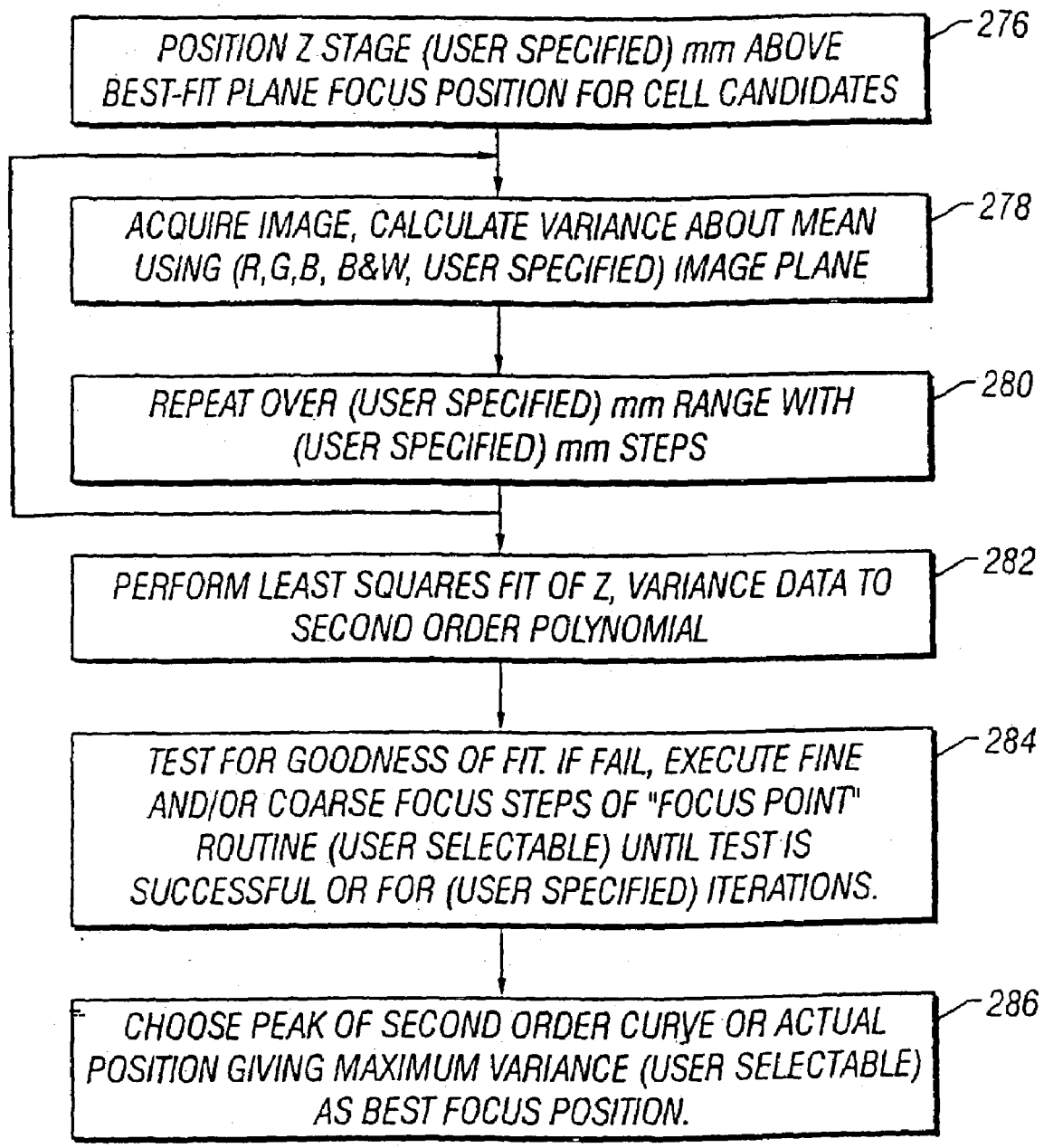
FIG. 16 is a flow diagram of a procedure for automatic focusing at a high magnification.

After determination of the best-fit focus plane, the scan area is scanned in an X raster scan over the scan area as described earlier. During scanning, the X stage is positioned to the starting point of the scan area, the focus (Z) stage is positioned to the best fit focus plane, an image is acquired and processed as described later, and this process is repeated for all points over the scan area. In this way, focus is maintained automatically without the need for time-consuming refocusing at points during scanning. Prior to confirmation of candidate cells or objects of interest at a 40× or 60× level, a refocusing operation is conducted since the use of this higher magnification requires more precise focus than the best-fit plane provides. FIG. 16 provides the flow diagram for this process. As may be seen, this process is similar to the fine focus method described earlier in that the object is to maximize the image pixel variance. This is accomplished by stepping through a range of focus positions with the Z stage at 276 and 278, calculating the image variance at each position at 278, fitting a second order polynomial to these data at 282, and calculating the peak of this curve to yield an estimate of the best focus position at 284 and 286. This final focusing step differs from previous ones in that the focus range and focus step sizes are smaller since this magnification requires focus settings to within 0.5 micron or better. It should be noted that for some combinations of cell staining characteristics, improved focus can be obtained by numerically selecting the focus position that provides the largest variance, as opposed to selecting the peak of the polynomial. In such cases, the polynomial is used to provide an estimate of best focus, and a final step selects the actual Z position giving highest pixel variance. It should also be noted that if at any time during the focusing process at 40× or 60× the parameters indicate that the focus position is inadequate, the system automatically reverts to a coarse focusing process as described above with reference to FIG. 13A. This ensures that variations in specimen thickness can be accommodated in an expeditious manner. For some biological samples and stains, the focusing methods discussed above do not provide optimal focused results. For example, certain white blood cells known as neutrophils may be stained with Fast Red, a commonly known stain, to identify alkaline phosphatase in the cytoplasm of the cells. To further identify these cells and the material within them, the specimen may be counterstained with hematoxylin to identify the nucleus of the cells. In cells so treated, the cytoplasm bearing alkaline phosphatase becomes a shade of red proportionate to the amount of alkaline phosphatase in the cytoplasm and the nucleus becomes blue. However, where the cytoplasm and nucleus overlap, the cell appears purple. These color combinations may preclude the finding of a focused Z position using the focus processes discussed above. Where a sample has been labeled with a fluorescent agent the focus plane may be based upon the intensity of a fluorescent signal. For example, as the image scans through a Z-plane of the sample, the intensity of fluorescence will change as the focus plane passes closer to the fluorescence indicator.

Figure 13B:
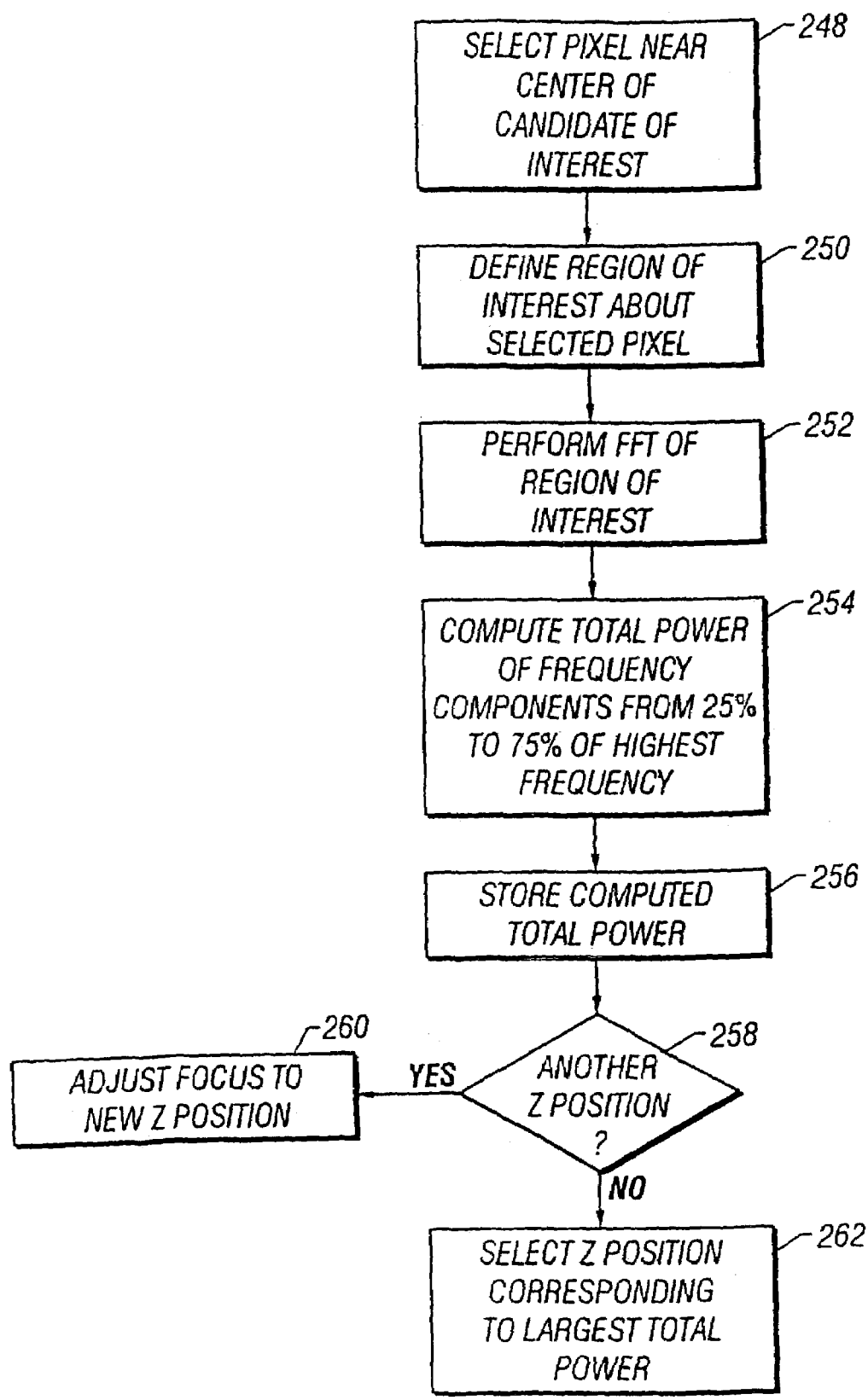
FIG. 13B is a flow diagram of a preferred procedure for determining a focal position for neutrophils stained with Fast Red and counterstained with hematoxylin.

In an effort to find a best focal position at high magnification, a focus method, such as the one shown in FIG. 13B, may be used. That method begins by selecting a pixel near the center of a candidate object of interest 248 and defining a region of interest centered about the selected pixel 250. Typically, the width of the region of interest is a number of columns, which is a power of 2. This width determination arises from subsequent processing of the region of interest using a one dimensional Fast Fourier Transform (FFT) technique. As is well known in the art, processing columns of pixel values using the FFT technique is facilitated by making the number of columns to be processed a power of two. While the height of the region of interest is also a power of two, it need not be unless a two dimensional FFT technique is used to process the region of interest.

After the region of interest is selected, the columns of pixel values are processed using a one dimensional FFT to determine a spectra of frequency components for the region of interest 252. The frequency spectra ranges from DC to some highest frequency component. For each frequency component, a complex magnitude is computed. The complex magnitudes for the frequency components, which range from approximately 25% of the highest component to approximately 75% of the highest component, are squared and summed to determine the total power for the region of interest 254. Alternatively, the region of interest may be processed with a smoothing window, such as a Hanning window, to reduce the spurious high frequency components generated by the FFT processing of the pixel values in the region of interest. Such preprocessing of the region of interest permits complex magnitudes over the complete frequency range to be squared and summed. After the power for a region has been computed and stored 256, a new focal position is selected, focus adjusted 258 and 260, and the process repeated. After each focal position has been evaluated, the one having the greatest power factor is selected as the one best in focus 262.

The following describes the image processing methods which are utilized to decide whether a candidate object of interest such as a stained tumor cell is present in a given image, or field, during the scanning process. Candidate objects of interest, which are detected during scanning, are reimaged at higher (40× or 60×) magnification, the decision confirmed, and an image of the object of interest as well as its coordinates saved for later review. In one aspect of the invention, objects of interest are first acquired and identified under transmitted light. The image processing includes color space conversion, low pass filtering, background suppression, artifact suppression, morphological processing, and blob analysis. One or more of these steps can optionally be eliminated. The operator may optionally configure the system to perform any or all of these steps and whether to perform certain steps more than once or several times in a row. It should also be noted that the sequence of steps may be varied and thereby optimized for specific reagents or reagent combinations; however, a typical sequence is described herein.

Figure 17A:
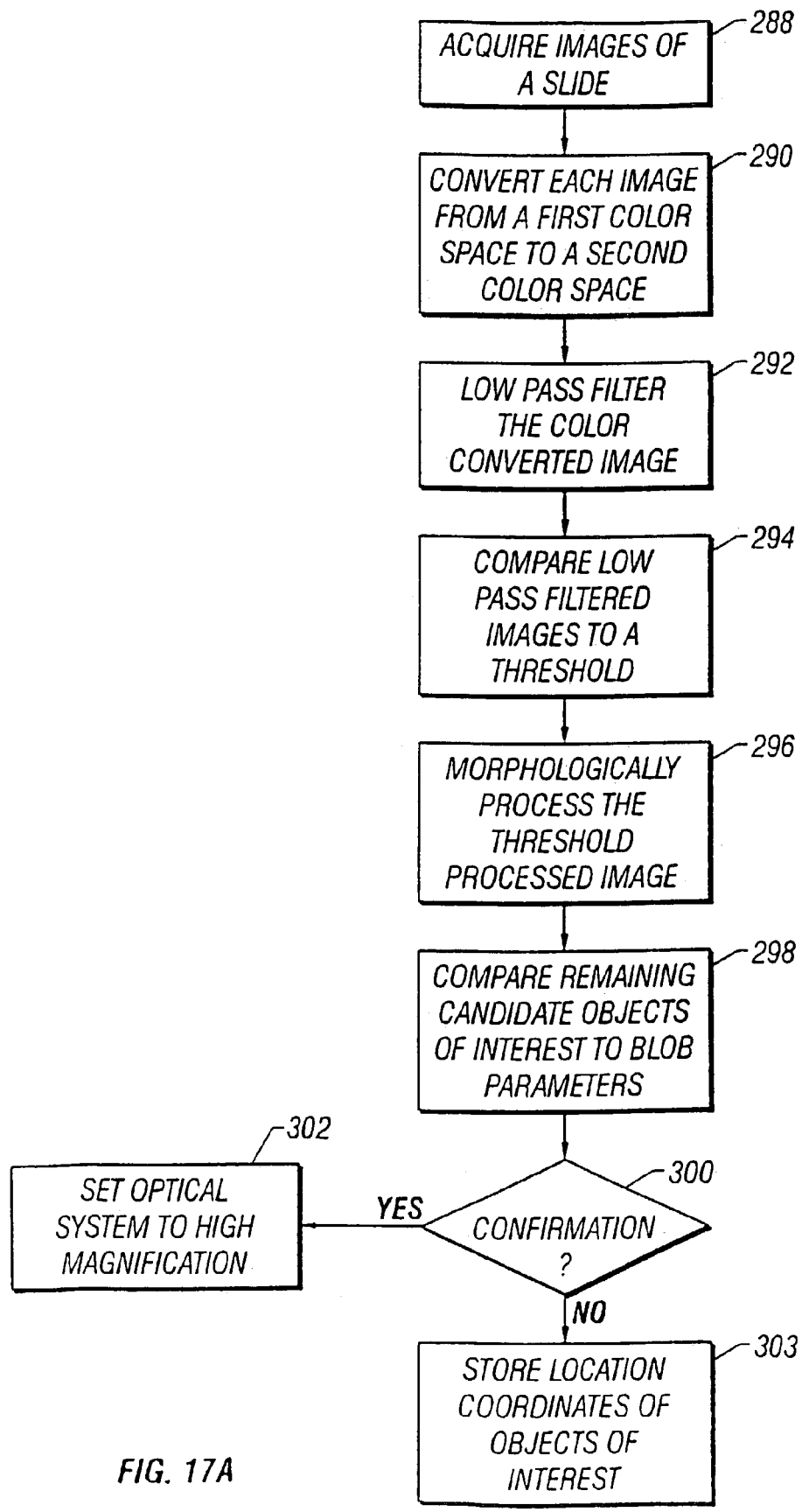
FIG. 17A is a flow diagram of an overview of the preferred process to locate and identify objects of interest in a stained biological sample on a slide.

An overview of the identification process is shown in FIG. 17A. The process for identifying and locating candidate objects of interest in a stained biological sample under transmitted light on a slide begins with an acquisition of images obtained by scanning the slide at low magnification 288. Each image is then converted from a first color space to a second color space 290 and the color converted image is low pass filtered 292. The pixels of the low pass filtered image are then compared to a threshold 294 and those pixels having a value equal to or greater than the threshold are identified as candidate object of interest pixels and those less than the threshold are determined to be artifact or background pixels. The candidate object of interest pixels are then morphologically processed to identify groups of candidate object of interest pixels as candidate objects of interest 296. These candidate objects of interest are then compared to blob analysis parameters 298 to further differentiate candidate objects of interest from objects, which do not conform to the blob analysis parameters and do not warrant further processing. The location of the candidate objects of interest may be stored prior to confirmation at high magnification. The process continues by determining whether the candidate objects of interest have been confirmed 300. If they have not been confirmed, the optical system is set to high magnification 302 and images of the slide at the locations corresponding to the candidate objects of interest identified in the low magnification images are acquired 288. These images are then color converted 290, low pass filtered 292, compared to a threshold 294, morphologically processed 296, and compared to blob analysis parameters 298 to confirm which candidate objects of interest located from the low magnification images are objects of interest. The coordinates of the objects of interest are then stored for future reference.

In general, the candidate objects of interest, such as tumor cells, are detected based on a combination of characteristics, including size, shape, and color. The chain of decision making based on these characteristics begins with a color space conversion process. The optical sensing array coupled to the microscope subsystem outputs a color image comprising a matrix of pixels. Each pixel comprises red, green, and blue (RGB) signal values.

It is desirable to transform the matrix of RGB values to a different color space because the difference between candidate objects of interest and their background, such as tumor and normal cells, may be determined from their respective colors. Samples are generally stained with one or more standard stains (e.g., DAB, New Fuchsin, AEC), which are "reddish" in color. Candidate objects of interest retain more of the stain and thus appear red while normal cells remain unstained. The specimens may also be counterstained with hematoxylin so the nuclei of normal cells or cells not containing an object of interest appear blue. In addition to these objects, dirt and debris can appear as black, gray, or can also be lightly stained red or blue depending on the staining procedures utilized. The residual plasma or other fluids also present on a smear (tissue) may also possess some color.

In the color conversion operation, a ratio of two of the RGB signal values is formed to provide a means for discriminating color information. With three signal values for each pixel, nine different ratios can be formed: R/R, R/G, R/B, G/G, G/B, G/R, B/B, B/G, B/R. The optimal ratio to select depends upon the range of color information expected in the slide sample. As noted above, typical stains used in light microscopy for detecting candidate objects of interest such as tumor cells are predominantly red, as opposed to predominantly green or blue. Thus, the pixels of an object of interest that has been stained would contain a red component, which is larger than either the green or blue components. A ratio of red divided by blue (R/B) provides a value which is greater than one for, e.g. tumor cells, but is approximately one for any clear or white areas on the slide. Since other components of the sample, for example, normal cells, typically are stained blue, the R/B ratio for pixels of these other components (e.g., normal cells) yields values of less than one. The R/B ratio is used for separating the color information typical in these applications.

Figure 17B:
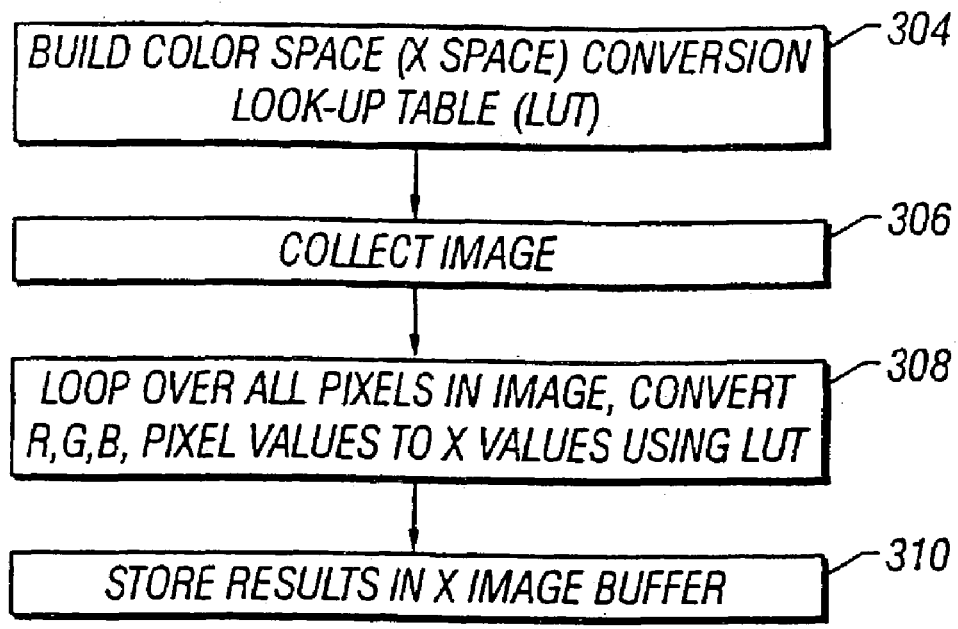
FIG. 17B is a flow diagram of a procedure for color space conversion.

FIG. 17B illustrates the flow diagram by which this conversion is performed. In the interest of processing speed, a conversion can be implemented with a look up table. The use of a look up table for color conversion accomplishes three functions: 1) performing a division operation; 2) scaling the result for processing as an image having pixel values ranging from 0 to 255; and 3) defining objects which have low pixel values in each color band (R,G,B) as "black" to avoid infinite ratios (e.g., dividing by zero). These "black" objects are typically staining artifacts or can be edges of bubbles caused by pasting a coverglass over the specimen. Once the look up table is built at 304 for the specific color ratio (e.g., choices of tumor and nucleated cell stains), each pixel in the original RGB image is converted at 308 to produce the output. Since it is of interest to separate the red stained tumor cells from blue stained normal ones, the ratio of color values is then scaled by a user specified factor. As an example, for a factor of 128 and the ratio of (red pixel value)/(blue pixel value), clear areas on the slide would have a ratio of 1 scaled by 128 for a final X value of 128. Pixels that lie in red stained tumor cells would have X value greater than 128, while blue stained nuclei of normal cells would have value less than 128. In this way, the desired objects of interest can be numerically discriminated. The resulting pixel matrix, referred to as the X-image, is a gray scale image having values ranging from 0 to 255.

Other methods exist for discriminating color information. One classical method converts the RGB color information into another color space, such as HSI (hue, saturation, intensity) space. In such a space, distinctly different hues such as red, blue, green, yellow, may be readily separated. In addition, relatively lightly stained objects may be distinguished from more intensely stained ones by virtue of differing saturations. Methods of converting from RGB space to HSI space are described in U.S. Pat. No. 6,404,916 B1, the entire contents of which are incorporated by reference. In brief, color signal inputs are received by a converter that converts the representation of a pixel's color from red, green, and blue (RGB) signals to hue, saturation, and intensity signals (HSI). The conversion of RGB signals to HSI signals is equivalent to a transformation from the rectilinear RGB coordinate system used in color space to a cylindrical coordinate system in which hue is the polar coordinate, saturation is the radial coordinate, and intensity is the axial coordinate, whose axis lies on a line between black and white in coordinate space. A number of algorithms to perform this conversion are known, and computer chips are available to perform the algorithms.

Exemplary methods include a process whereby a signal representative of a pixel color value is converted to a plurality of signals, each signal representative of a component color value including a hue value, a saturation value, and an intensity value. For each component color value, an associated range of values is set. The ranges together define a non-rectangular subvolume in HSI color space. A determination is made whether each of the component values falls within the associated range of values. The signal is then outputting, indicating whether the pixel color value falls within the color range in response to each of the component values falling within the associated range of values. The range of values associated with the hue value comprises a range of values between a high hue value and a low hue value, the range of values associated with the saturation value comprises a range of values above a low saturation value, and the range of values associated with the intensity value comprises a range of values between a high intensity value and a low intensity value.

Such methods can be executed on an apparatus that may include a converter to convert a signal representative of a pixel color value to a plurality of signals representative of component color values including a hue value, a saturation value, and an intensity value. The hue comparator determines if the hue value falls within a first range of values. The apparatus may further include a saturation comparator to determine if the saturation value falls within a second range of values, as well as an intensity comparator to determine if the intensity value falls within a third range of values. In addition, a color identifier connected to each of the hue comparator, the saturation comparator, and the intensity comparator, is adapted to output a signal representative of a selected color range in response to the hue value falling within the first range of values, the saturation value falling within the second range of values, and the intensity value falling within the third range of values. The first range of values, the second range of values, and the third range of values define a non-rectangular subvolume in HSI color space, wherein the first range of values comprises a plurality of values between a low hue reference value and a high hue reference value, the second range of values comprises a plurality of values above a low saturation value, and the third range of values comprises a plurality of values between a low intensity value and a high intensity value.

In yet another approach, one could obtain color information by taking a single color channel from the optical sensing array. As an example, consider a blue channel, in which objects that are red are relatively dark. Objects which are blue, or white, are relatively light in the blue channel. In principle, one could take a single color channel, and simply set a threshold wherein everything darker than some threshold is categorized as a candidate object of interest, for example, a tumor cell, because it is red and hence dark in the channel being reviewed. However, one problem with the single channel approach occurs where illumination is not uniform. Non-uniformity of illumination results in non-uniformity across the pixel values in any color channel, for example, tending to peak in the middle of the image and dropping off at the edges where the illumination falls off. Performing thresholding on this non-uniform color information runs into problems, as the edges sometimes fall below the threshold, and therefore it becomes more difficult to pick the appropriate threshold level. However, with the ratio technique, if the values of the red channel fall off from center to edge, then the values of the blue channel also fall off center to edge, resulting in a uniform ratio at non-uniform lighting. Thus, the ratio technique is more immune to illumination.

As described, the color conversion scheme is relatively insensitive to changes in color balance, e.g., the relative outputs of the red, green, and blue channels. However, some control is necessary to avoid camera saturation, or inadequate exposures in any one of the color bands. This color balancing is performed automatically by utilizing a calibration slide consisting of a clear area, and a "dark" area having a known optical transmission or density. The system obtains images from the clear and "dark" areas, calculates "white" and "black" adjustments for the image-frame grabber or image processor 25, and thereby provides correct color balance.

In addition to the color balance control, certain mechanical alignments are automated in this process. The center point in the field of view for the various microscope objectives as measured on the slide can vary by several (or several tens of) microns. This is the result of slight variations in position of the microscope objectives 44a as determined by the turret 44 (FIGS. 2 and 4), small variations in alignment of the objectives with respect to the system optical axis, and other factors. Since it is desired that each microscope objective be centered at the same point, these mechanical offsets must be measured and automatically compensated.

This is accomplished by imaging a test slide that contains a recognizable feature or mark. An image of this pattern is obtained by the system with a given objective, and the position of the mark determined. The system then rotates the turret to the next lens objective, obtains an image of the test object, and its position is redetermined. Apparent changes in position of the test mark are recorded for this objective. This process is continued for all objectives. Once these spatial offsets have been determined, they are automatically compensated for by moving the XY stage 38 by an equal (but opposite) amount of offset during changes in objective. In this way, as different lens objectives are selected, there is no apparent shift in center point or area viewed. A low pass filtering process precedes thresholding. An objective of thresholding is to obtain a pixel image matrix having only candidate cells or objects of interest, such as tumor cells above a threshold level and everything else below it. However, an actual acquired image will contain noise. The noise can take several forms, including white noise and artifacts. The microscope slide can have small fragments of debris that pick up color in the staining process and these are known as artifacts. These artifacts are generally small and scattered areas, on the order of a few pixels, which are above the threshold. The purpose of low pass filtering is to essentially blur or smear the entire color converted image. The low pass filtering process will smear artifacts more than larger objects of interest, such as tumor cells and thereby eliminate or reduce the number of artifacts that pass the thresholding process. The result is a cleaner thresholded image downstream. In the low pass filter process, a 3×3 matrix of coefficients is applied to each pixel in the X-image. A preferred coefficient matrix is as follows:

| | | |
|---|---|---|
| 1/9 | 1/9 | 1/9 |
| 1/9 | 1/9 | 1/9 |
| 1/9 | 1/9 | 1/9 |

At each pixel location, a 3×3 matrix comprising the pixel of interest and its neighbors is multiplied by the coefficient matrix and summed to yield a single value for the pixel of interest. The output of this spatial convolution process is again a pixel matrix. As an example, consider a case where the center pixel and only the center pixel, has a value of 255 and each of its other neighbors, top left, top, top right and so forth, have values of 0.

This singular white pixel case corresponds to a small object. The result of the matrix multiplication and addition using the coefficient matrix is a value of (1/9)*255 or 28.3 for the center pixel, a value which is below the nominal threshold of 128. Now consider another case in which all the pixels have a value of 255 corresponding to a large object. Performing the low pass filtering operation on a 3×3 matrix for this case yields a value of 255 for the center pixel. Thus, large objects retain their values while small objects are reduced in amplitude or eliminated. In the preferred method of operation, the low pass filtering process is performed on the X image twice in succession.

Figure 18:
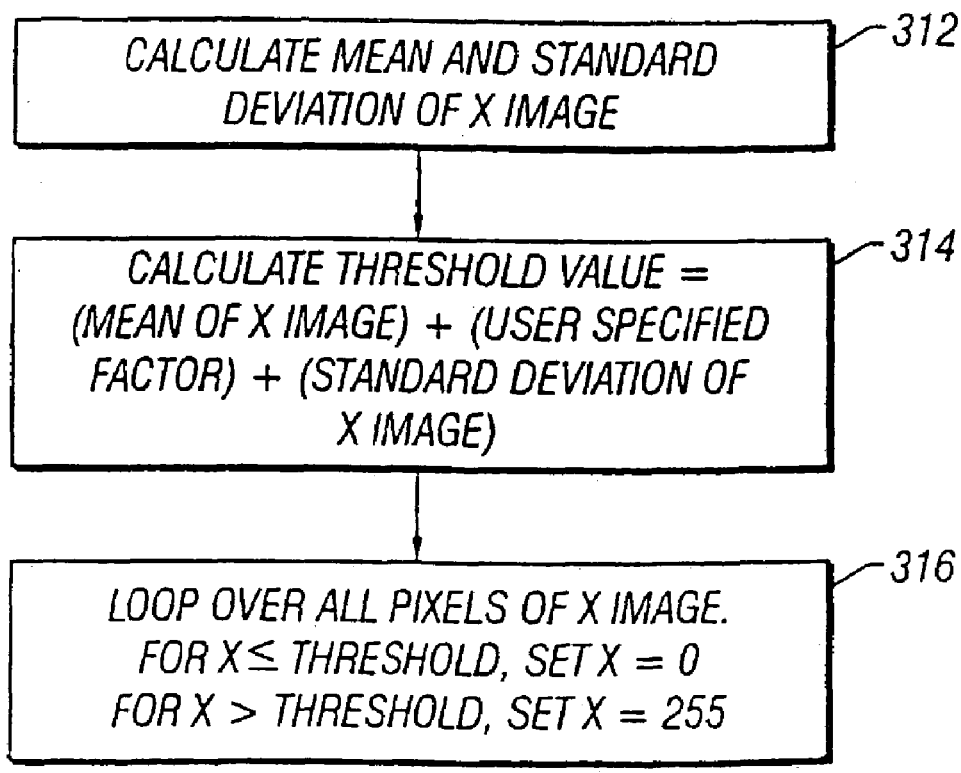
FIG. 18 is a flow diagram of a procedure for background suppression via dynamic thresholding.

In order to separate objects of interest, such as a tumor cell in the x image from other objects and background, a thresholding operation is performed designed to set pixels within candidate cells or objects of interest to a value of 255, and all other areas to 0. Thresholding ideally yields an image in which cells of interest are white and the remainder of the image is black. A problem one faces in thresholding is where to set the threshold level. One cannot simply assume that cells of interest are indicated by any pixel value above the nominal threshold of 128. A typical imaging system may use an incandescent halogen light bulb as a light source. As the bulb ages, the relative amounts of red and blue output can change. The tendency as the bulb ages is for the blue to drop off more than the red and the green. To accommodate for this light source variation over time, a dynamic thresholding process is used whereby the threshold is adjusted dynamically for each acquired image. Thus, for each image, a single threshold value is derived specific to that image. As shown in FIG. 18, the basic method is to calculate, for each field, the mean X value, and the standard deviation about this mean 312. The threshold is then set at 314 to the mean plus an amount defined by the product of a factor (e.g., a user specified factor) and the standard deviation of the color converted pixel values. The standard deviation correlates to the structure and number of objects in the image. Typically, a user specified factor is in the range of approximately 1.5 to 2.5. The factor is selected to be in the lower end of the range for slides in which the stain has primarily remained within cell boundaries and the factor is selected to be in the upper end of the range for slides in which the stain is pervasively present throughout the slide. In this way, as areas are encountered on the slide with greater or lower background intensities, the threshold may be raised or lowered to help reduce background objects. With this method, the threshold changes in step with the aging of the light source such that the effects of the aging are canceled out. The image matrix resulting at 316 from the thresholding step is a binary image of black (0) and white (255) pixels. As is often the case with thresholding operations such as that described above, some undesired areas will lie above the threshold value due to noise, small stained cell fragments, and other artifacts. It is desired and possible to eliminate these artifacts by virtue of their small size compared with legitimate cells of interest. In one aspect, morphological processes are utilized to perform this function.

Morphological processing is similar to the low pass filter convolution process described earlier except that it is applied to a binary image. Similar to spatial convolution, the morphological process traverses an input image matrix, pixel by pixel, and places the processed pixels in an output matrix. Rather than calculating a weighted sum of the neighboring pixels as in the low pass convolution process, the morphological process uses set theory operations to combine neighboring pixels in a nonlinear fashion.

Erosion is a process whereby a single pixel layer is taken away from the edge of an object. Dilation is the opposite process, which adds a single pixel layer to the edges of an object. The power of morphological processing is that it provides for further discrimination to eliminate small objects that have survived the thresholding process and yet are not likely objects of interest (e.g., tumor cells). The erosion and dilation processes that make up a morphological "open" operation make small objects disappear yet allow large objects to remain. Morphological processing of binary images is described in detail in "Digital Image Processing", pages 127-137, G. A. Baxes, John Wiley & Sons, (1994).

Figure 19:
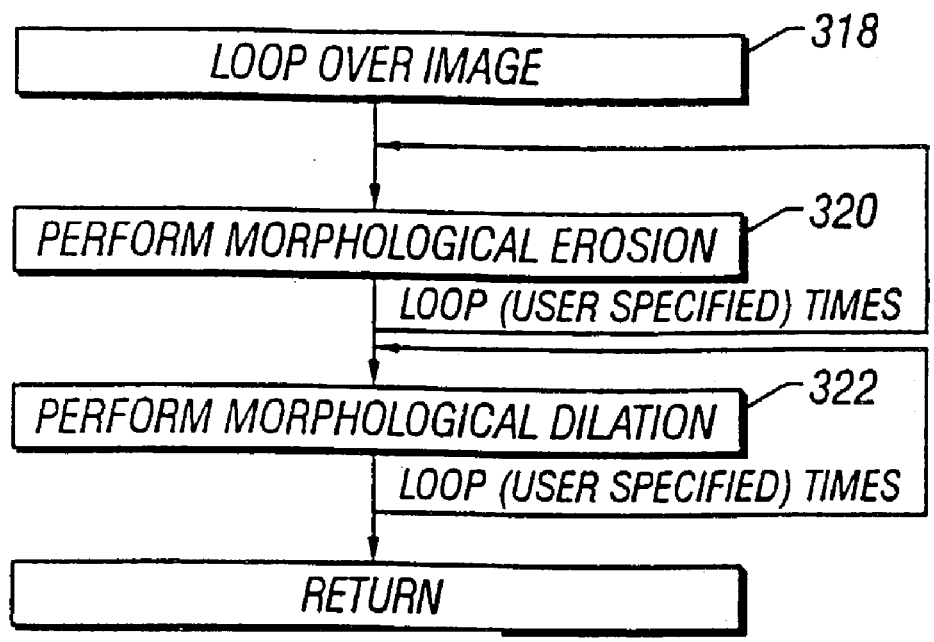
FIG. 19 is a flow diagram of a procedure for morphological processing.

FIG. 19 illustrates the flow diagram for this process. A single morphological open consists of a single morphological erosion 320 followed by a single morphological dilation 322. Multiple "opens" consist of multiple erosions followed by multiple dilations. In one embodiment, one or two morphological opens are found to be suitable. At this point in the processing chain, the processed image contains thresholded objects of interest, such as tumor cells (if any were present in the original image), and possibly some residual artifacts that were too large to be eliminated by the processes above.

Figure 20:
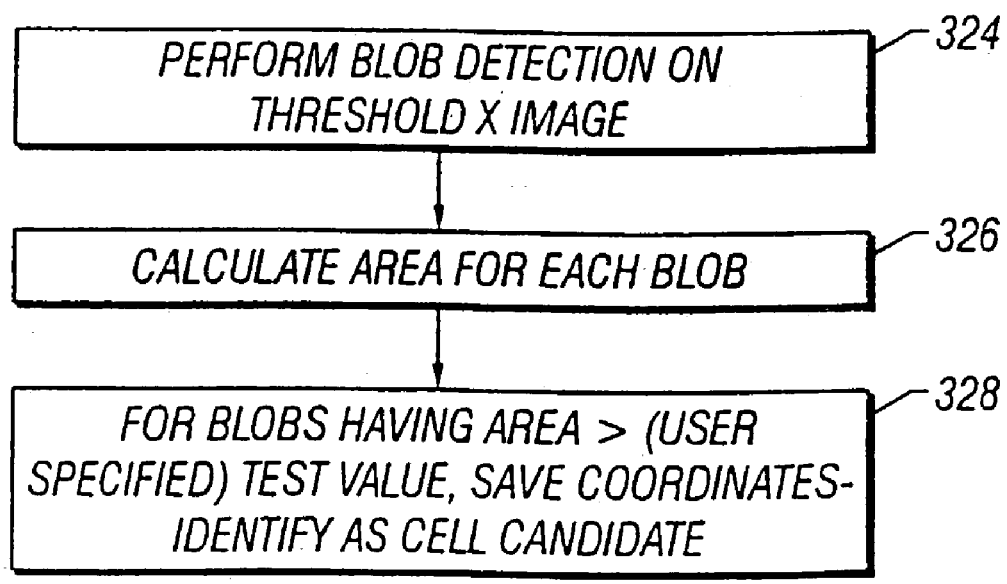
FIG. 20 is a flow diagram of a procedure for blob analysis.

FIG. 20 provides a flow diagram illustrating a blob analysis performed to determine the number, size, and location of objects in the thresholded image. A blob is defined as a region of connected pixels having the same "color", in this case, a value of 255. Processing is performed over the entire image to determine the number of such regions at 324 and to determine the area and coordinates for each detected blob at 326. Comparison of the size of each blob to a known minimum area at 328 for a tumor cell allows a refinement in decisions about which objects are objects of interest, such as tumor cells, and which are artifacts. The location of candidate cells or objects of interest identified in this process are saved for a higher magnification reimaging step described herein. Objects not passing the size test are disregarded as artifacts.

Figure 21:
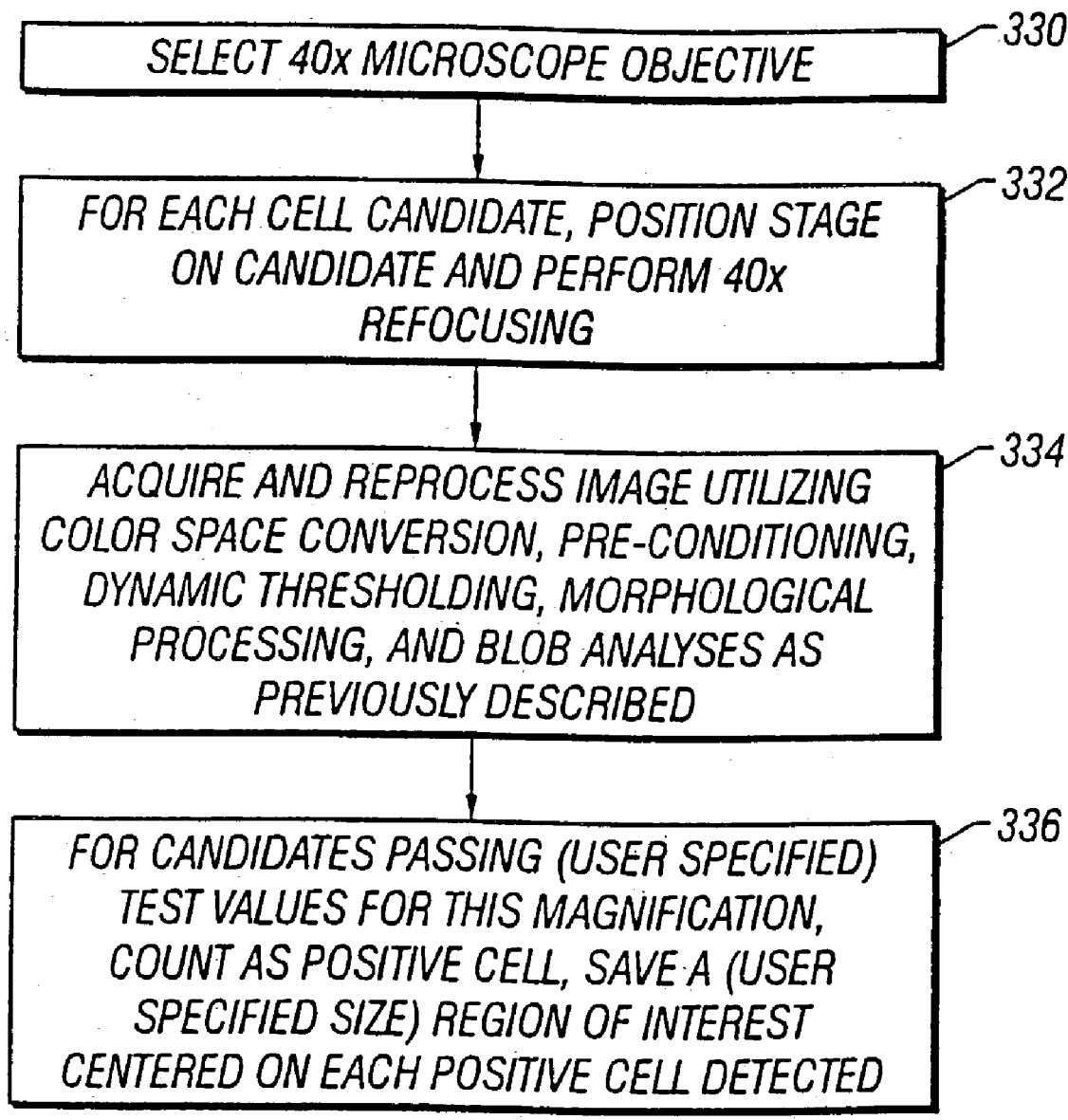
FIG. 21 is a flow diagram of a procedure for image processing at a high magnification.

The processing chain described herein identifies candidate cells or objects of interest at a scanning magnification. As illustrated in FIG. 21, at the completion of scanning, the system switches to a higher magnification objective (e.g., 40×) at 330, and each candidate cell or object of interest is reimaged to confirm the identification 332. Each 40× image is reprocessed at 334 using the same steps as described above but with test parameters suitably modified for the higher magnification. At 336, a region of interest centered on each confirmed cell is saved to the hard drive for review by the pathologist.

Similarly, once imaging has been performed in transmitted light imaging in fluorescent light may be performed using a process described above. For example, as illustrated in FIG. 21, at the completion of scanning and imaging at a higher magnification under transmitted light, the system switches from transmitted light to fluorescent excitation light and obtains images at a desired magnification objective (e.g., 40×) at 330, and each candidate cell or object of interest identified under transmitted light is reimaged under fluorescent light 332. Each fluorescent image is then processed at 334 but with test parameters suitably modified for the fluorescent imaging. At 336, fluorescent image comprising a fluorescently labeled object of interest is saved to storage device for review by a pathologist.

Figure 22:
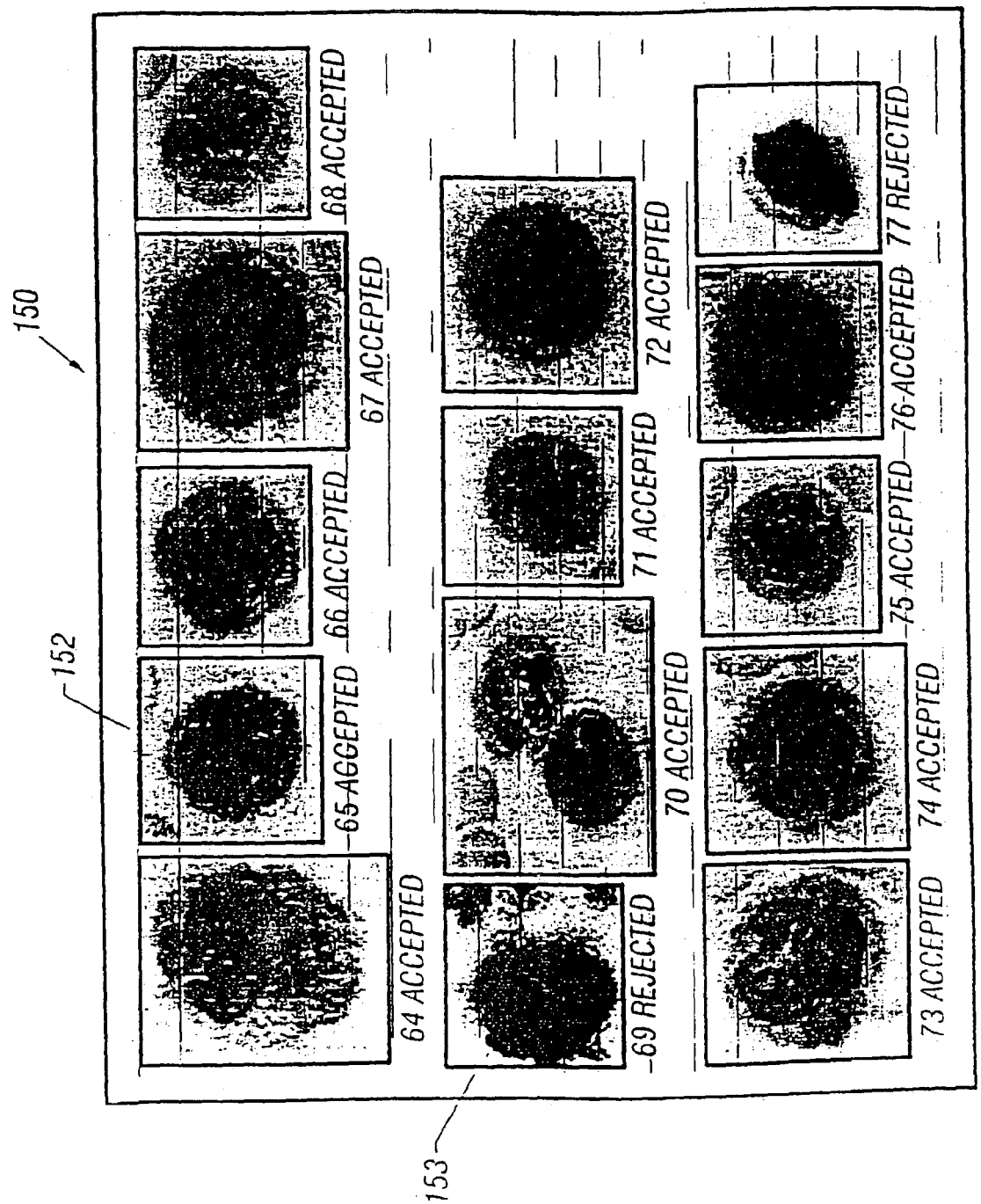
FIG. 22 illustrates a mosaic of cell images produced by the apparatus.

As noted earlier, a mosaic of saved images is made available for review by a pathologist. As shown in FIG. 22, a series of images of cells that have been confirmed by the image analysis is presented in the mosaic 150. The pathologist can then visually inspect the images to make a determination whether to accept (152) or reject (153) each cell image. Such a determination can be noted and saved with the mosaic of images for generating a printed report.

In addition to saving an image of a candidate cell or object of interest, the coordinates are saved should the pathologist wish to directly view the cell through the oculars or on the image monitor. In this case, the pathologist reloads the slide carrier, selects the slide and cell for review from a mosaic of cell images, and the system automatically positions the cell under the microscope for viewing.

Figure 23:
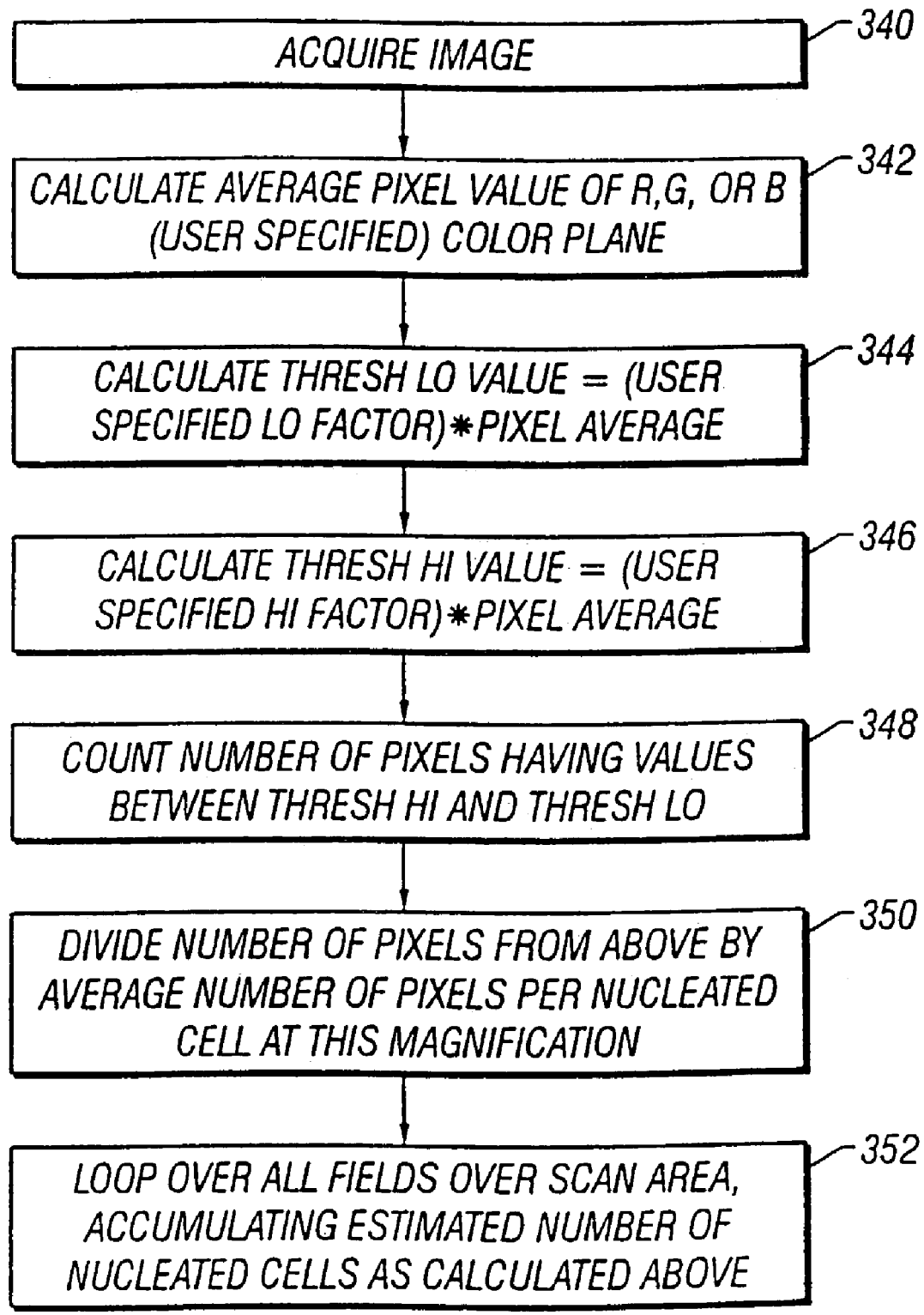
FIG. 23 is a flow diagram of a procedure for estimating the number of nucleated cells in a field.

It has been found that normal cells whose nuclei have been stained with hematoxylin are often quite numerous, numbering in the thousands per 10× image. Since these cells are so numerous, and since they tend to clump, counting each individual nucleated cell would add an excessive processing burden, at the expense of speed, and would not necessarily provide an accurate count due to clumping. The apparatus performs an estimation process in which the total area of each field that is stained hematoxylin blue is measured and this area is divided by the average size of a nucleated cell. FIG. 23 outlines this process. In this process, an image is acquired 340, and a single color band (e.g., the red channel provides the best contrast for blue stained nucleated cells) is processed by calculating the average pixel value for each field at 342, thereby establishing two threshold values (high and low) as indicated at 344, 346, and counting the number of pixels between these two values at 348. In the absence of dirt, or other opaque debris, this provides a count of the number of predominantly blue pixels. By dividing this value by the average area for a nucleated cell at 350, and looping over all fields at 352, an approximate cell count is obtained. This process yields an accuracy of +/−15%. It should be noted that for some slide preparation techniques, the size of nucleated cells can be significantly larger than the typical size. The operator can select the appropriate nucleated cell size to compensate for these characteristics.

As with any imaging system, there is some loss of modulation transfer (e.g., contrast) due to the modulation transfer function (MTF) characteristics of the imaging optics, camera, electronics, and other components. Since it is desired to save "high quality" images of cells of interest both for pathologist review and for archival purposes, it is desired to compensate for these MTF losses. An MTF compensation (MTFC) is performed as a digital process applied to the acquired digital images. A digital filter is utilized to restore the high spatial frequency content of the images upon storage, while maintaining low noise levels. With this MTFC technology, image quality is enhanced, or restored, through the use of digital processing methods as opposed to conventional oil-immersion or other hardware based methods. MTFC is described further in "The Image Processing Handbook," pages 225 and 337, J. C. Rues, CRC Press (1995).

Figure 24A:
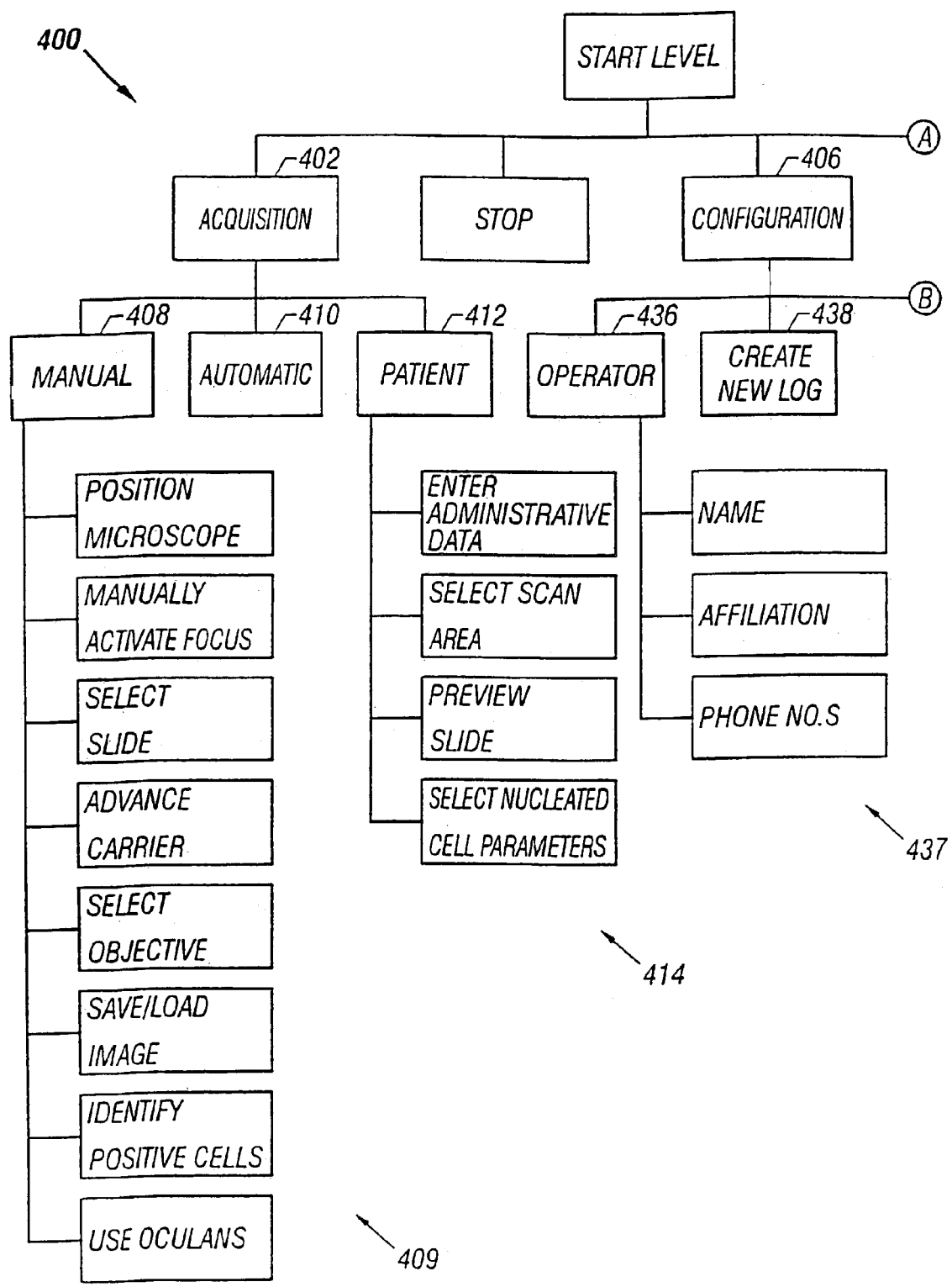
FIGS. 24a and 24b illustrate the apparatus functions available in a user interface of the apparatus.
Figure 24B:
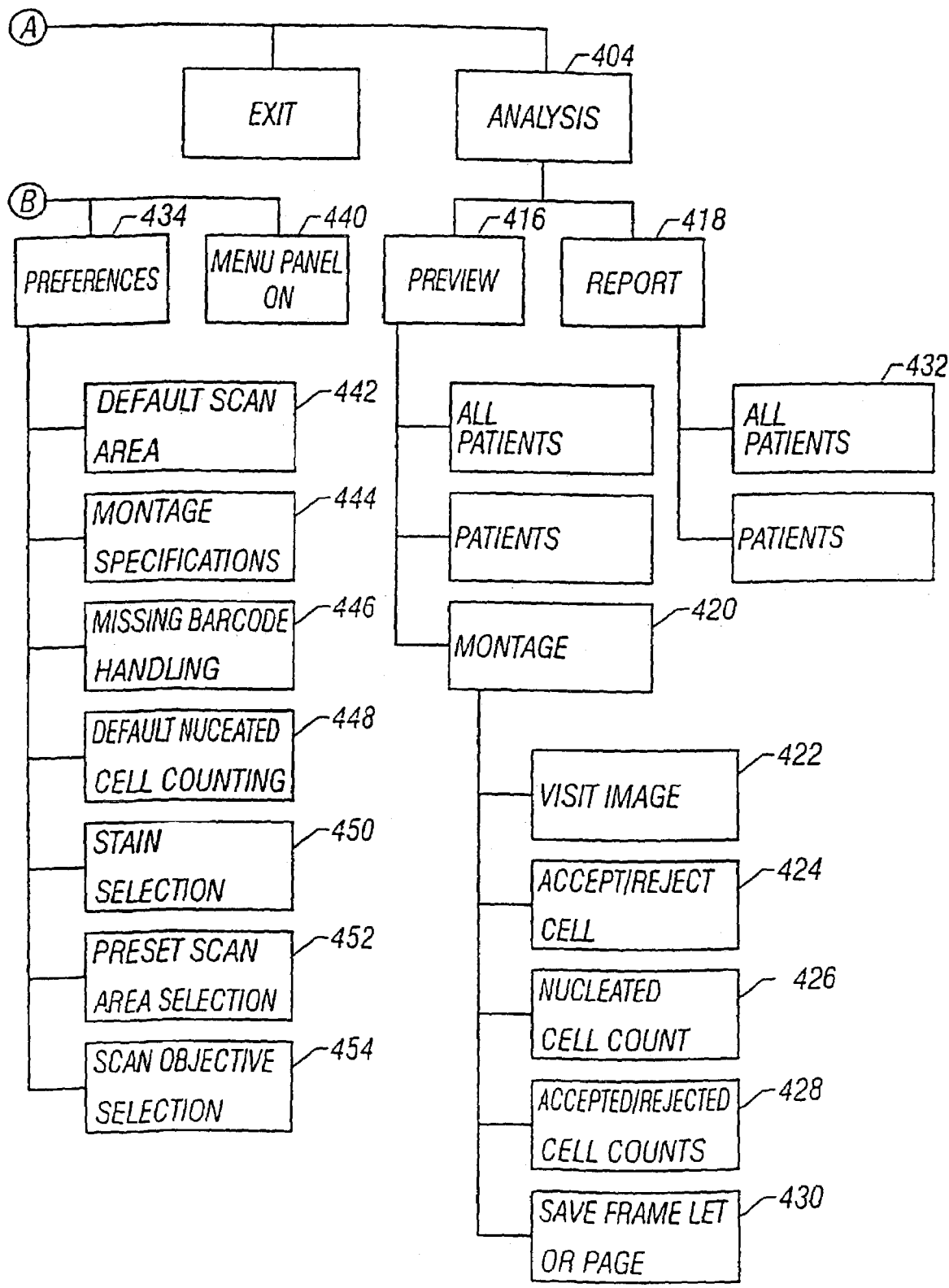

Referring to FIG. 24, the functions available in a user interface of the apparatus 10 are shown. From the user interface, which is presented graphically on computer monitor 26, an operator can select among apparatus functions that include acquisition 402, analysis 404, and configuration 406. At the acquisition level 402, the operator can select between manual 408 and automatic 410 modes of operation. In the manual mode, the operator is presented with manual operations 409. Patient information 414 regarding an assay can be entered at 412. In the analysis level 404, preview 416 and report 418 functions are made available. At the preview level 416, the operator can select a montage function 420. At this montage level, a pathologist can perform diagnostic review functions including visiting an image 422, accept/reject a cell 424, nucleated cell counting 426, accept/reject cell counts 428, and saving of pages 430. The report level 418 allows an operator to generate patient reports 432. In the configuration level 406, the operator can select to configure preferences 434, input operator information436 including Name, affiliation and phone number 437, create a system log 438, and toggle a menu panel 440. The configuration preferences include scan area selection functions 442 and 452; montage specifications 444, bar code handling 446, default cell counting 448, stain selection 450, and scan objective selection 454.

Figure 25:
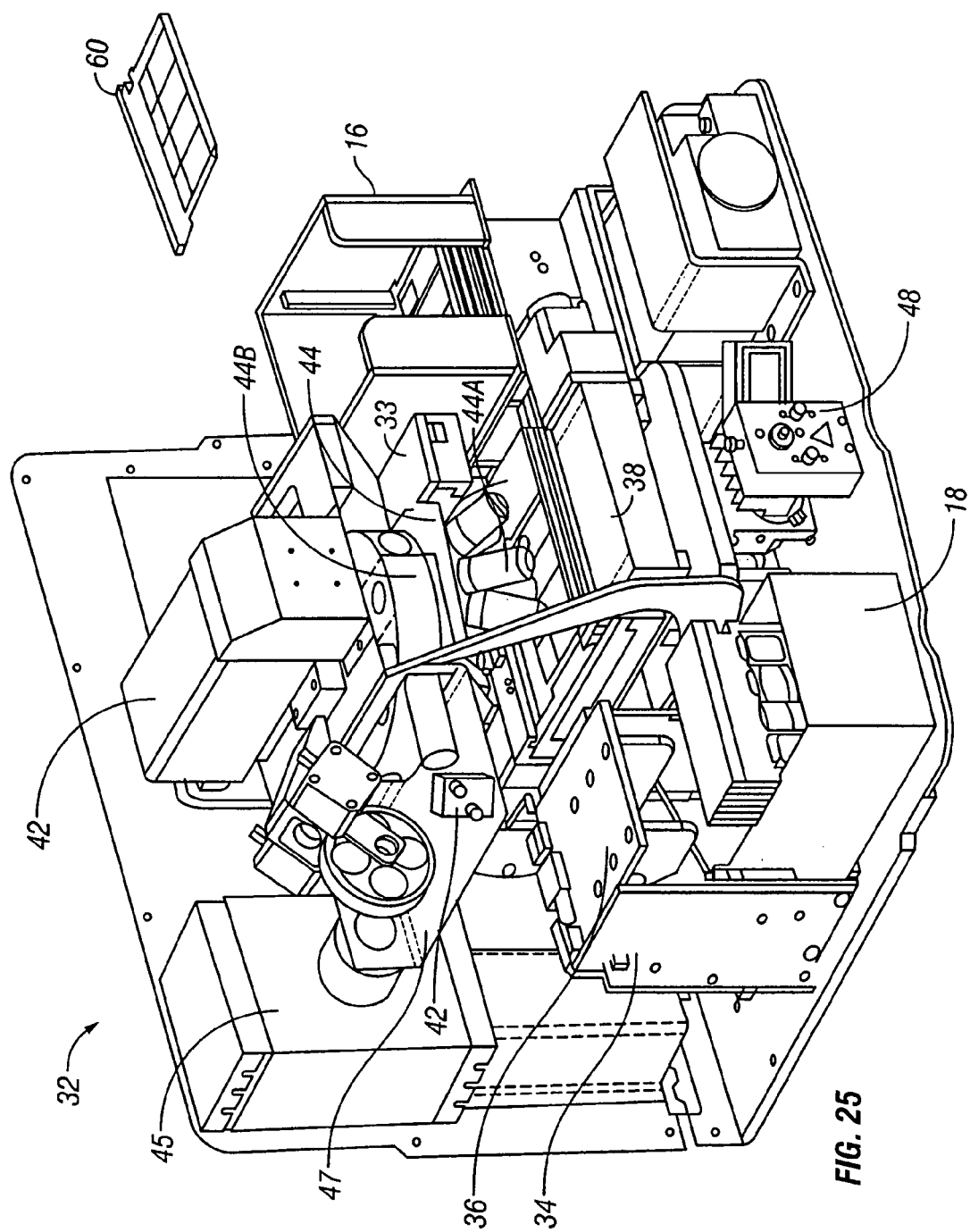
FIG. 25 is a perspective view of another embodiment of the invention.

An exemplary microscope subsystem 32 for processing fluorescently labeled samples is shown in FIG. 25. A carrier 60 having four slides thereon is shown. The number of slide in different embodiments can be greater than or less than four. An input hopper 16 for carriers with mechanisms to load a carrier 60 onto the stage at the bottom. Precision XY stage 38 with mechanism to hold carriers is shown. A turret 44 with microscope objective lenses 44a mounted on z axis stage is shown. Carrier outfeed tray 36 with mechanism 34 to drop carriers into slide carrier output hopper 18. The slide carrier output hopper 18 is a receptacle for those slides that have already been scanned. Bright field (transmission) light source 48 and fluorescent excitation light source 45 are also shown. Filter wheels 47 for fluorescent light path are shown, as well as a fold mirror 47a in the fluorescent light path. A bar code/OCR reader 33 is shown. Also shown are a computer controlled wheel 44b carrying fluorescent beam splitters (one position is empty for bright field mode) and a camera 42 capable of collecting both bright field (video rate) images and fluorescent (integrated) images.

An exemplary operating sequence is provided; however, it should be noted that other operating sequences may eliminate one or more steps and/or include one or more additional steps.

1) The operator enters each slide into a database entering the slide's unique identifying mark (a barcode or OCR string) and the test that should be performed on the slide.

2) The slides are placed in carriers 60 and loaded into the input hopper 16.

3) The infeed hopper 16 advances a carrier 60 onto the stage 38.

4) The barcode/OCR reader 33 reads the mark and the required test is looked up in a database.

5) The bright field light source 48 is switched on.

6) The entire sample on the slide is scanned at a moderate magnification. Optionally distinctive features may be identified and their coordinates stored for correction of coordinates in serial subsamples.

7) Optionally these images are saved and stitched together to form an image of the slide.

8) Image analysis routines are used to determine which regions of the slide should be recorded in fluorescent images (the methods used to make this determination are described herein, the exact parameters will depend on the test being performed on the slide).

9) The turret 44 is switched to high power and further bright field transmission analysis and images are obtained. Alternatively, the turret 44 is switched to a higher power and the bright field transmission light source turned off and the fluorescent excitation light source is turned on.

10) High magnification fluorescent images of the candidate cells or objects of interest identified in step 8 would be collected. Because the critical regions would be a small fraction of the slide this would take much less time than imaging the entire slide. Alternatively, a serial subsample slides is advanced and processed to identify the coordinates of the distinctive features identified in (6) above. The coordinates of any object of interest are then corrected in the subsample and the X-Y stage moves to the corrected coordinates to obtain fluorescent images.

11) Optionally (depending on the test) multiple images at a series of focus planes would be collected at each critical location. These would be used in tests that require a volumetric reconstruction of the nuclei of a cell.

12) All the images collected from the slide would be written to the database optionally with compression.

13) Once all images have been collected on a slide, the stage would advance the next slide under the objective and the process would repeat from step 4.

14) Once all slides in a carrier are read, the process would repeat from step 3.

15) Anytime after the slides have been read and the images recorded into the database, a pathologist could review the images at a review station (a computer and monitor attached to the database but without a microscope).

16) The user could manually count fluorescent signals in the cells of interest or invoke image analysis software to score the fluorescent images by indicating regions of interest with a pointing device such as a mouse. If multiple focus planes have been collected the user could simulate focusing up and down in a live image by sweeping through a range of images at different focus levels.

17) Based on the calculated score, a diagnostic report can be generated.

Alternatively, the image analysis could be performed on the entirety of all regions for which fluorescent images were collected. In this case, the analysis could be performed off line between the time the image was collected and the time the user reviewed the image. When reviewing the images, the user could indicate regions whose scores should be included or excluded in creating the final report.

The automated detection of fluorescent specimens may be performed using a single slide or multiple slides. In using a single slide, the initial scan, under lower power and transmitted light, can be performed on the same slide as the one from which the fluorescent images will be found. In this case, the coordinates of any identified candidate objects of interest do not need to be corrected. Alternatively, the initial scan can be performed on a slide, and the data collected therefrom, and the fluorescent images can be collected from another slide having an adjacent serial section to the one that was initially scanned. In this case, the coordinates of any identified candidate objects of interest need to be corrected based upon the coordinates of any distinctive features in the serial samples. Fluorescent images may also be collected from multiple serial sections. For example, in situations where more than one fluorescent study is desired for a particular tissue, different studies can be carried out on adjacent sections placed on different slides. The slides of the different studies can be analyzed at high resolution and/or fluorescence from data collected from the initial scan of the first slide. In using adjacent tissue sections on multiple slides, however, it is desirable to orient the sections so that the specimens will correlate from one section to the other(s). This can be done by using landmarks, such as at least two unique identifiers or distinctive features, or outlining the tissue. Algorithms are known that can be used to calculate a location on the second or additional slides that can be mapped to any given location of the first slide. Examples of such algorithms are provided herein and include techniques as disclosed in U.S. Pat. Nos. 5,602,937 and 6,272,247, the disclosures of which are incorporated herein by reference in their entirety. In addition, such computer algorithms are commercially available from Matrox Electronic Systems Ltd. (Matrox Imagining Library (MIL) release 7.5).

Regardless of whether a single slide or multiple slides are used in the analysis, methods of selecting relevant regions of the slide for analysis are needed. It is desirable that the method be sufficiently selective so that time will not be wasted collecting images that the user never scores or includes in the report. However, it is also desirable that the method not be too selective, as the user may see a region that seems important in the bright field image and find that there is no high power fluorescent image in that region. Examples of methods for selecting the regions of the slide for fluorescing and/or high power magnification are provided.

In some methods, there will be criteria known a priori, that can be evaluated by image analysis. For instance, in testing for Her2 gene amplification, the IHC stain for the gene product can be used. This will mark any region of the tissue overexpressing the gene product (the protein Her2) a brown color. The image processing functions of densitometry or color thresholding can be used to convert the image to a map of the concentration of the protein. Once a map of relevant regions is available, the system could collect high magnification fluorescent images of either all regions that meet a criteria or a random sample of the relevant regions. Another example would be the use of the blue stain H&E to find regions of containing tumor cells. In this case, color thresholding for regions of darker blue will tend to find regions of containing tumor cells.

In other methods of selecting regions, one could use statistical methods that do not require a-priori knowledge to map the tissue sample into some number of zones that share some measurable characteristic. The system could then collect fluorescent images of samples of each zone. When the user reviews the bright field image of the entire tissue and selected regions in which to examine the fluorescent high magnification images, the system could offer an image of another region in the same zone with similar characteristics. There are a number of known algorithms that could be used for dividing the tissue into zones. For instance, if the tissue were divided into a grid and the average color of each grid element were measured, these could be plotted in color space and cluster analysis used to group them into a limited number of zones with similar color. There are also texture analysis algorithms that will partition an image into a number of zones each with similar texture.

In still other methods, it may occur that on review of the bright field image, the user may find a region in which she may want to see a fluorescent image and, for whatever reason, the algorithm did not make a fluorescent image that is usable. In this case, the system could be programmed to write the location of the region the user wanted back into the database so that, if the slide is reloaded into the microscope, the system can collect a fluorescent high magnification image at the exact location desired. This mode of operation could either be a fallback for the methods of selecting regions described above or a separate mode of operation in tests in which only the observer's judgment is suitable for deciding which regions are important to examine as fluorescent images.

The HER2/neu marker, for example, may be detected though the use of an anti-HER2/neu staining system, such as a commercially available kit, like that provided by DAKO (Carpinteria, Calif.). A typical immunohistochemistry protocol includes: (1) prepare wash buffer solution; (2) deparaffinize and rehydrate sample or subsample; (3) perform epitope retrieval. Incubate 40 min in a 95° C. water bath. Cool slides for 20 min at room temperature; (4) apply peroxidase blocking reagent. Incubate 5 min; (5) apply primary antibody or negative control reagent. Incubate 30 min +/−1 min at room temperature. Rinse in wash solution. Place in wash solution bath; (6) apply peroxidase labeled polymer. Incubate 30 min +/−1 min at room temperature. Rinse in wash solution. Place in wash solution bath; (7) prepare DAB substrate chromagen solution; (8) apply substrate chromogen solution (DAB). Incubate 5-10 min. Rinse with distilled water; (9) counterstain; (10) mount coverslips. The slide includes a cover-slip medium to protect the sample and to introduce optical correction consistent with microscope objective requirements. A coverslip typically covers the entire prepared specimen. Mounting the coverslip does not introduce air bubbles obscuring the stained specimen. This coverslip could potentially be a mounted 1-½ thickness coverslip with DAKO Ultramount medium; (11) a set of staining control slides are run with every worklist. The set includes a positive and negative control. The positive control is stained with the anti-HER2 antibody and the negative is stained with another antibody. Both slides are identified with a unique barcode. Upon reading the barcode, the instrument recognizes the slide as part of a control set, and runs the appropriate application. There may be one or two applications for the stain controls; (12) a set of instrument calibration slides includes the slides used for focus and color balance calibration; (13) a dedicated carrier is used for one-touch calibration. Upon successful completion of this calibration procedure, the instrument reports itself to be calibrated. Upon successful completion of running the standard slides, the user is able to determine whether the instrument is within standards and whether the inter-instrument and intra-instrument repeatability of test results.

A hematoxylin/eosin (H/E) slide is prepared with a standard H/E protocol. Standard solutions include the following: (1) Gills hematoxylin (hematoxylin 6.0 g; aluminum sulphate 4.2 g; citric acid 1.4 g; sodium iodate 0.6 g; ethylene glycol 269 ml; distilled water 680 ml); (2) eosin (eosin yellowish 1.0 g; distilled water 100 ml); (3) lithium carbonate 1% (lithium carbonate 1 g; distilled water 100 g); (4) acid alcohol 1% 70% (alcohol 99 ml conc.; hydrochloric acid 1 ml); and (5) Scott's tap water. In a beaker containing 1 L distilled water, add 20 g sodium bicarbonate and 3.5 g magnesium sulphate. Add a magnetic stirrer and mix thoroughly to dissolve the salts. Using a filter funnel, pour the solution into a labeled bottle.

The staining procedure is as follows: (1) bring the sections to water; (2) place sections in hematoxylin for 5 min; (3) wash in tap water; (4) 'blue' the sections in lithium carbonate or Scott's tap water; (5) wash in tap water; (6) place sections in 1% acid alcohol for a few seconds; (7) wash in tap water; (8) place sections in eosin for 5 min; (9) wash in tap water; and (10) dehydrate, clear. Mount sections. The results of the H/E staining provide cells with nuclei stained blue-black, cytoplasm stained varying shades of pink; muscle fibers stained deep pinky red; fibrin stained deep pink; and red blood cells stained orange-red.

In another aspect, the invention provides automated methods for analysis of estrogen receptor and progesterone receptor. The estrogen and progesterone receptors, like other steroid hormone receptors, play a role in developmental processes and maintenance of hormone responsiveness in cells. Estrogen and progesterone receptor interaction with target genes is of importance in maintenance of normal cell function and is also involved in regulation of mammary tumor cell function. The expression of progesterone receptor and estrogen receptor in breast tumors is a useful indicator for subsequent hormone therapy. An anti-estrogen receptor antibody labels epithelial cells of breast carcinomas which express estrogen receptor. An immunohistochemical assay of the estrogen receptor is performed using an anti-estrogen receptor antibody, for example the well-characterized 1D5 clone, and the methods of Pertchuk, et al. (Cancer 77: 2514-2519, 1996) or a commercially available immunohistochemistry system such as that provided by DAKO (Carpenteria Calif.; DAKO LSAB2 Immunostaining System). Accordingly, the invention provides a method whereby tumor cells are identified using a first agent and normal light microscopy and then further characterized using antibodies to a progesterone and/or estrogen receptor, wherein the antibodies are tagged with a fluorescent agent.

For example, the labeling of progesterone receptor has been demonstrated in the nuclei of cells from various histologic subtypes. An anti-progesterone receptor antibody labels epithelial cells of breast carcinomas which express progesterone receptor. An immunohistochemical assay of the progesterone receptor is performed using an anti-estrogen receptor antibody, for example the well-characterized 1A6 clone and methods similar to those of Pertchuk, et al. (Cancer 77: 2514-2519, 1996).

Micrometastases/metastatic recurring disease (MM/MRD). Metastasis is the biological process whereby a cancer spreads to a distant part of the body from its original site. A micrometastases is the presence of a small number of tumor cells, particularly in the lymph nodes and bone marrow. A metastatic recurring disease is similar to micrometastasis, but is detected after cancer therapy rather than before therapy. An immunohistochemical assay for MM/MRD is performed using a monoclonal antibody that reacts with an antigen (a metastatic-specific mucin) found in bladder, prostate and breast cancers. An MM/MRD can be identified by first staining cells to identify nucleic and cellular organelles or alternatively by staining cells to differentiate between bladder and other prostate cells. Subsamples corresponding to the original first subsample can then be stained with and antibody to a mucin protein, wherein the antibody is detectably labeled with a fluorescent molecule. In this way, a first subsample is prescreened to identify objects of interest including a particular cell type and then screened with a specific antibody to a molecule of interest associated with the object of interest. The first screening step allows for an automated system to identify the coordinates in a first subsample having the object of interest whereby the coordinates are then used to focus and obtaining fluorescent images in a second subsample at the same coordinates.

Another example of the application of the invention includes the use of MIB-1. MIB-1 is an antibody that detects the antigen Ki-67. The clinical stage at first presentation is related to the proliferative index measured with Ki-67. High index values of Ki-67 are positively correlated with metastasis, death from neoplasia, low disease-free survival rates, and low overall survival rates. For example, a first agent (e.g., a staining agent) is used to identify an object of interest such as a marker for cancer cells. A diagnosis or prognosis of a subject may then be performed by further analyzing any object of interest for the presence of Ki-67 using an antibody that is detectably labeled with a fluorescent agent. The coordinates of any such object of interest (e.g., a suspected cancer cell) are then used to focus and obtain a fluorescent image of a sample or subsample contacted with a fluorescently labeled MIB-1. The presence of a fluorescent signal at such coordinates is indicative of a correlation of the cancer cell with metastasis and/or survival rates.

In another aspect, microvessel density analysis can be performed and a determination of any cytokines, angiogenic agents, and the like, which are suspected of playing a role in the angiogenic activity identified. Angiogenesis is a characteristic of growing tumors. By identifying an angiogenic agent that is expressed or produced aberrantly compared to normal tissue, a therapeutic regimen can be identified that targets and modulates (e.g., increases or decreases) the angiogenic molecule or combination of molecules. For example, endothelial cell proliferation and migration are characteristic of angiogenesis and vasculogenesis. Endothelial cells can be identified by markers on the surface of such endothelial cells using a first agent that labels endothelial cells. An automated microscope system (such as that produced by ChromaVision Medical Systems, Inc., California) scans the sample for objects of interest (e.g., endothelial cells) stained with the first agent. The automated system then determines the coordinates of an object of interest and uses these coordinates to focus in on the sample or a subsample that has been contacted with a second fluorescently labeled agent. In one aspect, a second agent (e.g., an antibody, polypeptide, and/or oligonucleotide) that is labeled with a fluorescent indicator is then used to detect the specific expression or presence of any number of angiogenic agents.

Overexpression of the p53 oncogene has been implicated as the most common genetic alteration in the development of human malignancies. Investigations of a variety of malignancies, including neoplasms of breast, colon, ovary, lung, liver, mesenchyme, bladder and myeloid, have suggested a contributing role of p53 mutation in the development of malignancy. The highest frequency of expression has been demonstrated in tumors of the breast, colon, and ovary. A wide variety of normal cells do express a wildtype form of p53 but generally in restricted amounts. Overexpression and mutation of p53 have not been recognized in benign tumors or in normal tissue. In addition, p53 has also be implicated as a cocontributor to tumors. For example, BRCA-1 has been used as marker for ovarian cancer, however p53 has also been implicated as playing a role in BRCA-1 ovarian cancers (Rose and Buller, Minerva Ginecol. 54(3):201-9, 2002). Using the methods of the invention a sample is stained for BRCA-1 with a first agent and objects of interest are identified using light microscopy. The same sample or a subsample, having substantially identical coordinates with respect to an object of interest, is then contacted with a second agent comprising a fluorescent label that interacts with a p53 nucleic acid or polypeptide. The sample or subsample is then analyzed via fluorescent microscopy to identify any fluorescent signals at the coordinates associated with the object of interest to determine the presence or absence of p53 nucleic acids or polypeptides. An anti-p53 antibody useful in this embodiment includes, for example, the well-characterized DO-7 clone.

An example of an object of interest includes nucleoli, an organelle in a cell nucleus. Uses of nucleoli as objects of interest are apparent when determining cervical dysplasia. In cervical dysplasia normal or metaplastic epithelium is replaced with atypical epithelial cells that have cytologic features that are pre-malignant (nuclear hyperchromatism, nuclear enlargement and irregular outlines, increased nuclear-to-cytoplasmic ratio, increased prominence of nucleoli) and chromosomal abnormalities. The changes seen in dysplastic cells are of the same kind but of a lesser degree than those of frankly malignant cells. In addition, there are degrees of dysplasia (mild, moderate, severe).

In yet another aspect, and object of interest may be the p24 antigen of. Human immunodeficiency virus (HIV). Anti-p24 antibodies are used to detect the p24 antigen to determine the presence of the HIV virus. Further assays can then be performed using FISH to determine the genetic composition of the HIV virus using fluorescently labeled oligonucleotide probes and the like.

One method of sample preparation is to react a sample or subsample with an agent the specifically interacts with a molecule in the sample. Examples of such agents include a monoclonal antibody, a polyclonal antiserum, or an oligonucleotide or polynucleotide. Interaction of the agent with its cognate or binding partner can be detected using an enzymatic reaction, such as alkaline phosphatase or glucose oxidase or peroxidase to convert a soluble colorless substrate linked to the agent to a colored insoluble precipitate, or by directly conjugating a dye or a fluorescent molecule to the probe. In one aspect of the invention a first agent is labeled with a non-fluorescent label (e.g., a substrate that gives rise to a precipitate) and a second agent is labeled with a fluorescent label. If the same sample is to be used for both non-fluorescent detection and fluorescent detection, the non-fluorescent label preferably does not interfere with the fluorescent emissions from the fluorescent label. Examples of non-fluorescent labels include enzymes that convert a soluble colorless substrate to a colored insoluble precipitate (e.g., alkaline phosphatase, glucose oxidase, or peroxidase). Other non-fluorescent agent include small molecule reagents that change color upon interaction with a particular chemical structure.

In one aspect of Fluorescent in Situ Hybridization (FISH), a fluorescently labeled oligonucleotide (e.g., a DNA, a RNA, and a DNA-RNA molecule) is used as an agent. The fluorescently labeled oligonucleotide is contacted with a sample (e.g., a tissue sample) on a microscope slide. If the labeled oligonucleotide is complementary to a target nucleotide sequence in the sample on the slide, a bright spot will be seen when visualized on a microscope system comprising a fluorescent excitation light source. The intensity of the fluorescence will depend on a number of factors, such as the type of label, reaction conditions, amount of target in the sample, amount of oligonucleotide agent, and amount of label on the oligonucleotide agent. There are a number of methods, known in the art, that can be used to increase the amount of label attached to an agent in order to make the detection easier. FISH has an advantage that individual cells containing a target nucleotide sequences of interest can be visualized in the context of the sample or tissue sample. As mentioned above, this can be important in testing for types of diseases and disorders including cancer in which a cancer cell might penetrate normal tissues.

A given fluorescent molecule is characterized by an excitation spectrum (sometimes referred to as an absorption spectrum) and an emission spectrum. When a fluorescent molecule is irradiated with light at a wavelength within the excitation spectrum, the molecule fluoresces, emitting light at wavelengths in the emission spectrum for that particular molecule. Thus when a sample is irradiated with excitation light at a wavelength that excites a certain fluorescent molecule, the sample containing the fluorescent molecule fluoresces. In some instances the light emanating from the sample and surrounding area may be filtered to reject light outside a given fluorescent agent's emission spectrum. Thus an image acquired from a sample contacted with an agent comprising a fluorescent label shows only objects of interest in the sample that bind or interact with the fluorescently labeled agent.

The invention claimed is:

1. A method for processing a biological sample, comprising
   (a) contacting a biological sample with an agent or combination of agents that stains the biological sample for objects of interest and at least one fluorescent agent that interacts with an at least one molecule in the biological sample, wherein the at least one molecule is associated with the object of interest, and wherein the at least one fluorescents agent comprises a fluorescent indicator;
   (b) acquiring a plurality of images of the biological sample at a plurality of locations/coordinates in transmitted light;
   (c) processing the plurality of images to identify a stained object of interest;
   (d) determining a coordinate for each identified stained object of interest;
   (e) storing each of the determined coordinates corresponding to each identified stained object of interest;
   (f) applying an excitation light to the biological sample thereby causing the fluorescent indicator of the at least one fluorescent agent to fluoresce;
   (g) acquiring a fluorescent images at each of the identified coordinates; and
   (h) processing the fluorescent images to identify a fluorescently labeled at least one molecule.

2. The method of claim 1, wherein the biological sample is a tissue sample.

3. The method of claim 2, wherein the tissue sample is suspected of comprising cells having a cell proliferative disorder.

4. The method of claim 3, wherein the cell proliferative disorder is a neoplasm.

5. The method of claim 4, wherein the cell proliferative disorder is breast cancer.

6. The method of claim 1, wherein the agent is a stain selected from the group consisting of DAB, New Fuchsin, AEC, and hematoxalin.

7. The method of claim 6, wherein the object of interest is a cell.

8. The method of claim 6, wherein the object of interest is a nucleus of a cell.

9. The method of claim 1, wherein the agent is an antibody.

10. The method of claim 9, wherein the antibody specifically interacts with a cancer marker comprising a protein or polypeptide.

11. The method of claim 9, wherein the antibody is selected from the group consisting of an anti-HER2/neu antibody, anti-estrogen receptor antibody, anti-progesterone receptor antibody, anti-p53 antibody, and anti-cyclin D1 antibody.

12. The method of claim 9, wherein the antibody is enzymatically labeled.

13. The method of claim 1, wherein the plurality of images are acquired at a low or a high magnification.

14. The method of claim 1, wherein the at least one fluorescent agent is selected from the group consisting of an antibody, a protein, a polypeptide, a peptidomimetic, a polynucleotide, an oligonucleotide, a small molecule, and any combination thereof.

15. The method of claim 1, wherein the fluorescent image is acquired at a low or a high magnification.

16. The method of claim 1, wherein the method is automated.

17. A method for processing a biological sample, comprising
(a) dividing a biological sample into a plurality of subsamples with respect to a z-axis;
(b) contacting a first subsample with an agent or combination of agents that stains the first subsample for objects of interest;
(c) acquiring a plurality of images of the first subsample at a plurality of locations/coordinates in transmitted light;
(d) processing the plurality of images to identify a stained object of interest;
(e) determining a coordinate for each identified stained object of interest;
(f) storing each of the determined coordinates corresponding to each identified stained object of interest;
(g) contacting a second subsample with an at least one fluorescent agent that interacts with an at least one molecule in the biological sample, wherein the at least one molecule is associated with the object of interest, and wherein the at least one fluorescent agent comprises a fluorescent indicator;
(h) applying an excitation light to the second subsample thereby causing the fluorescent indicator of the at least one fluorescent agent to fluoresce;
(i) acquiring a fluorescent images of the second subsample at each of the identified coordinates; and
(j) processing the fluorescent images to identify a fluorescently labeled molecule.

18. The method of claim 17, wherein the biological sample is a tissue sample.

19. The method of claim 18, wherein the tissue sample is suspected of comprising cells having a cell proliferative disorder.

20. The method of claim 19, wherein the cell proliferative disorder is a neoplasm.

21. The method of claim 19, wherein the cell proliferative disorder is breast cancer.

22. The method of claim 19, wherein the fluorescent agent further characterizes the cells having a cell proliferative disorder.

23. The method of claim 17, wherein the agent is a stain selected from the group consisting of DAB, New Fuchsin, AEC, and hematoxalin.

24. The method of claim 17, wherein the object of interest is a cell.

25. The method of claim 17, wherein the object of interest is a nucleus of a cell.

26. The method of claim 17, wherein the agent is an antibody.

27. The method of claim 26, wherein the antibody is enzymatically labeled.

28. The method of claim 26, wherein the antibody specifically interacts with a cancer marker comprising a protein or polypeptide.

29. The method of claim 26, wherein the antibody is selected from the group consisting of an anti-HER2/neu antibody, anti-estrogen receptor antibody, anti-progesterone receptor antibody, anti-p53 antibody, and anti-cyclin D1 antibody.

30. The method of claim 17, wherein the plurality of images are acquired at a low or a high magnification.

31. The method of claim 17, wherein the at least one fluorescent agent is selected from the group consisting of an antibody, a protein, a polypeptide, a peptidomimetic, a polynucleotide, an oligonucleotide, and a small molecule.

32. The method of claim 17, wherein the fluorescent image is acquired at a low or a high magnification.

33. The method of claim 17, wherein the method is automated.

34. A method for identifying a therapeutic treatment for a subject having a cell proliferative disorder, comprising:
(a) dividing a biological sample from the subject into a plurality of subsamples with respect to a z-axis, wherein adjacent subsamples in the z-axis will comprise substantially identical x- and y-coordinates with respect to an object of interest found in the adjacent subsamples;
(b) contacting a first subsample with an agent or combination of agents that stains the first subsample for cells suspected of having a cell proliferative disorder;
(c) acquiring a plurality of images of the first subsample at a plurality of locations/coordinates in transmitted light;
(d) processing the plurality of images to identify a stained cell;
(e) determining a coordinate for each identified stained cell;
(f) storing each of the determined coordinates corresponding to each identified stained cell;
(g) contacting a second subsample with an at least one fluorescent agent that interacts with an at least one molecule in the biological sample, wherein the at least one molecule is associated with a biological pathway in cells that causes cell proliferative disorders, and wherein the at least one fluorescent agent comprises a fluorescent indicator;

(h) applying an excitation light to the second subsample thereby causing the fluorescent indicator of the at least one fluorescent agent to fluoresce;

(i) acquiring a fluorescent images of the second subsample at each of the identified coordinates; and (j) processing the fluorescent images to identify a fluorescently labeled molecule, wherein the presence of a fluorescent labeled molecule is indicative of the biological pathway in the cell that causes the cell proliferative disorder thereby allowing the identification of a therapeutic treatment.

35. A system for processing of a biological sample, comprising:
an image acquisition system, comprising a computer;
a monitor in operable communication with the computer;
an input device in communication with the computer;
a storage device for storing data; and
an optical system in operable communication with the computer, the optical system comprising:
a movable stage;
a visible wavelength light source adjacent to the movable stage such that light from the visible wavelength light source illuminates a sample on the movable stage;
a fluorescent excitation light source adjacent to the movable stage such that light from the fluorescent excitation light source illuminates a sample on the movable stage;
an optical sensing array in optical communication with the movable stage and configured to acquire an image at a plurality of locations in a scan area; and
an image processor in electrical communication with the sensing array and operable to process the image to detect an object of interest;
a computer program on computer readable medium with instructions to cause the image acquisition system to carry out a method comprising:
processing a first subsample that has been stained with an agent that stains an object of interest;
acquiring a plurality of images of the first subsample at a plurality of locations/coordinates in transmitted visible light;
processing the plurality of images to identify a stained object of interest;
determining a coordinate for each identified stained object of interest;
storing each of the determined coordinates corresponding to each identified stained object of interest;
processing a second subsample that has been contacted with at least one fluorescent agent that interacts with an at least one molecule in the biological sample, wherein the at least one fluorescent agent comprises a fluorescent indicator;
applying a fluorescent excitation light to the second subsample thereby causing the fluorescent indicator of the at least one fluorescent agent to fluoresce;
acquiring a fluorescent images of the second subsample at each of the identified coordinates; and
processing the fluorescent images to identify a fluorescently labeled molecule.

36. The system of claim 35, further comprising:
a filter wheel comprising a plurality of fluorescent filters interposed between the fluorescent excitation light source and the stage; and
a filter wheel control device for changing fluorescent filters during operation, wherein the filter wheel control device is in electrical communication with the computer.

37. The system of claim 35, further comprising an identification device for identifying and determining a processing parameter for a slide.

38. The system of claim 35, further comprising an automated loading and unloading member for loading and unloading of the slide.

39. The system of claim 37, wherein the processing parameter is an indication as to the visible wavelength light source or the fluorescent excitation light source and the fluorescent filter.

40. The system of claim 35, wherein the biological sample is a tissue sample.

41. The system of claim 40, wherein the tissue sample is suspected of comprising cells having a cell proliferative disorder.

42. The system of claim 41, wherein the cell proliferative disorder is a neoplasm.

43. The system of claim 41, wherein the cell proliferative disorder is breast cancer.

44. The system of claim 35, wherein the agent is a stain selected from the group consisting of DAB, New Fuchsin, AEC, and hematoxalin.

45. The system of claim 35, wherein the object of interest is a cell.

46. The system of claim 35, wherein the object of interest is a nucleus of a cell.

47. The system of claim 35, wherein the agent is an antibody.

48. The system of claim 47, wherein the antibody specifically interacts with a cancer marker comprising a protein or polypeptide.

49. The system of claim 47, wherein the antibody is selected from the group consisting of an anti-HER2/neu antibody, anti-estrogen receptor antibody, anti-progesterone receptor antibody, anti-p53 antibody, and anti-cyclin D1 antibody.

50. The system of claim 47, wherein the antibody is enzymatically labeled.

51. The system of claim 35, wherein the plurality of images are acquired at a low or a high magnification.

52. The system of claim 35, wherein the at least one fluorescent agent is selected from the group consisting of an antibody, a protein, a polypeptide, a peptidomimetic, a polynucleotide, an oligonucleotide, and a small molecule.

53. The system of claim 35, wherein the fluorescent image is acquired at a low or a high magnification.

54. The system of claim 52, wherein the fluorescent agent further characterizes the cells having a cell proliferative disorder.

* * * * *

UNITED STATES PATENT AND TRADEMARK OFFICE
CERTIFICATE OF CORRECTION

| | | |
|---|---|---|
| PATENT NO. | : 7,272,252 B2 | Page 1 of 1 |
| APPLICATION NO. | : 10/461786 | |
| DATED | : September 18, 2007 | |
| INVENTOR(S) | : Jose De La Torre-Bueno et al. | |

It is certified that error appears in the above-identified patent and that said Letters Patent is hereby corrected as shown below:

Column 6, Line 32, after "light" and before "the" please insert --can collect a new image every $1/60^{th}$ of a second. Thus--.
Column 8, Line 30, Delete "prognoses" and insert --prognose--.

Column 11, Line 39, please delete "fluorescently" and insert --fluorescent--;
Column 16, Line 25, please delete "past" and insert --pass--;
Column 16, Line 28, please delete "value is can" and insert --value can--;
Column 29, Line 41, please delete "imagining" and insert --imaging--;
Column 29, Line 67, please delete "of";
Column 33, Line 7, please delete "be" and insert --been--;
Column 33, Line 39, please delete "of.Human" and insert --of Human--;
Column 33, Line 46, please delete "the" and insert --that--;
Column 33, Line 65, please delete "agent" and insert --agents--;
Column 34, Line 17, please delete "a";
Column 34, Line 48, please delete "fluorescents" and insert --fluorescence--;
Column 34, Line 62, please delete "a";
Column 37, Line 7, please delete "a";
Column 37, Line 58, please delete "a".

Signed and Sealed this
Twenty-ninth Day of November, 2011

David J. Kappos
*Director of the United States Patent and Trademark Office*